United States Patent
Shelton, IV et al.

(10) Patent No.: US 12,414,767 B2
(45) Date of Patent: Sep. 16, 2025

(54) SURGICAL SYSTEM WITH MOTOR RELATIVE CAPACITY INTERROGATIONS

(71) Applicant: Cilag GmbH International, Zug (CH)

(72) Inventors: Frederick E. Shelton, IV, Hillsboro, OH (US); Matthew D. Cowperthwait, Cincinnati, OH (US); Nicholas J. Ross, Franklin, OH (US); Shane R. Adams, Lebanon, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 6 days.

(21) Appl. No.: 17/958,001

(22) Filed: Sep. 30, 2022

(65) Prior Publication Data
US 2024/0108333 A1   Apr. 4, 2024

Related U.S. Application Data

(60) Provisional application No. 63/411,445, filed on Sep. 29, 2022.

(51) Int. Cl.
*A61B 17/072* (2006.01)
*A61B 17/068* (2006.01)
(Continued)

(52) U.S. Cl.
CPC ...... *A61B 17/07207* (2013.01); *A61B 17/068* (2013.01); *A61B 17/0684* (2013.01); *A61B 17/072* (2013.01); *A61B 17/320092* (2013.01); *A61B 18/1445* (2013.01); *A61B 34/30* (2016.02); *G16H 40/63* (2018.01); *H02K 7/116* (2013.01); *H02K 7/145* (2013.01); *A61B 2017/00017* (2013.01); *A61B 2017/00022* (2013.01); *A61B 2017/00039* (2013.01); *A61B 2017/00075* (2013.01); *A61B 2017/00132* (2013.01); *A61B 2017/00185* (2013.01); *A61B 2017/0019* (2013.01); *A61B 2017/00221* (2013.01); *A61B 2017/00398* (2013.01);
(Continued)

(58) Field of Classification Search
CPC .......................... A61B 17/068; A61B 17/072
See application file for complete search history.

(56) References Cited

U.S. PATENT DOCUMENTS 5,403,312 A   4/1995   Yates et al.
5,817,084 A   10/1998  Jensen
(Continued)

OTHER PUBLICATIONS

IEEE Std 802.3-2012 (Revision of IEEE Std 802.3-2008, published Dec. 28, 2012.
(Continued)

*Primary Examiner* — Gloria R Weeks
(74) *Attorney, Agent, or Firm* — TROUTMAN PEPPER LOCKE LLP

(57) ABSTRACT

A surgical instrument system comprising a drive train and a control circuit is disclosed. The drive train comprises a motor and a shaft actuatable by the motor to actuate a function of an end effector. The control circuit is coupled to the motor, wherein the control circuit is configured to determine a relative excess capacity of the drive train, compare the relative excess capacity to a predetermined shifting threshold, and increase the speed of the motor based on the relative excess capacity exceeding the predetermined shifting threshold.

11 Claims, 49 Drawing Sheets

(51) Int. Cl.
- *A61B 17/32* (2006.01)
- *A61B 18/14* (2006.01)
- *A61B 34/30* (2016.01)
- *G16H 40/63* (2018.01)
- *H02K 7/116* (2006.01)
- *H02K 7/14* (2006.01)
- *A61B 17/00* (2006.01)
- *A61B 17/29* (2006.01)
- *A61B 18/00* (2006.01)
- *A61B 34/20* (2016.01)
- *A61B 90/00* (2016.01)

(52) U.S. Cl.
CPC ........... *A61B 2017/07257* (2013.01); *A61B 2017/07271* (2013.01); *A61B 2017/07278* (2013.01); *A61B 2017/07285* (2013.01); *A61B 2017/2932* (2013.01); *A61B 2017/320074* (2017.08); *A61B 2018/00642* (2013.01); *A61B 2018/0072* (2013.01); *A61B 2034/2059* (2016.02); *A61B 2090/064* (2016.02)

(56) References Cited

U.S. PATENT DOCUMENTS

| | | | |
|---|---|---|---|
| 5,878,193 A | 3/1999 | Wang et al. | |
| 6,132,368 A | 10/2000 | Cooper | |
| 6,796,476 B2 * | 9/2004 | Birk | B25C 1/08 |
| | | | 227/119 |
| 7,000,818 B2 | 2/2006 | Shelton, IV et al. | |
| 7,422,139 B2 | 9/2008 | Shelton, IV et al. | |
| 7,464,849 B2 | 12/2008 | Shelton, IV et al. | |
| 7,524,320 B2 | 4/2009 | Tierney et al. | |
| 7,670,334 B2 | 3/2010 | Hueil et al. | |
| 7,753,245 B2 | 7/2010 | Boudreaux et al. | |
| 7,845,537 B2 | 12/2010 | Shelton, IV et al. | |
| 7,980,443 B2 | 7/2011 | Scheib et al. | |
| 8,210,411 B2 * | 7/2012 | Yates | A61B 17/3205 |
| | | | 227/19 |
| 8,220,688 B2 | 7/2012 | Laurent et al. | |
| 8,308,040 B2 | 11/2012 | Huang et al. | |
| 8,393,514 B2 | 3/2013 | Shelton, IV et al. | |
| 8,505,802 B2 * | 8/2013 | Viola | A61B 17/068 |
| | | | 227/176.1 |
| 8,561,870 B2 | 10/2013 | Baxter, III et al. | |
| 8,608,045 B2 | 12/2013 | Smith et al. | |
| 8,685,004 B2 | 4/2014 | Zemlock et al. | |
| 8,733,613 B2 | 5/2014 | Huitema et al. | |
| 9,016,540 B2 | 4/2015 | Whitman et al. | |
| 9,050,083 B2 | 6/2015 | Yates et al. | |
| 9,072,535 B2 | 7/2015 | Shelton, IV et al. | |
| 9,101,358 B2 | 8/2015 | Kerr et al. | |
| 9,345,481 B2 | 5/2016 | Hall et al. | |
| 9,804,618 B2 | 10/2017 | Leimbach et al. | |
| 9,808,246 B2 * | 11/2017 | Shelton, IV | A61B 17/07207 |
| 9,913,642 B2 | 3/2018 | Leimbach et al. | |
| 9,987,095 B2 | 6/2018 | Chowaniec et al. | |
| 9,999,472 B2 | 6/2018 | Weir et al. | |
| 10,159,483 B2 | 12/2018 | Beckman et al. | |
| 10,368,865 B2 | 8/2019 | Harris et al. | |
| 10,448,948 B2 | 10/2019 | Shelton, IV et al. | |
| 10,639,037 B2 | 5/2020 | Shelton, IV et al. | |
| 10,646,220 B2 | 5/2020 | Shelton, IV et al. | |
| 10,695,057 B2 | 6/2020 | Shelton, IV et al. | |
| 10,716,565 B2 | 7/2020 | Shelton, IV et al. | |
| 10,758,226 B2 | 9/2020 | Weir et al. | |
| 10,828,028 B2 | 11/2020 | Harris et al. | |
| 10,835,245 B2 | 11/2020 | Swayze et al. | |
| 10,842,523 B2 | 11/2020 | Shelton, IV et al. | |
| 10,881,399 B2 | 1/2021 | Shelton, IV et al. | |
| 10,888,321 B2 | 1/2021 | Shelton, IV et al. | |
| 10,973,519 B2 | 4/2021 | Weir et al. | |
| 11,045,199 B2 * | 6/2021 | Mozdzierz | A61B 17/320016 |
| 11,324,501 B2 | 5/2022 | Shelton, IV et al. | |
| 11,369,366 B2 | 6/2022 | Scheib et al. | |
| 11,382,704 B2 | 7/2022 | Overmyer et al. | |
| 11,419,630 B2 | 8/2022 | Yates et al. | |
| 11,628,006 B2 | 4/2023 | Henderson et al. | |
| 2005/0040206 A1 * | 2/2005 | Adams | B25C 1/008 |
| | | | 173/117 |
| 2007/0175955 A1 | 8/2007 | Shelton et al. | |
| 2014/0263541 A1 | 9/2014 | Leimbach et al. | |
| 2014/0263552 A1 | 9/2014 | Hall et al. | |
| 2017/0079642 A1 | 3/2017 | Overmyer et al. | |
| 2017/0189019 A1 | 7/2017 | Harris et al. | |
| 2017/0296213 A1 * | 10/2017 | Swensgard | A61B 17/32 |
| 2018/0360471 A1 | 12/2018 | Parfett et al. | |
| 2019/0200981 A1 | 7/2019 | Harris et al. | |
| 2019/0201027 A1 | 7/2019 | Shelton, IV et al. | |
| 2020/0345356 A1 * | 11/2020 | Leimbach | A61B 17/07207 |
| 2021/0244407 A1 * | 8/2021 | Shelton, IV | A61B 34/30 |
| 2022/0133304 A1 * | 5/2022 | Leimbach | A61B 17/07207 |
| | | | 227/180.1 |

OTHER PUBLICATIONS

"ATM-MPLS Network Interworking Version 2.0, af-aic-0178.001" ATM Standard, The ATM Forum Technical Committee, published Aug. 2003.

* cited by examiner

SURGICAL SYSTEM WITH MOTOR RELATIVE CAPACITY INTERROGATIONS

CROSS-REFERENCE TO RELATED APPLICATIONS

This application claims the benefit under 35 U.S.C. § 119(e) to U.S. Provisional Patent Application Ser. No. 63/411,445, titled METHOD FOR CONTROLLING SURGICAL SYSTEM DURING TISSUE TREATMENT MOTION, filed Sep. 29, 2022, the disclosure of which is herein incorporated by reference in its entirety.

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
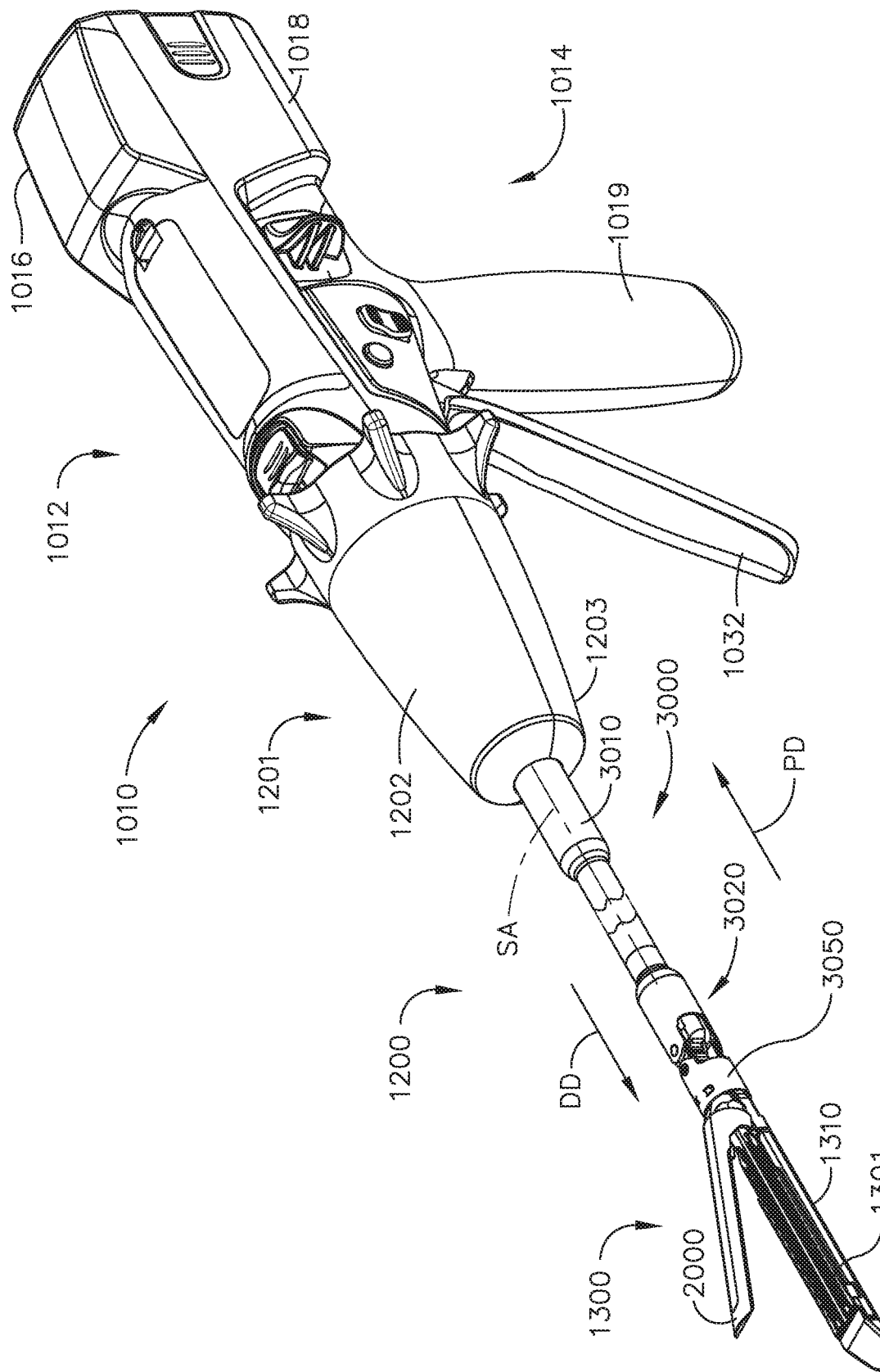
FIG. 1 is a perspective view of a powered surgical stapling system.

Applicant of the present application owns the following U.S. patent applications that were filed on Sep. 30, 2022 and which are each herein incorporated by reference in their respective entireties:

U.S. patent application Ser. No. 17/957,917, titled METHOD FOR CONTROLLING SURGICAL SYSTEM DURING TISSUE TREATMENT MOTION; published as U.S. Patent Application Publication No. 2024/0108334;

U.S. patent application Ser. No. 17/957,923, titled ADAPTING TISSUE TREATMENT MOTION PARAMETERS BASED ON SITUATIONAL PARAMETERS; published as U.S. Patent Application Publication No. 2024/0108331;

U.S. patent application Ser. No. 17/957,933, titled ADAPTIVE FIRING CONTROL ALGORITHM BASED ON MECHANICAL ACTUATION OF USER CONTROLS; patented as U.S. Pat. No. 12,310,585;

U.S. patent application Ser. No. 17/957,946, titled ADAPTATION OF INDEPENDENT FIRING AND CLOSURE POWERED STAPLING SYSTEMS; published as U.S. Patent Application Publication No. 2024/0108336;

U.S. patent application Ser. No. 17/957,954, titled MONITORING ONE DRIVE SYSTEM TO ADAPT THE MOTOR DRIVEN ASPECT OF A SECOND DRIVE SYSTEM; published as U.S. Patent Application Publication No. 2024/0108337;

U.S. patent application Ser. No. 17/957,975, titled ADJUSTMENT OF A MOTOR CONTROL PROGRAM BASED ON DETECTION OF INDIVIDUAL DEVICE DRIVE TRAIN PROPERTIES; patented as U.S. Pat. No. 12,262,890;

U.S. patent application Ser. No. 17/957,984, titled ADJUSTMENT OF A MOTOR CONTROL COMMAND SIGNAL TO ADAPT TO SYSTEM CHANGES; patented as U.S. Pat. No. 12,239,319;

U.S. patent application Ser. No. 17/957,990, titled MOTOR ADJUSTMENTS IN ABSENCE OF MOTOR DRIVE SIGNAL; patented as U.S. Pat. No. 11,974,825;

U.S. patent application Ser. No. 17/957,995, titled SURGICAL SYSTEMS WITH SYNCHRONIZED DISTRIBUTED PROCESSING CAPABILITIES; published as U.S. Patent Application Publication No. 2024/0112798;

U.S. patent application Ser. No. 17/958,008, titled MOTOR CONTROL OF SURGICAL INSTRUMENT SYSTEMS; published as U.S. Patent Application Publication No. 2024/0108329;

U.S. patent application Ser. No. 17/958,013, titled SURGICAL SYSTEM WITH AMPLITUDE AND PULSE WIDTH MODULATION ADJUSTMENTS; published as U.S. Patent Application Publication No. 2024/0108421;

U.S. patent application Ser. No. 17/958,024, titled SURGICAL ALGORITHMS WITH INCREMENTAL SENSORY ACTIONS; patented as U.S. Pat. No. 12,295,575;

U.S. patent application Ser. No. 17/958,028, titled UTILIZING LOCAL FIRING PARAMETERS TO INITIATE MOTOR CONTROL ADJUSTMENTS IN SURGICAL SYSTEMS; published as U.S. Patent Application Publication No. 2024/0108341; and U.S. patent application Ser. No. 17/958,037, titled SURGICAL SYSTEMS WITH DYNAMIC FORCE TO FIRE ADJUSTMENTS; patented as U.S. Pat. No. 11,931,037.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Figure 2:
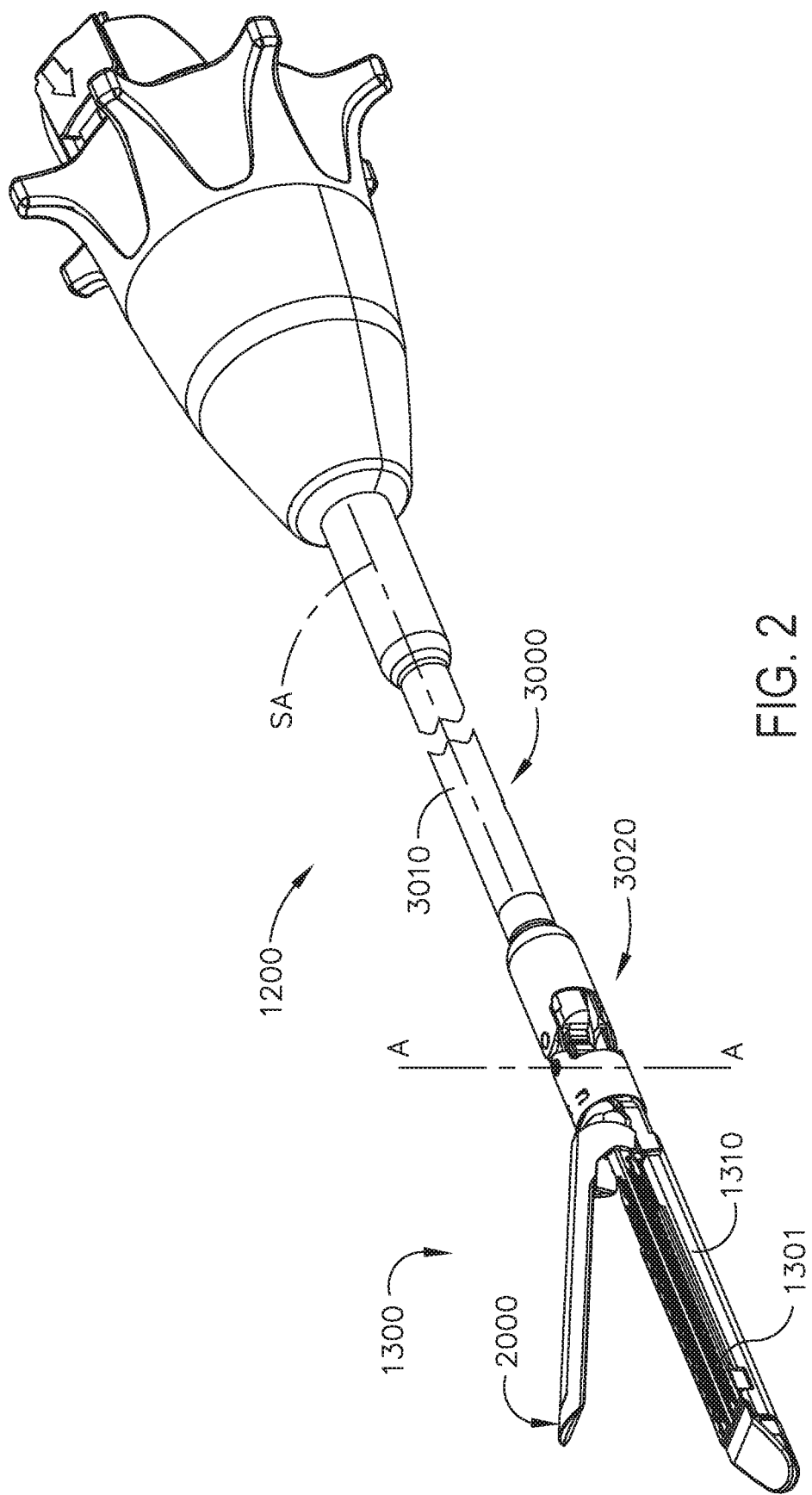
FIG. 2 is a perspective view of an interchangeable surgical shaft assembly of the powered surgical stapling system of FIG. 1.
Figure 3:
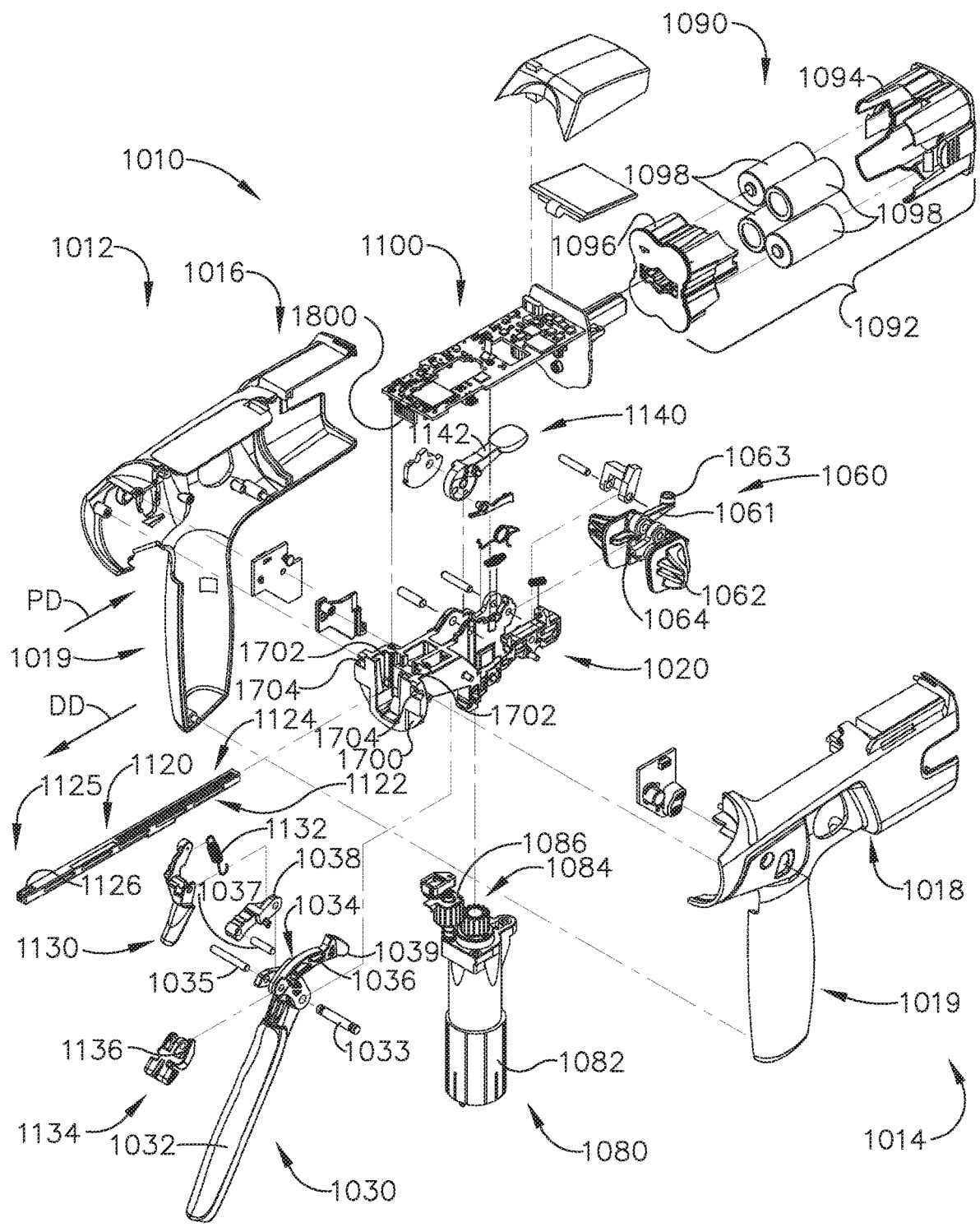
FIG. 3 is an exploded assembly view of portions of a handle assembly of the powered surgical stapling system of FIG. 1.

FIG. 1 illustrates the surgical instrument 1010 that includes an interchangeable shaft assembly 1200 operably coupled to a housing 1012. FIG. 2 illustrates the interchangeable shaft assembly 1200 detached from the housing 1012 or handle 1014. As can be seen in FIG. 3, the handle 1014 may comprise a pair of interconnectable handle housing segments 1016 and 1018 that may be interconnected by screws, snap features, adhesive, etc. In the illustrated arrangement, the handle housing segments 1016, 1018 cooperate to form a pistol grip portion 1019. FIGS. 1 and 3 depict a motor-driven surgical cutting and fastening instrument 1010 that may or may not be reused. In the illustrated embodiment, the instrument 1010 includes a proximal housing 1012 that comprises a handle 1014 that is configured to be grasped, manipulated and actuated by the clinician. The housing 1012 is configured for operable attachment to an interchangeable shaft assembly 1200 that has a surgical end effector 1300 operably coupled thereto that is configured to perform one or more surgical tasks or procedures. As the present Detailed Description proceeds, it will be understood that the various forms of interchangeable shaft assemblies disclosed herein may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate the interchangeable shaft assemblies disclosed herein and their respective equivalents. In addition, various components may be "housed" or contained in the housing or various components may be "associated with" a housing. In such instances, the components may not be contained within the housing or supported directly by the housing. The term "frame" may refer to a portion of a handheld surgical instrument. The term "frame" may also represent a portion of a robotically controlled surgical instrument and/or a portion of the robotic system that may be used to operably control a surgical instrument. For example, the interchangeable shaft assemblies disclosed herein may be employed with various robotic systems, instruments, components and methods disclosed in U.S. Pat. No. 9,072,535, entitled SURGICAL STAPLING INSTRUMENTS WITH ROTATABLE STAPLE DEPLOYMENT ARRANGEMENTS, that is incorporated by reference herein in its entirety.

The proximal housing 1012 depicted in FIG. 1 is shown in connection with an interchangeable shaft assembly 1200 (FIGS. 2, 4 and 5) that includes an end effector 1300 that comprises a surgical cutting and fastening device that is configured to operably support a surgical staple cartridge 1301 therein. The housing 1012 may be configured for use in connection with interchangeable shaft assemblies that include end effectors that are adapted to support different sizes and types of staple cartridges, have different shaft lengths, sizes, and types, etc. In addition, the housing 1012 may also be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener that can be gripped and manipulated by the clinician. As will be discussed in further detail below, the handle 1014 operably supports a plurality of drive systems therein that are configured to generate and apply various control motions to corresponding portions of the interchangeable shaft assembly that is operably attached thereto.

Referring now to FIG. 3, the handle 1014 may further include a frame 1020 that operably supports a plurality of drive systems. For example, the frame 1020 can operably support a "first" or closure drive system, generally designated as 1030, which may be employed to apply closing and opening motions to the interchangeable shaft assembly 1200 that is operably attached or coupled thereto. In at least one form, the closure drive system 1030 may include an actuator in the form of a closure trigger 1032 that is pivotally supported by the frame 1020. More specifically, as illustrated in FIG. 3, the closure trigger 1032 is pivotally coupled to the handle 1014 by a pin 1033. Such arrangement enables the closure trigger 1032 to be manipulated by a clinician such that when the clinician grips the pistol grip portion 1019 of the handle 1014, the closure trigger 1032 may be easily pivoted from a starting or "unactuated" position to an "actuated" position and more particularly to a fully compressed or fully actuated position. The closure trigger 1032 may be biased into the unactuated position by spring or other biasing arrangement (not shown). In various forms, the closure drive system 1030 further includes a closure linkage assembly 1034 that is pivotally coupled to the closure trigger 1032. As can be seen in FIG. 3, the closure linkage assembly 1034 may include a first closure link 1036 and a second closure link 1038 that are pivotally coupled to the closure trigger 1032 by a pin 1035. The second closure link 1038 may also be referred to herein as an "attachment member" and include a transverse attachment pin 1037.

Still referring to FIG. 3, it can be observed that the first closure link 1036 may have a locking wall or end 1039 thereon that is configured to cooperate with a closure release assembly 1060 that is pivotally coupled to the frame 1020. In at least one form, the closure release assembly 1060 may comprise a release button assembly 1062 that has a distally protruding locking pawl 1064 formed thereon. The release button assembly 1062 may be pivoted in a counterclockwise direction by a release spring (not shown). As the clinician depresses the closure trigger 1032 from its unactuated position towards the pistol grip portion 1019 of the handle 1014, the first closure link 1036 pivots upward to a point wherein the locking pawl 1064 drops into retaining engagement with the locking wall 1039 on the first closure link 1036 thereby preventing the closure trigger 1032 from returning to the unactuated position. Thus, the closure release assembly 1060 serves to lock the closure trigger 1032 in the fully actuated position. When the clinician desires to unlock the closure trigger 1032 to permit it to be biased to the unactuated position, the clinician simply pivots the closure release button assembly 1062 such that the locking pawl 1064 is moved out of engagement with the locking wall 1039 on the first closure link 1036. When the locking pawl 1064 has been moved out of engagement with the first closure link 1036, the closure trigger 1032 may pivot back to the unactuated position. Other closure trigger locking and release arrangements may also be employed.

An arm 1061 may extend from the closure release button assembly 1062. A magnetic element 1063, such as a permanent magnet, for example, may be mounted to the arm 1061. When the closure release button assembly 1062 is rotated from its first position to its second position, the magnetic element 1063 can move toward a circuit board 1100. The circuit board 1100 can include at least one sensor that is configured to detect the movement of the magnetic element 1063. In at least one embodiment, for example, a "Hall Effect" sensor (not shown) can be mounted to the bottom surface of the circuit board 1100. The Hall Effect sensor can be configured to detect changes in a magnetic field surrounding the Hall Effect sensor caused by the movement of the magnetic element 1063. The Hall Effect sensor can be in signal communication with a microcontroller, for example, which can determine whether the closure release button assembly 1062 is in its first position, which is associated with the unactuated position of the closure trigger 1032 and the open configuration of the end effector, its second position, which is associated with the actuated position of the closure trigger 1032 and the closed configuration of the end effector, and/or any position between the first position and the second position.

In at least one form, the handle 1014 and the frame 1020 may operably support another drive system referred to herein as a firing drive system 1080 that is configured to apply firing motions to corresponding portions of the interchangeable shaft assembly attached thereto. The firing drive system 1080 may also be referred to herein as a "second drive system". The firing drive system 1080 may employ an electric motor 1082 that is located in the pistol grip portion 1019 of the handle 1014. In various forms, the motor 1082 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor 1082 may be powered by a power source 1090 that in one form may comprise a removable power pack 1092. As can be seen in FIG. 3, for example, the power pack 1092 may comprise a proximal housing portion 1094 that is configured for attachment to a distal housing portion 1096. The proximal housing portion 1094 and the distal housing portion 1096 are configured to operably support a plurality of batteries 1098 therein. Batteries 1098 may each comprise, for example, a Lithium Ion ("LI") or other suitable battery. The distal housing portion 1096 is configured for removable operable attachment to the circuit board 1100 which is also operably coupled to the motor 1082. A number of batteries 1098 may be connected in series may be used as the power source for the surgical instrument 1010. In addition, the power source 1090 may be replaceable and/or rechargeable.

As outlined above with respect to other various forms, the electric motor 1082 can include a rotatable shaft (not shown) that operably interfaces with a gear reducer assembly 1084 that is mounted in meshing engagement with a set, or rack, of drive teeth 1122 on a longitudinally movable drive member 1120. In use, a voltage polarity provided by the power source 1090 can operate the electric motor 1082 in a clockwise direction wherein the voltage polarity applied to the electric motor by the battery can be reversed in order to operate the electric motor 1082 in a counter-clockwise direction. When the electric motor 1082 is rotated in one direction, the drive member 1120 will be axially driven in the distal direction "DD". When the motor 1082 is driven in the opposite rotary direction, the drive member 1120 will be axially driven in a proximal direction "PD". The handle 1014 can include a switch which can be configured to reverse the polarity applied to the electric motor 1082 by the power source 1090. As with the other forms described herein, the handle 1014 can also include a sensor that is configured to detect the position of the drive member 1120 and/or the direction in which the drive member 1120 is being moved.

Actuation of the motor 1082 can be controlled by a firing trigger 1130 that is pivotally supported on the handle 1014. The firing trigger 1130 may be pivoted between an unactuated position and an actuated position. The firing trigger 1130 may be biased into the unactuated position by a spring 1132 or other biasing arrangement such that when the clinician releases the firing trigger 1130, it may be pivoted or otherwise returned to the unactuated position by the spring 1132 or biasing arrangement. In at least one form, the firing trigger 1130 can be positioned "outboard" of the closure trigger 1032 as was discussed above. In at least one form, a firing trigger safety button 1134 may be pivotally mounted to the closure trigger 1032 by the pin 1035. The safety button 1134 may be positioned between the firing trigger 1130 and the closure trigger 1032 and have a pivot arm 1136 protruding therefrom. When the closure trigger 1032 is in the unactuated position, the safety button 1134 is contained in the handle 1014 where the clinician cannot readily access it and move it between a safety position preventing actuation of the firing trigger 1130 and a firing position wherein the firing trigger 1130 may be fired. As the clinician depresses the closure trigger 1032, the safety button 1134 and the firing trigger 1130 pivot down wherein they can then be manipulated by the clinician.

As indicated above, in at least one form, the longitudinally movable drive member 1120 has a rack of teeth 1122 formed thereon for meshing engagement with a corresponding drive gear 1086 of the gear reducer assembly 1084. At least one form also includes a manually-actuatable "bailout" assembly 1140 that is configured to enable the clinician to manually retract the longitudinally movable drive member 1120 should the motor 1082 become disabled. The bailout assembly 1140 may include a lever or bailout handle assembly 1142 that is configured to be manually pivoted into ratcheting engagement with teeth 1124 also provided in the drive member 1120. Thus, the clinician can manually retract the drive member 1120 by using the bailout handle assembly 1142 to ratchet the drive member 1120 in the proximal direction "PD". U.S. Pat. No. 8,608,045, entitled POWERED SURGICAL CUTTING AND STAPLING APPARATUS WITH MANUALLY RETRACTABLE FIRING SYSTEM, discloses bailout arrangements and other components, arrangements and systems that may also be employed with the various instruments disclosed herein. U.S. Pat. No. 8,608,045, is hereby incorporated by reference herein in its entirety.

Figure 4:
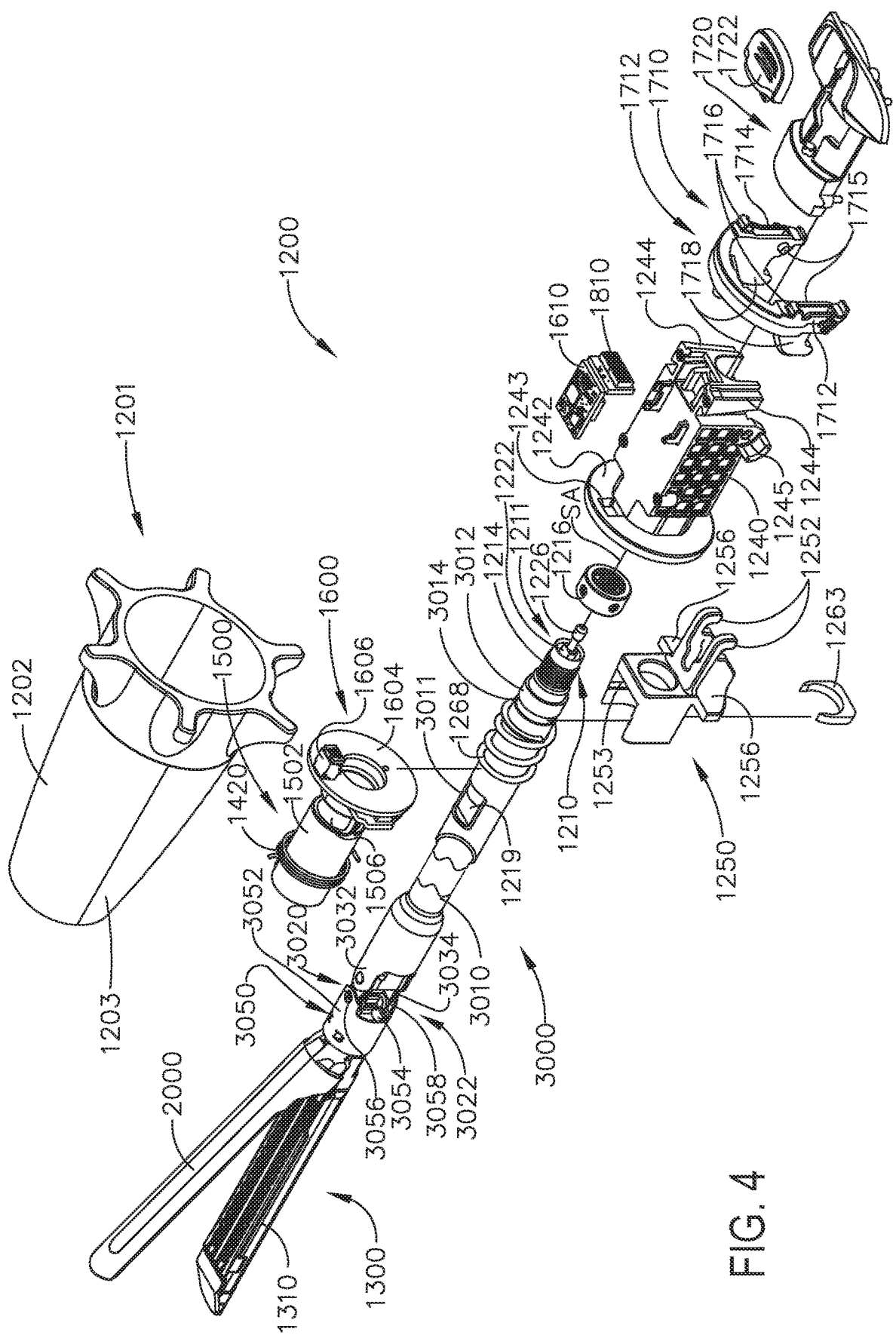
FIG. 4 is an exploded assembly view of the interchangeable surgical shaft assembly of FIG. 2.
Figure 5:
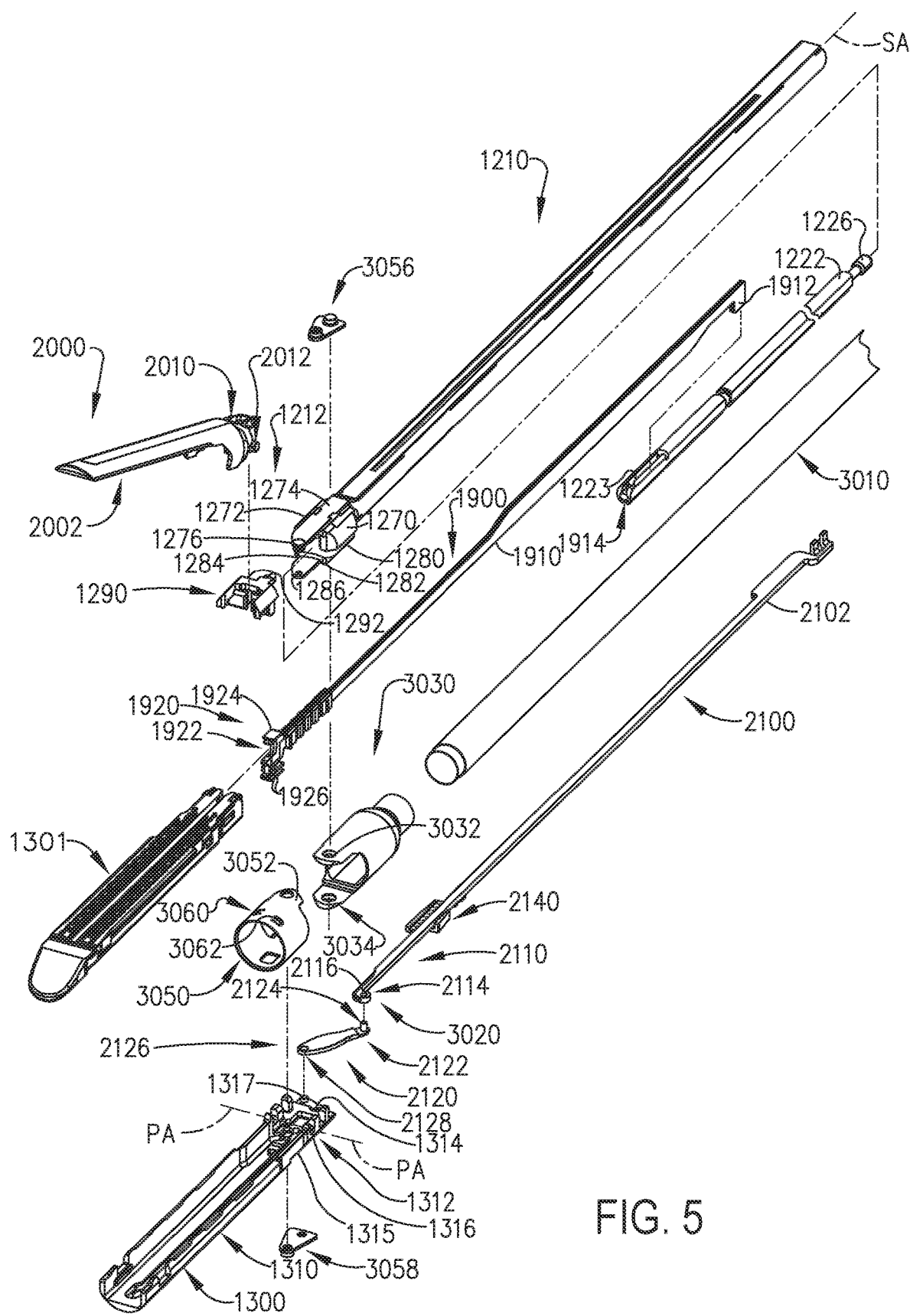
FIG. 5 is another partial exploded assembly view of a portion of the interchangeable surgical shaft assembly of FIG. 4.

Turning now to FIGS. 2 and 5, the interchangeable shaft assembly 1200 includes a surgical end effector 1300 that comprises an elongate channel 1310 that is configured to operably support a staple cartridge 1301 therein. The end effector 1300 may further include an anvil 2000 that is pivotally supported relative to the elongate channel 1310. The interchangeable shaft assembly 1200 may further include an articulation joint 3020 and an articulation lock 2140 which can be configured to releasably hold the end effector 1300 in a desired position relative to a shaft axis SA. Examples of various features of at least one form of the end effector 1300, the articulation joint 3020 and articulation locks may be found in U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541. The entire disclosure of U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541, is hereby incorporated by reference herein. As can be seen in FIG. 4, the interchangeable shaft assembly 1200 can further include a proximal housing or nozzle 1201 comprised of nozzle portions 1202 and 1203.

The interchangeable shaft assembly 1200 can further include a closure system or closure member assembly 3000 which can be utilized to close and/or open the anvil 2000 of the end effector 1300. The shaft assembly 1200 can include a spine 1210 that is configured to, one, slidably support a firing member therein and, two, slidably support the closure member assembly 3000 which extends around the spine 1210. As can be seen in FIG. 5, a distal end 1212 of spine 1210 terminates in an upper lug mount feature 1270 and in a lower lug mount feature 1280. The upper lug mount feature 1270 is formed with a lug slot 1272 therein that is adapted to mountingly support an upper mounting link 1274 therein. Similarly, the lower lug mount feature 1280 is formed with a lug slot 1282 therein that is adapted to mountingly support a lower mounting link 1284 therein. The upper mounting link 1274 includes a pivot socket 1276 therein that is adapted to rotatably receive therein a pivot pin 1292 that is formed on a channel cap or anvil retainer 1290 that is attached to a proximal end portion 1312 of the elongate channel 1310. The lower mounting link 1284 includes lower pivot pin 1286 that adapted to be received within a pivot hole 1314 formed in the proximal end portion 1312 of the elongate channel 1310. See FIG. 5. The lower pivot pin 1286 is vertically aligned with the pivot socket 1276 to define an articulation axis AA about which the surgical end effector 1300 may articulate relative to the shaft axis SA. See FIG. 2.

In the illustrated example, the surgical end effector 1300 is selectively articulatable about the articulation axis AA by an articulation system 2100. In one form, the articulation system 2100 includes proximal articulation driver 2102 that is pivotally coupled to an articulation link 2120. As can be most particularly seen in FIG. 5, an offset attachment lug 2114 is formed on a distal end 2110 of the proximal articulation driver 2102. A pivot hole 2116 is formed in the offset attachment lug 2114 and is configured to pivotally receive therein a proximal link pin 2124 formed on the proximal end 2122 of the articulation link 2120. A distal end 2126 of the articulation link 2120 includes a pivot hole 2128 that is configured to pivotally receive therein a channel pin 1317 formed on the proximal end portion 1312 of the elongate channel 1310. Thus, axial movement of proximal articulation driver 2102 will thereby apply articulation motions to the elongate channel 1310 to thereby cause the surgical end effector 1300 to articulate about the articulation axis AA relative to the spine 1210. Further details concerning the construction and operation of the articulation system 2100 may be found in various references incorporated by reference herein including U.S. patent application Ser. No. 15/635,631, filed Jun. 28, 2017, entitled SURGICAL INSTRUMENT WITH AXIALLY MOVABLE CLOSURE MEMBER, now U.S.

Patent Application Publication No. 2019/0000464, the entire disclosure of which is hereby incorporated by reference herein. In various circumstances, the proximal articulation driver 2102 can be held in position by an articulation lock 2140 when the proximal articulation driver 2102 is not being moved in the proximal or distal directions. Additional details regarding an example of an articulation lock 2140 may be found in U.S. patent application Ser. No. 15/635,631, now U.S. Patent Application Publication No. 2019/0000464, as well as in other references incorporated by reference herein.

In various circumstances, the spine 1210 can comprise a proximal end 1211 which is rotatably supported in a chassis 1240. In one arrangement, for example, the proximal end 1211 of the spine 1210 has a thread 1214 formed thereon for threaded attachment to a spine bearing 1216 configured to be supported within the chassis 1240. See FIG. 4. Such an arrangement facilitates rotatable attachment of the spine 1210 to the chassis 1240 such that the spine 1210 may be selectively rotated about a shaft axis SA relative to the chassis 1240.

Referring primarily to FIG. 4, the interchangeable shaft assembly 1200 includes a closure shuttle 1250 that is slidably supported within the chassis 1240 such that it may be axially moved relative thereto. The closure shuttle 1250 includes a pair of proximally-protruding hooks 1252 that are configured for attachment to the attachment pin 1037 (FIG. 3) that is attached to the second closure link 1038 as will be discussed in further detail below. In at least one example, the closure member assembly 3000 comprises a proximal closure member segment 3010 that has a proximal end 3012 that is coupled to the closure shuttle 1250 for relative rotation thereto. For example, a U shaped connector 1263 is inserted into an annular slot 3014 in the proximal end 3012 of the proximal closure member segment 3010 and is retained within vertical slots 1253 in the closure shuttle 1250. Such an arrangement serves to attach the proximal closure member segment 3010 to the closure shuttle 1250 for axial travel therewith while enabling the proximal closure member segment 3010 to rotate relative to the closure shuttle 1250 about the shaft axis SA. A closure spring 1268 is journaled on the proximal closure member segment 3010 and serves to bias the proximal closure member segment 3010 in the proximal direction "PD" which can serve to pivot the closure trigger 1032 into the unactuated position when the shaft assembly is operably coupled to the handle 1014.

In at least one form, the interchangeable shaft assembly 1200 may further include an articulation joint 3020. Other interchangeable shaft assemblies, however, may not be capable of articulation. As can be seen in FIG. 5, for example, a distal closure member or distal closure tube segment 3030 is coupled to the distal end of the proximal closure member segment 3010. The articulation joint 3020 includes a double pivot closure sleeve assembly 3022. According to various forms, the double pivot closure sleeve assembly 3022 includes an end effector closure tube 3050 having upper and lower distally projecting tangs 3052, 3054. An upper double pivot link 3056 includes upwardly projecting distal and proximal pivot pins that engage respectively an upper distal pin hole in the upper proximally projecting tang 3052 and an upper proximal pin hole in an upper distally projecting tang 3032 on the distal closure tube segment 3030. A lower double pivot link 3058 includes upwardly projecting distal and proximal pivot pins that engage respectively a lower distal pin hole in the lower proximally projecting tang 3054 and a lower proximal pin hole in the lower distally projecting tang 3034. See FIGS. 4 and 5. As will be discussed in further detail below, the closure member assembly 3000 is translated distally (direction "DD") to close the anvil 2000, for example, in response to the actuation of the closure trigger 1032. The anvil 2000 is opened by proximally translating the closure member assembly 3000 which causes the end effector closure sleeve to interact with the anvil 2000 and pivot it to an open position.

As was also indicated above, the interchangeable shaft assembly 1200 further includes a firing member 1900 that is supported for axial travel within the spine 1210. The firing member 1900 includes an intermediate firing shaft portion 1222 that is configured for attachment to a distal cutting portion or knife bar 1910. The intermediate firing shaft portion 1222 may include a longitudinal slot 1223 in the distal end thereof which can be configured to receive a tab 1912 on the proximal end of the distal knife bar 1910. The longitudinal slot 1223 and the proximal end tab 1912 can be sized and configured to permit relative movement therebetween and can comprise a slip joint 1914. The slip joint 1914 can permit the intermediate firing shaft portion 1222 of the firing member 1900 to be moved to articulate the end effector 1300 without moving, or at least substantially moving, the knife bar 1910. Once the end effector 1300 has been suitably oriented, the intermediate firing shaft portion 1222 can be advanced distally until a proximal sidewall of the longitudinal slot 1223 comes into contact with the tab 1912 in order to advance the knife bar 1910 and fire the staple cartridge 1301 positioned within the channel 1310. The knife bar 1910 includes a knife portion 1920 that includes a blade or tissue cutting edge 1922 and includes an upper anvil engagement tab 1924 and lower channel engagement tabs 1926. Various firing member configurations and operations are disclosed in various other references incorporated herein by reference.

Embodiments are also envisioned where, in lieu of a slip joint 1914, a shifter assembly can be used. Details of such a shifter assembly and corresponding components, assemblies, and systems can be found in U.S. patent application Ser. No. 15/635,521, entitled SURGICAL INSTRUMENT LOCKOUT ARRANGEMENT, which is incorporated by reference herein in its entirety.

As can be seen in FIG. 4, the shaft assembly 1200 further includes a switch drum 1500 that is rotatably received on proximal closure member segment 3010. The switch drum 1500 comprises a hollow shaft segment 1502 that has a shaft boss formed thereon for receiving an outwardly protruding actuation pin therein. In various circumstances, the actuation pin extends through a longitudinal slot provided in the lock sleeve to facilitate axial movement of the lock sleeve when it is engaged with the articulation driver. A rotary torsion spring 1420 is configured to engage the boss on the switch drum 1500 and a portion of the nozzle housing 1203 to apply a biasing force to the switch drum 1500. The switch drum 1500 can further comprise at least partially circumferential openings 1506 defined therein which can be configured to receive circumferential mounts extending from the nozzle portions 1202, 1203 and permit relative rotation, but not translation, between the switch drum 1500 and the nozzle 1201. The mounts also extend through openings 3011 in the proximal closure member segment 3010 to be seated in recesses 1219 in the spine 1210. Rotation of the switch drum 1500 about the shaft axis SA will ultimately result in the rotation of the actuation pin and the lock sleeve between its engaged and disengaged positions. In one arrangement, the rotation of the switch drum 1500 may be linked to the axial advancement of the closure tube or closure member. Thus, in essence, actuation of the closure system may operably engage and disengage the articulation drive system with the firing drive system in the various manners described in further detail in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, and U.S. Pat. No. 9,913,642, entitled SURGICAL INSTRUMENT COMPRISING A SENSOR SYSTEM, the entire disclosures of each being hereby incorporated by reference herein. For example, when the closure tube is in its proximal-most position corresponding to a "jaws open" position, the closure member segment 3010 will have positioned the switch drum 1500 so as to link the articulation system with the firing drive system. When, the closure tube has been moved to its distal position corresponding to a "jaws closed" position, the closure tube has rotated the switch drum 1500 to a position wherein the articulation system is delinked from the firing drive system.

As also illustrated in FIG. 4, the shaft assembly 1200 can comprise a slip ring assembly 1600 which can be configured to conduct electrical power to and/or from the end effector 1300 and/or communicate signals to and/or from the end effector 1300, for example. The slip ring assembly 1600 can comprise a proximal connector flange 1604 that is mounted to a chassis flange 1242 that extends from the chassis 1240 and a distal connector flange that is positioned within a slot defined in the shaft housings. The proximal connector flange 1604 can comprise a first face and the distal connector flange can comprise a second face which is positioned adjacent to and movable relative to the first face. The distal connector flange can rotate relative to the proximal connector flange 1604 about the shaft axis SA. The proximal connector flange 1604 can comprise a plurality of concentric, or at least substantially concentric, conductors defined in the first face thereof. A connector can be mounted on the proximal side of the connector flange and may have a plurality of contacts wherein each contact corresponds to and is in electrical contact with one of the conductors. Such an arrangement permits relative rotation between the proximal connector flange 1604 and the distal connector flange while maintaining electrical contact therebetween. The proximal connector flange 1604 can include an electrical connector 1606 which can place the conductors in signal communication with a shaft circuit board 1610 mounted to the shaft chassis 1240, for example. In at least one instance, a wiring harness comprising a plurality of conductors can extend between the electrical connector 1606 and the shaft circuit board 1610. The electrical connector 1606 may extend proximally through a connector opening 1243 defined in the chassis flange 1242. See FIG. 4. Further details regarding slip ring assembly 1600 may be found in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552, and U.S. Pat. No. 9,345,481, entitled STAPLE CARTRIDGE TISSUE THICKNESS SENSOR SYSTEM, for example. U.S. patent application Ser. No. 13/803,086, now U.S. Patent Application Publication No. 2014/0263541, U.S. patent application Ser. No. 13/800,067, now U.S. Patent Application Publication No. 2014/0263552, and U.S. Pat. No. 9,345,481 are each hereby incorporated by reference herein in their respective entireties.

As discussed above, the shaft assembly 1200 can include a proximal portion which is fixably mounted to the handle 1014 and a distal portion which is rotatable about a longitudinal axis. The rotatable distal shaft portion can be rotated relative to the proximal portion about the slip ring assembly 1600, as discussed above. The distal connector flange of the slip ring assembly 1600 can be positioned within the rotatable distal shaft portion. Moreover, further to the above, the switch drum 1500 can also be positioned within the rotatable distal shaft portion. When the rotatable distal shaft portion is rotated, the distal connector flange and the switch drum 1500 can be rotated synchronously with one another. In addition, the switch drum 1500 can be rotated between a first position and a second position relative to the distal connector flange. When the switch drum 1500 is in its first position, the articulation drive system may be operably disengaged from the firing drive system and, thus, the operation of the firing drive system may not articulate the end effector 1300 of the shaft assembly 1200. When the switch drum 1500 is in its second position, the articulation drive system may be operably engaged with the firing drive system and, thus, the operation of the firing drive system may articulate the end effector 1300 of the shaft assembly 1200. When the switch drum 1500 is moved between its first position and its second position, the switch drum 1500 is moved relative to the distal connector flange. In various instances, the shaft assembly 1200 can comprise at least one sensor configured to detect the position of the switch drum 1500.

Referring again to FIG. 4, the chassis 1240 includes at least one, and preferably two, tapered attachment portions 1244 formed thereon that are adapted to be received within corresponding dovetail slots 1702 formed within a distal attachment flange portion 1700 of the frame 1020. See FIG. 3. Each dovetail slot 1702 may be tapered or, stated another way, be somewhat V-shaped to seatingly receive the attachment portions 1244 therein. As can be further seen in FIG. 4, a shaft attachment lug 1226 is formed on the proximal end of the intermediate firing shaft portion 1222. As will be discussed in further detail below, when the interchangeable shaft assembly 1200 is coupled to the handle 1014, the shaft attachment lug 1226 is received in a firing shaft attachment cradle 1126 formed in a distal end 1125 of the longitudinal drive member 1120. See FIG. 3.

Various shaft assembly embodiments employ a latch system 1710 for removably coupling the shaft assembly 1200 to the housing 1012 and more specifically to the frame 1020. As can be seen in FIG. 4, for example, in at least one form, the latch system 1710 includes a lock member or lock yoke 1712 that is movably coupled to the chassis 1240. In the illustrated embodiment, for example, the lock yoke 1712 has a U-shape with two spaced downwardly extending legs 1714. The legs 1714 each have a pivot lug 1715 formed thereon that are adapted to be received in corresponding holes 1245 formed in the chassis 1240. Such arrangement facilitates pivotal attachment of the lock yoke 1712 to the chassis 1240. The lock yoke 1712 may include two proximally protruding lock lugs 1716 that are configured for releasable engagement with corresponding lock detents or grooves 1704 in the distal attachment flange portion 1700 of the frame 1020. See FIG. 3. In various forms, the lock yoke 1712 is biased in the proximal direction by spring or biasing member (not shown). Actuation of the lock yoke 1712 may be accomplished by a latch button 1722 that is slidably mounted on a latch actuator assembly 1720 that is mounted to the chassis 1240. The latch button 1722 may be biased in a proximal direction relative to the lock yoke 1712. As will be discussed in further detail below, the lock yoke 1712 may be moved to an unlocked position by biasing the latch button in the distal direction which also causes the lock yoke 1712 to pivot out of retaining engagement with the distal attachment flange portion 1700 of the frame 1020. When the lock yoke 1712 is in "retaining engagement" with the distal attachment flange portion 1700 of the frame 1020, the lock lugs 1716 are retainingly seated within the corresponding lock detents or grooves 1704 in the distal attachment flange portion 1700.

When employing an interchangeable shaft assembly that includes an end effector of the type described herein that is adapted to cut and fasten tissue, as well as other types of end effectors, it may be desirable to prevent inadvertent detachment of the interchangeable shaft assembly from the housing during actuation of the end effector. For example, in use the clinician may actuate the closure trigger 1032 to grasp and manipulate the target tissue into a desired position. Once the target tissue is positioned within the end effector 1300 in a desired orientation, the clinician may then fully actuate the closure trigger 1032 to close the anvil 2000 and clamp the target tissue in position for cutting and stapling. In that instance, the first drive system 1030 has been fully actuated. After the target tissue has been clamped in the end effector 1300, it may be desirable to prevent the inadvertent detachment of the shaft assembly 1200 from the housing 1012. One form of the latch system 1710 is configured to prevent such inadvertent detachment.

As can be most particularly seen in FIG. 4, the lock yoke 1712 includes at least one and preferably two lock hooks 1718 that are adapted to contact corresponding lock lug portions 1256 that are formed on the closure shuttle 1250. When the closure shuttle 1250 is in an unactuated position (i.e., the first drive system 1030 is unactuated and the anvil 2000 is open), the lock yoke 1712 may be pivoted in a distal direction to unlock the interchangeable shaft assembly 1200 from the housing 1012. When in that position, the lock hooks 1718 do not contact the lock lug portions 1256 on the closure shuttle 1250. However, when the closure shuttle 1250 is moved to an actuated position (i.e., the first drive system 1030 is actuated and the anvil 2000 is in the closed position), the lock yoke 1712 is prevented from being pivoted to an unlocked position. Stated another way, if the clinician were to attempt to pivot the lock yoke 1712 to an unlocked position or, for example, the lock yoke 1712 was inadvertently bumped or contacted in a manner that might otherwise cause it to pivot distally, the lock hooks 1718 on the lock yoke 1712 will contact the lock lug portions 1256 on the closure shuttle 1250 and prevent movement of the lock yoke 1712 to an unlocked position.

Attachment of the interchangeable shaft assembly 1200 to the handle 1014 will now be described. To commence the coupling process, the clinician may position the chassis 1240 of the interchangeable shaft assembly 1200 above or adjacent to the distal attachment flange portion 1700 of the frame 1020 such that the tapered attachment portions 1244 formed on the chassis 1240 are aligned with the dovetail slots 1702 in the frame 1020. The clinician may then move the shaft assembly 1200 along an installation axis that is perpendicular to the shaft axis SA to seat the attachment portions 1244 in "operable engagement" with the corresponding dovetail slots 1702. In doing so, the shaft attachment lug 1226 on the intermediate firing shaft portion 1222 will also be seated in the cradle 1126 in the longitudinally movable drive member 1120 and the portions of the pin 1037 on the second closure link 1038 will be seated in the corresponding hooks 1252 in the closure shuttle 1250. As used herein, the term "operable engagement" in the context of two components means that the two components are sufficiently engaged with each other so that upon application of an actuation motion thereto, the components may carry out their intended action, function and/or procedure.

At least five systems of the interchangeable shaft assembly 1200 can be operably coupled with at least five corresponding systems of the handle 1014. A first system can comprise a frame system which couples and/or aligns the frame 1020 or spine 1210 of the shaft assembly 1200 with the frame 1020 of the handle 1014. Another system can comprise a closure drive system 1030 which can operably connect the closure trigger 1032 of the handle 1014 and a closure tube of the shaft assembly 1200. As outlined above, the closure shuttle 1250 of the shaft assembly 1200 can be engaged with the pin 1037 on the second closure link 1038. Another system can comprise the firing drive system 1080 which can operably connect the firing trigger 1130 of the handle 1014 with the intermediate firing shaft portion 1222 of the shaft assembly 1200. As outlined above, the shaft attachment lug 1226 can be operably connected with the cradle 1126 of the longitudinal drive member 1120. Another system can comprise an electrical system which can signal to a controller in the handle 1014, such as microcontroller, for example, that a shaft assembly, such as shaft assembly 1200, for example, has been operably engaged with the handle 1014 and/or, two, conduct power and/or communication signals between the shaft assembly 1200 and the handle 1014. For instance, the shaft assembly 1200 can include an electrical connector 1810 that is operably mounted to the shaft circuit board 1610. The electrical connector 1810 is configured for mating engagement with a corresponding electrical connector 1800 on the circuit board 1100. Further details regarding the circuitry and control systems may be found in U.S. patent application Ser. No. 13/803,086, now U.S. Patent Application Publication No. 2014/0263541 entitled ARTICULATABLE SURGICAL INSTRUMENT COMPRISING AN ARTICULATION LOCK, and U.S. patent application Ser. No. 14/226,142, now U.S. Pat. No. 9,913,642 entitled SURGICAL INSTRUMENT COMPRISING A SENSOR SYSTEM, the entire disclosures of each which were previously incorporated by reference herein. The fifth system may consist of the latching system for releasably locking the shaft assembly 1200 to the handle 1014.

The anvil 2000 in the illustrated example includes an anvil body 2002 that terminates in an anvil mounting portion 2010. The anvil mounting portion 2010 is movably or pivotably supported on the elongate channel 1310 for selective pivotal travel relative thereto about a fixed anvil pivot axis PA that is transverse to the shaft axis SA. In the illustrated arrangement, a pivot member or anvil trunnion 2012 extends laterally out of each lateral side of the anvil mounting portion 2010 to be received in a corresponding trunnion cradle 1316 formed in the upstanding walls 1315 of the proximal end portion 1312 of the elongate channel 1310. The anvil trunnions 2012 are pivotally retained in their corresponding trunnion cradle 1316 by the channel cap or anvil retainer 1290. The channel cap or anvil retainer 1290 includes a pair of attachment lugs that are configured to be retainingly received within corresponding lug grooves or notches formed in the upstanding walls 1315 of the proximal end portion 1312 of the elongate channel 1310. See FIG. 5.

Still referring to FIG. 5, in at least one arrangement, the distal closure member or end effector closure tube 3050 employs two axially offset, proximal and distal positive jaw opening features 3060 and 3062. The positive jaw opening features 3060, 3062 are configured to interact with corresponding relieved areas and stepped portions formed on the anvil mounting portion 2010 as described in further detail in U.S. patent application Ser. No. 15/635,631, entitled SURGICAL INSTRUMENT WITH AXIALLY MOVABLE CLOSURE MEMBER, now U.S. Patent Application Publication No. 2019/0000464, the entire disclosure which has been herein incorporated by reference. Other jaw opening arrangements may be employed.

Figure 6:
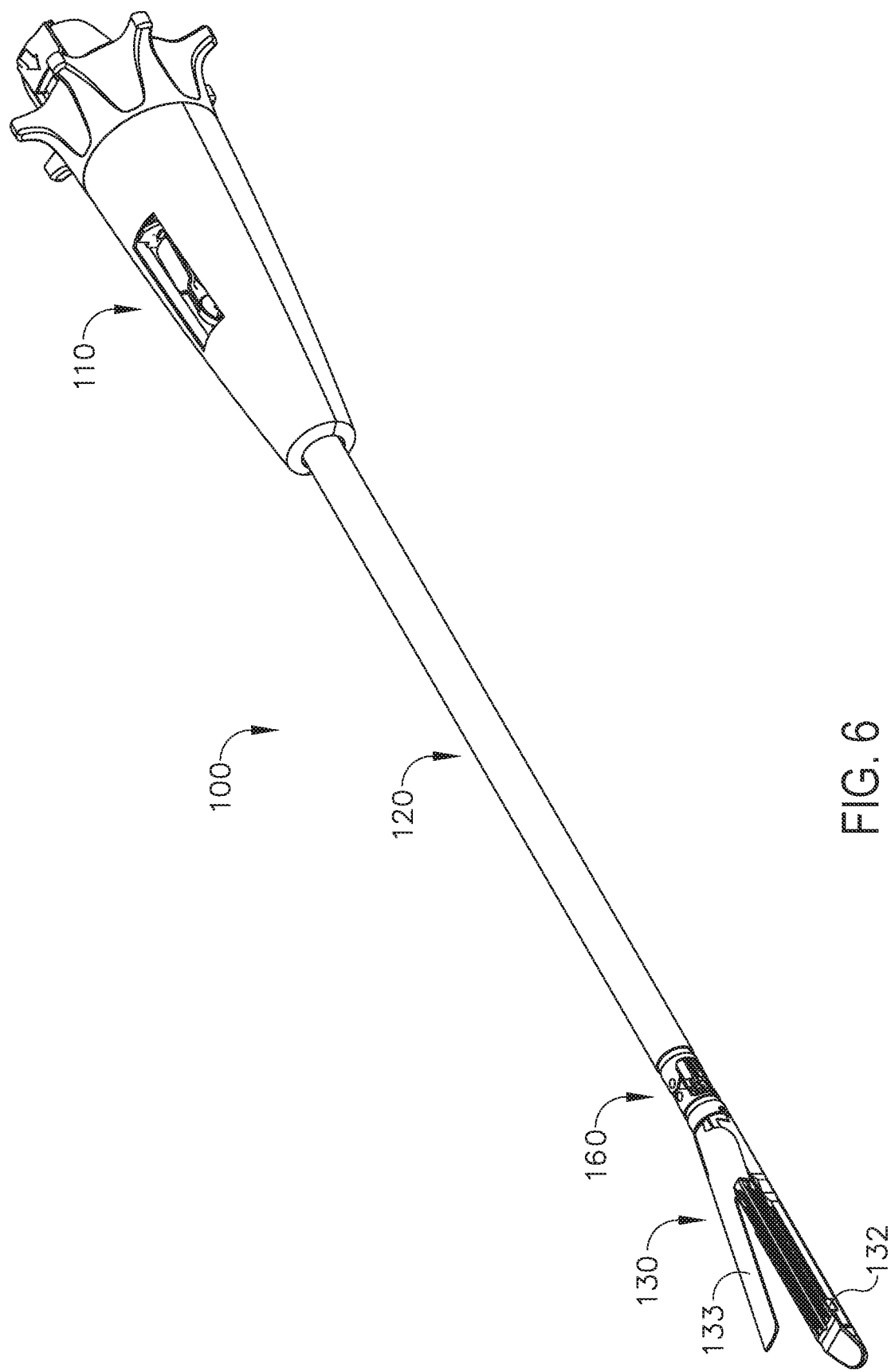
FIG. 6 is a perspective view of a shaft assembly in accordance with at least one embodiment.
Figure 7:
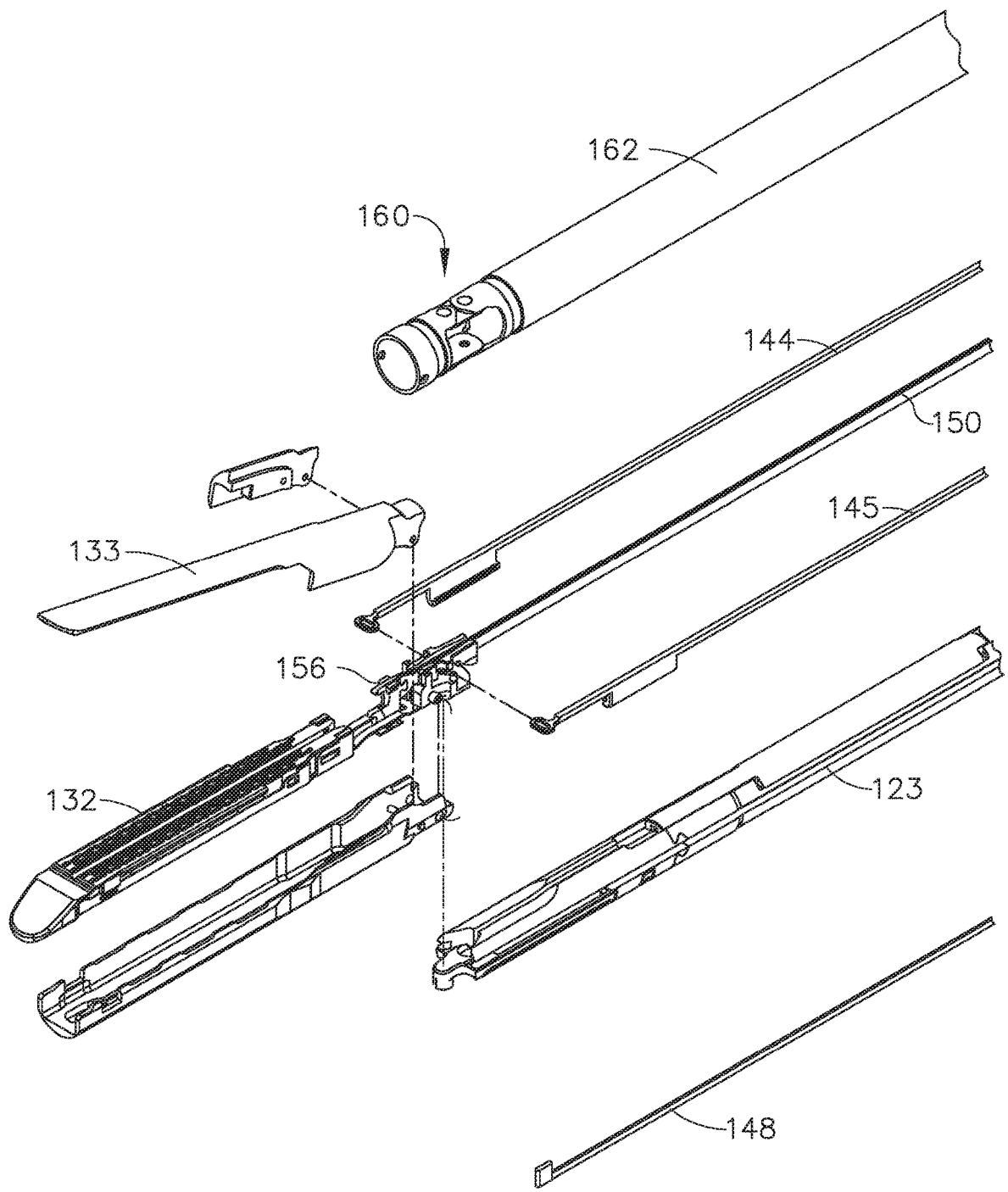
FIG. 7 is an exploded view of a distal end of the shaft assembly of FIG. 6.

A shaft assembly 100 is illustrated in FIGS. 6 and 7. The shaft assembly 100 comprises an attachment portion 110, a shaft 120 extending distally from the attachment portion 110, and an end effector 130 attached to the shaft 120. The shaft assembly 100 is configured to clamp, staple, and cut tissue. The attachment portion 110 is configured to be attached to a handle of a surgical instrument and/or the arm of a surgical robot, for example.

Referring to FIG. 7, the shaft assembly 100 comprises cooperating articulation rods 144, 145 configured to articulate the end effector 130 relative to the shaft 120 about an articulation joint 160. The shaft assembly 100 further comprises an articulation lock bar 148, an outer shaft tube 162, and a spine portion 123.

Referring to FIG. 7, the shaft assembly 100 comprises a firing shaft 150 including a firing member 156 attached to a distal end of the firing shaft 150. The firing member 156 comprises upper camming flanges configured to engage an anvil jaw 133 and lower camming members configured to engage a cartridge jaw 132. The firing shaft 150 is configured to be advanced distally through a closure stroke to clamp the anvil jaw 133 relative to the cartridge jaw 132 with the camming members. Further advancement of the firing shaft 150 through a firing stroke is configured to advance the firing member 156 through the cartridge jaw 132 to deploy staples from the cartridge jaw 132 and cut tissue during the firing stroke. More details of the shaft assembly 100 can be found in U.S. patent application Ser. No. 15/385,887 entitled METHOD FOR ATTACHING A SHAFT ASSEMBLY TO A SURGICAL INSTRUMENT AND, ALTERNATIVELY, TO A SURGICAL ROBOT, which is incorporated by reference in its entirety.

Figure 8:
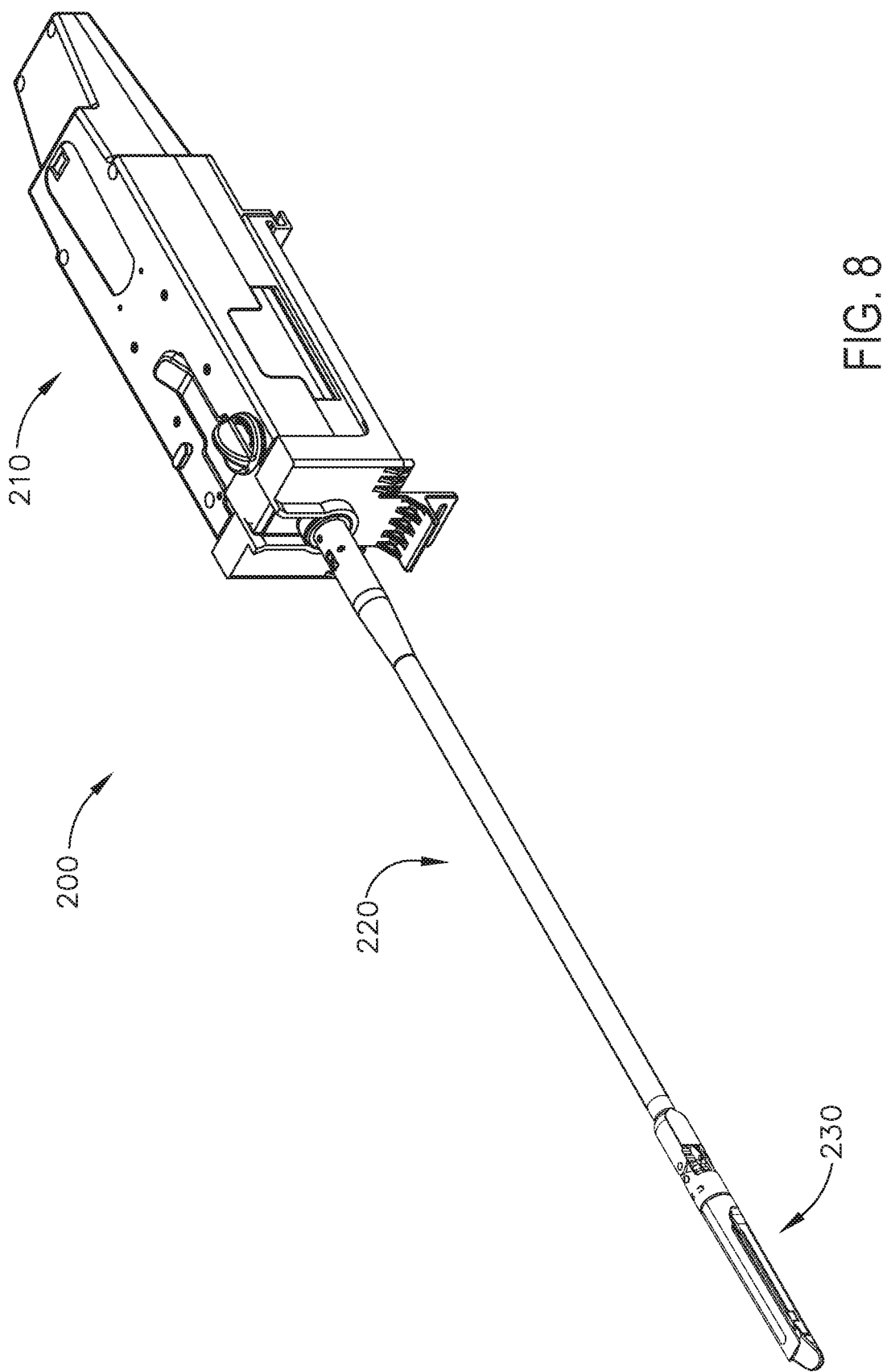
FIG. 8 is a perspective view of a surgical instrument assembly comprising a proximal control interface, a shaft assembly, and an end effector assembly.
Figure 9:
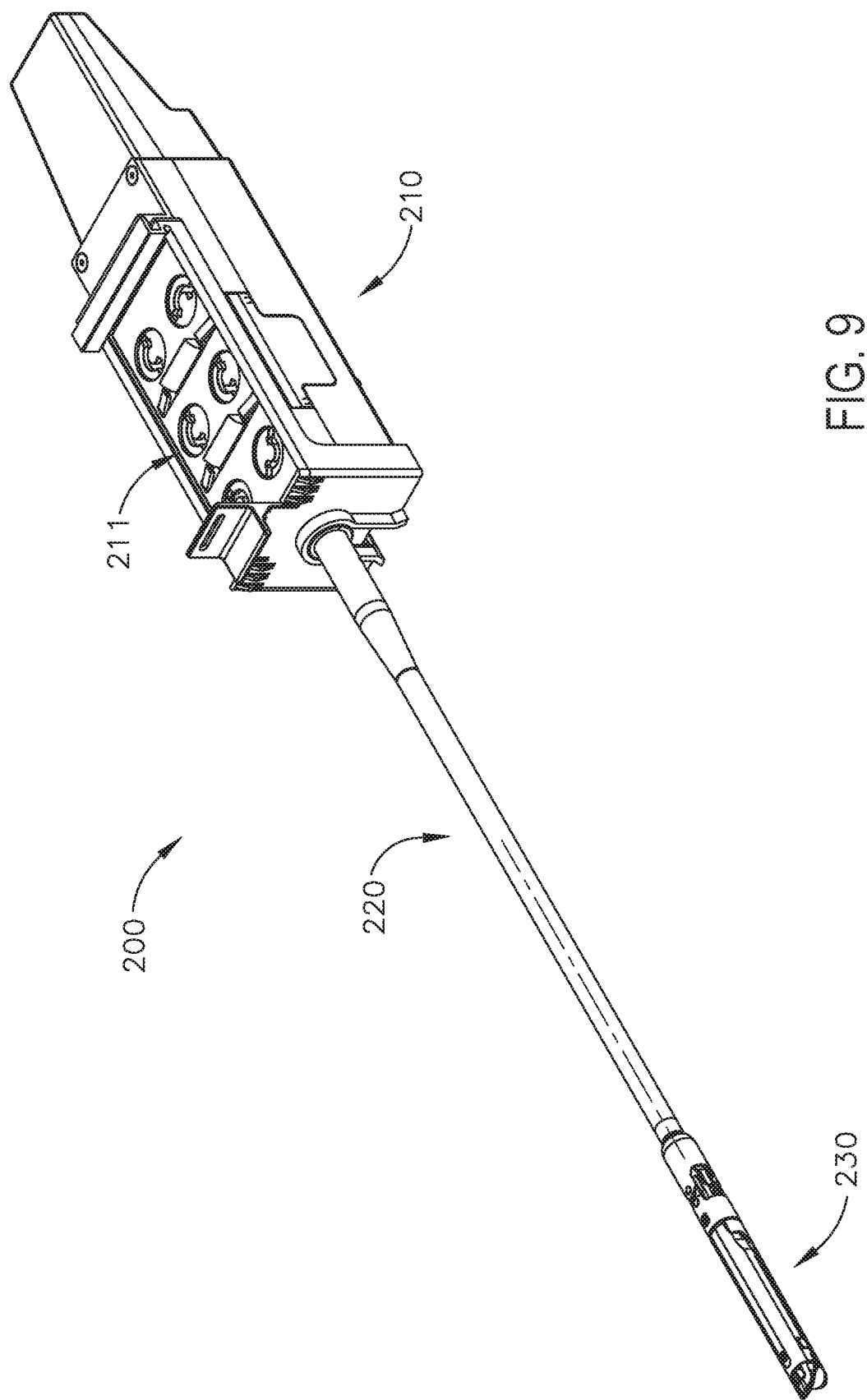
FIG. 9 is a bottom perspective view of the surgical instrument assembly of FIG. 8.

FIGS. 8 and 9 depict a surgical instrument assembly 200 configured to be used with a surgical robot. The surgical instrument assembly 200 is configured to staple and cut tissue, although the surgical instrument assembly 200 could be adapted to treat tissue in any suitable way, such as by applying heat energy, electrical energy, and/or vibrations to the tissue, for example. The surgical instrument assembly 200 comprises a proximal control interface 210 configured to be coupled to a robotic arm of a surgical robot and a shaft assembly 220 configured to be attached to the proximal control interface 210. The shaft assembly 220 comprises an end effector 230 configured to clamp, cut, and staple tissue. The proximal control interface 210 comprises a plurality of drive discs 211, each for actuating one or more functions of the surgical instrument assembly 200. Each drive disc 211 can be independently driven and/or cooperatively driven with one or more other drive discs 211 by one or more motors of the surgical robot and/or robotic arm of the surgical robot. More details about the surgical instrument assembly 200 can be found in U.S. patent application Ser. No. 15/847,297, entitled SURGICAL INSTRUMENTS WITH DUAL ARTICULATION DRIVERS, which is incorporated by reference in its entirety.

Figure 10:
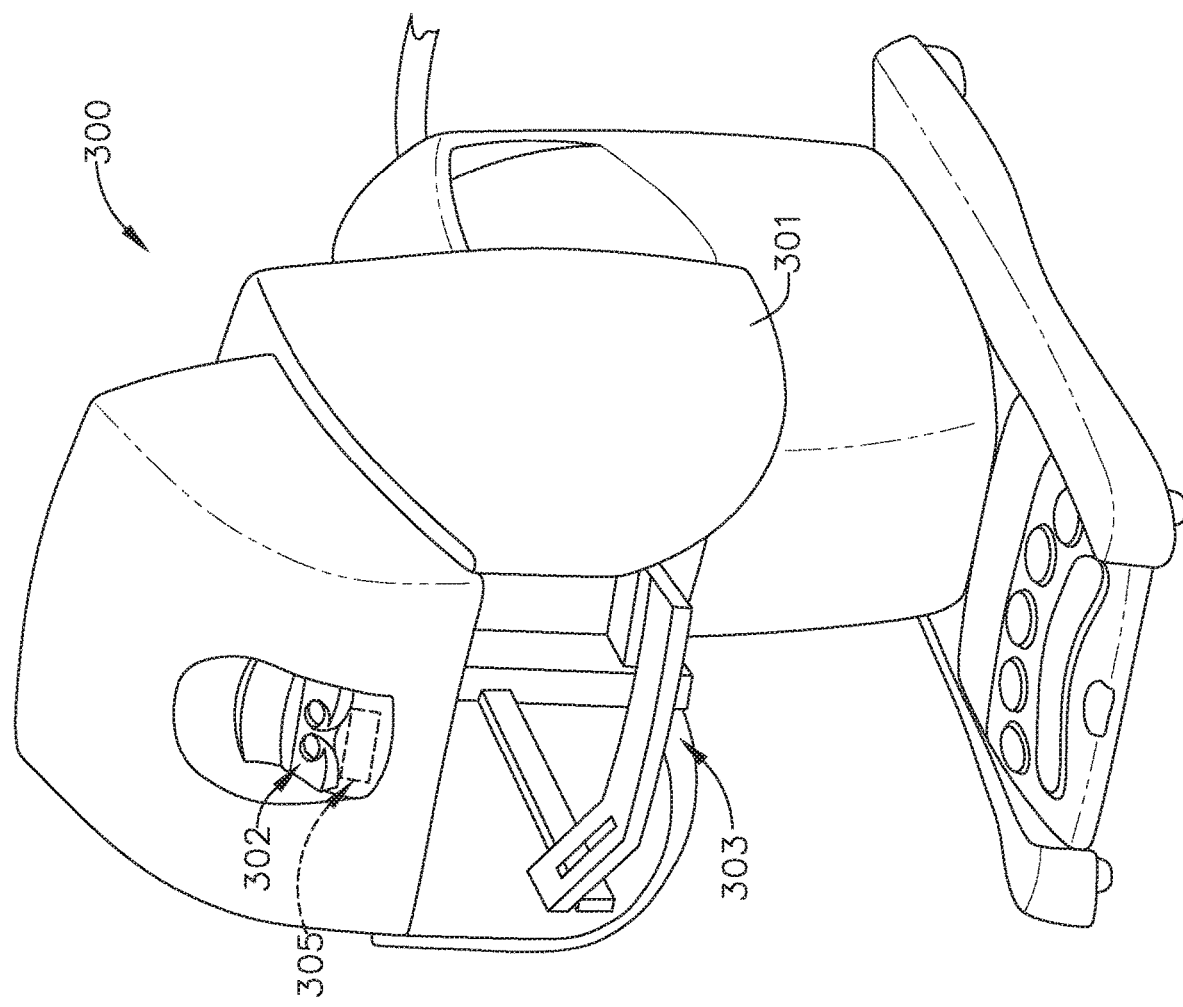
FIG. 10 is a perspective view of an example of one form of robotic controller according to one aspect of this disclosure.
Figure 11:
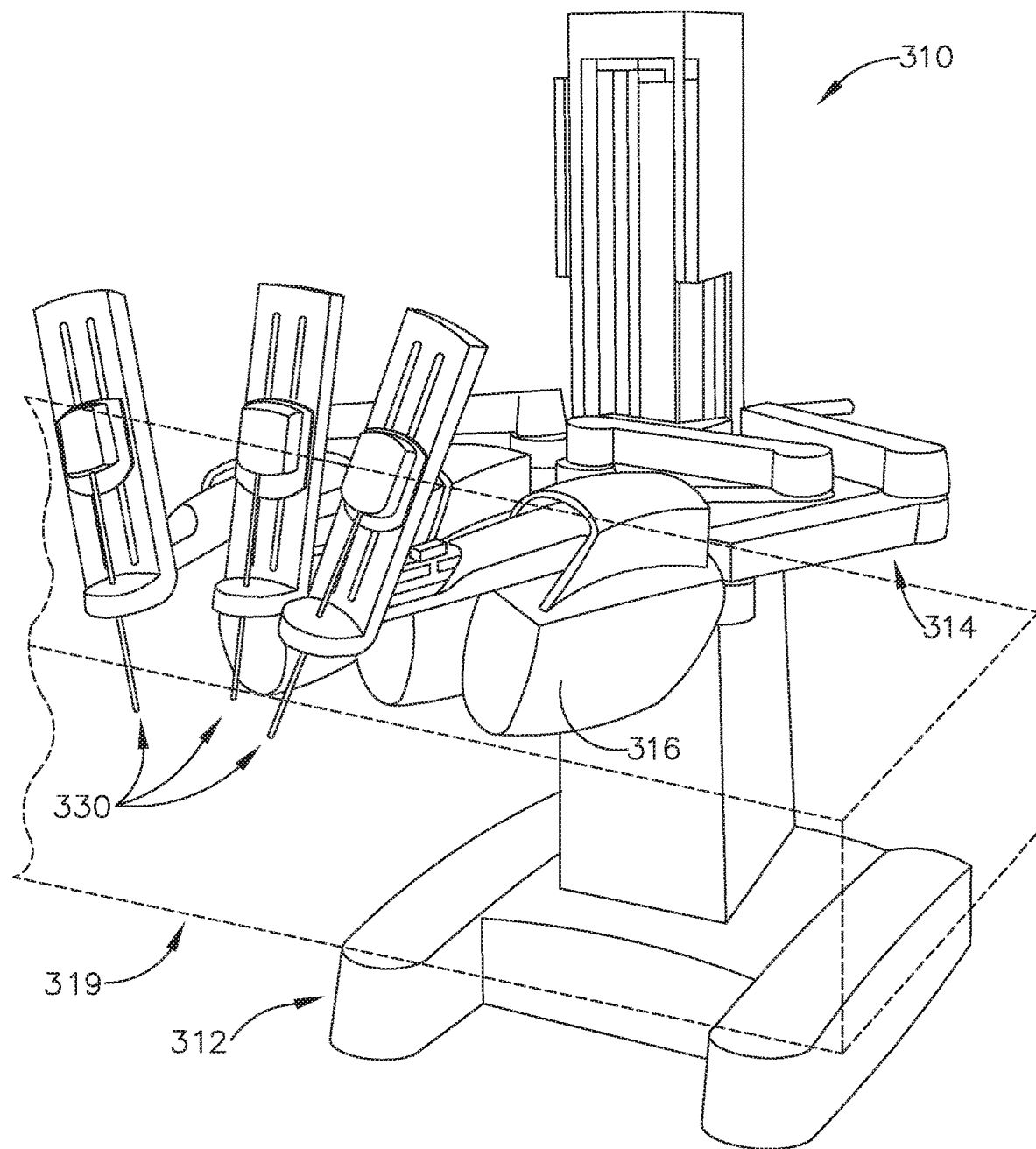
FIG. 11 is a perspective view of an example of one form of robotic surgical arm cart/manipulator of a robotic surgical system operably supporting a plurality of surgical tools according to one aspect of this disclosure.
Figure 12:
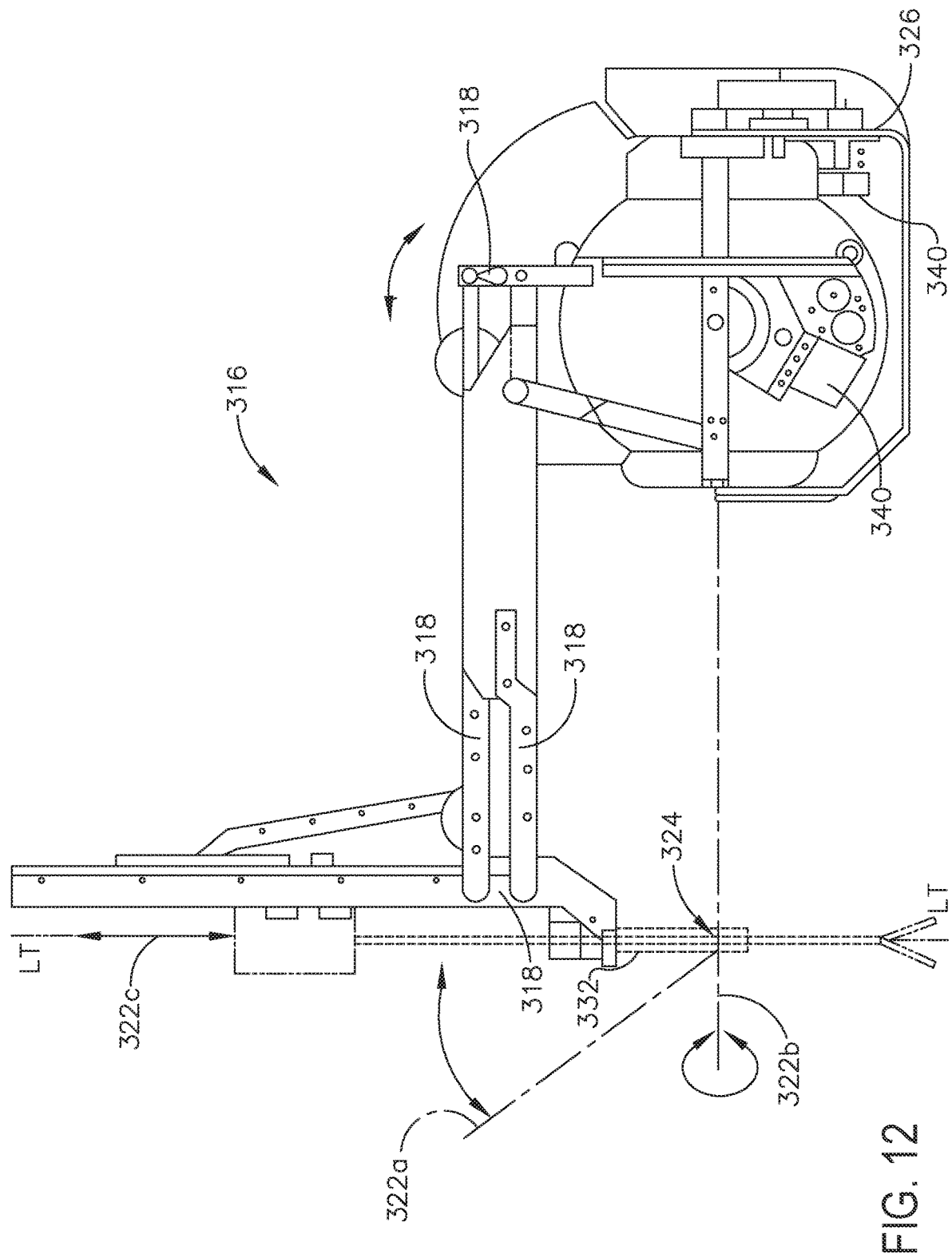
FIG. 12 is a side view of the robotic surgical arm cart/manipulator depicted in FIG. 11 according to one aspect of this disclosure.

Various embodiments disclosed herein may be employed in connection with a robotic system 300 of the type depicted in FIGS. 10-12, for example. FIG. 10 depicts one version of a master controller 301 that may be used in connection with a robotic arm slave cart 310 of the type depicted in FIG. 11. Master controller 301 and robotic arm slave cart 310, as well as their respective components and control systems are collectively referred to herein as a robotic system 300. Examples of such systems and devices are disclosed in U.S. Pat. No. 7,524,320, entitled MECHANICAL ACTUATOR INTERFACE SYSTEM FOR ROBOTIC SURGICAL TOOLS, as well as U.S. Pat. No. 9,072,535, entitled SURGICAL STAPLING INSTRUMENTS WITH ROTATABLE STAPLE DEPLOYMENT ARRANGEMENTS, which are each hereby incorporated by reference herein in their respective entireties. Thus, various details of such devices will not be described in detail herein beyond that which may be necessary to understand various embodiments and forms of the present disclosure. As is known, the master controller 301 generally includes master controllers (generally represented as 303 in FIG. 10) which are grasped by the surgeon and manipulated in space while the surgeon views the procedure via a stereo display 302. The master controllers 301 generally comprise manual input devices which preferably move with multiple degrees of freedom, and which often further have an actuatable handle for actuating tools (for example, for closing grasping jaws, applying an electrical potential to an electrode, or the like).

As can be seen in FIG. 11, in one form, the robotic arm cart 310 may be configured to actuate one or more surgical tools, generally designated as 330. Various robotic surgery systems and methods employing master controller and robotic arm cart arrangements are disclosed in U.S. Pat. No. 6,132,368, entitled MULTI-COMPONENT TELEPRESENCE SYSTEM AND METHOD the entire disclosure of which is hereby incorporated by reference herein. In various forms, the robotic arm cart 310 includes a base 312 from which, in the illustrated embodiment, surgical tools may be supported. In various forms, the surgical tool(s) may be supported by a series of manually articulatable linkages, generally referred to as set-up joints 314, and a robotic manipulator 316. In various embodiments, the linkage and joint arrangement may facilitate rotation of a surgical tool around a point in space, as more fully described in issued U.S. Pat. No. 5,817,084, entitled REMOTE CENTER POSITIONING DEVICE WITH FLEXIBLE DRIVE, the entire disclosure of which is hereby incorporated by reference herein. The parallelogram arrangement constrains rotation to pivoting about an axis 322a, sometimes called the pitch axis. The links supporting the parallelogram linkage are pivotally mounted to set-up joints 314 (FIG. 11) so that the surgical tool further rotates about an axis 322b, sometimes called the yaw axis. The pitch and yaw axes 322a, 322b intersect at the remote center 324, which is aligned along an elongate shaft of a surgical tool. The surgical tool may have further degrees of driven freedom as supported by manipulator 316, including sliding motion of the surgical tool along the longitudinal axis "LT-LT". As the surgical tool slides along the tool axis LT-LT relative to manipulator 316 (arrow 322c), remote center 324 remains fixed relative to base 326 of manipulator 316. Hence, the entire manipulator is generally moved to re-position remote center 324. Linkage 318 of manipulator 316 may be driven by a series of motors 340. These motors actively move linkage 318 in response to commands from a processor of a control system. The motors 340 may also be employed to manipulate the surgical tool. Alternative joint structures and set up arrangements are also contemplated. Examples of other joint and set up arrangements, for example, are disclosed in U.S. Pat. No. 5,878,193, entitled AUTOMATED ENDOSCOPE SYSTEM FOR OPTIMAL POSITIONING, the entire disclosure of which is hereby incorporated by reference herein. Additionally, while the data communication between a robotic component and the processor of the robotic surgical system is primarily described herein with reference to communication between the surgical tool and the master controller 301, it should be understood that similar communication may take place between circuitry of a manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like. In accordance with at least one aspect, various surgical instruments disclosed herein may be used in connection with other robotically-controlled or automated surgical systems and are not necessarily limited to use with the specific robotic system components shown in FIGS. 10-12 and described in the aforementioned references.

Figure 13:
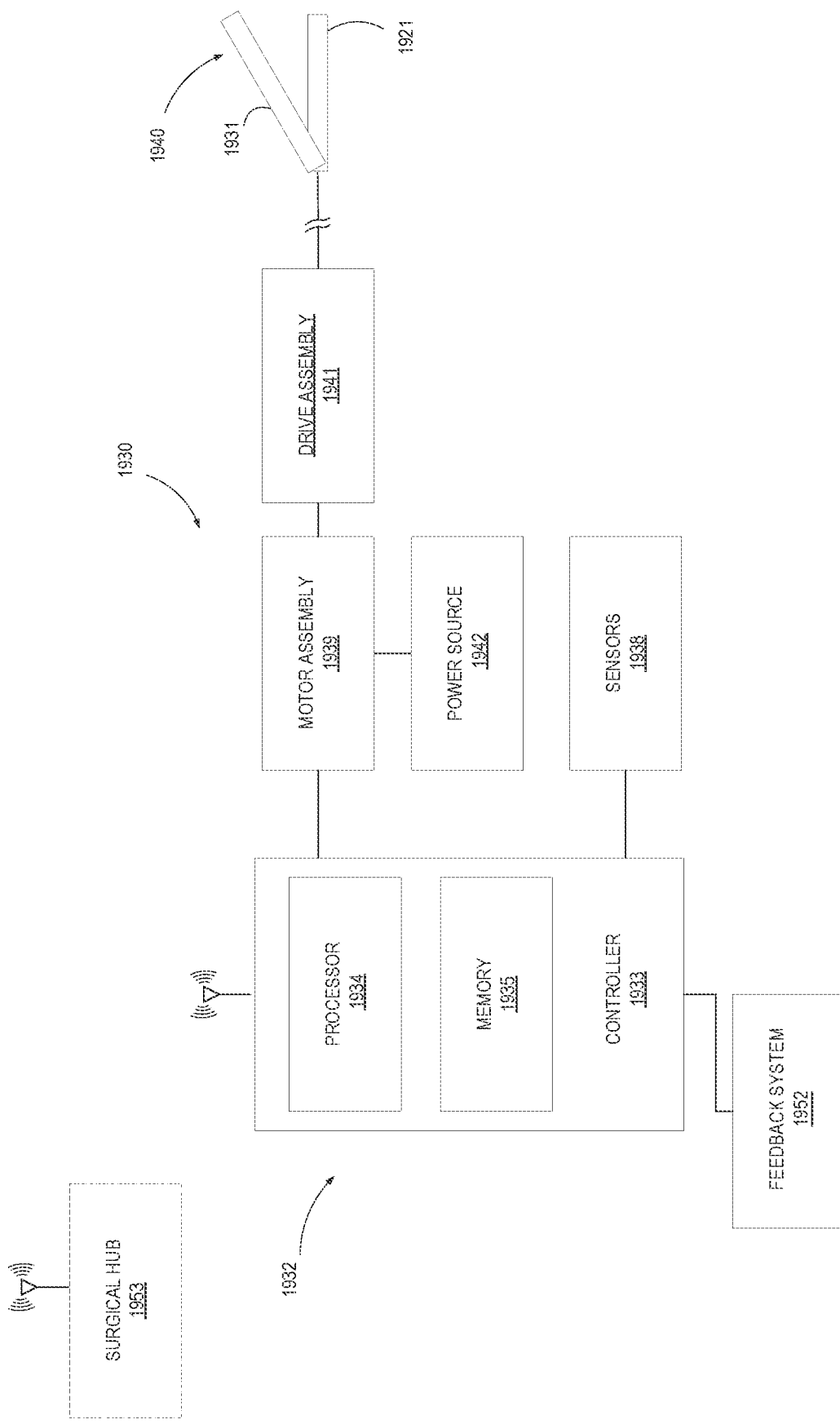
FIG. 13 illustrates a block diagram of a surgical system for use with one or more surgical instruments, tools, and/or robotic systems in accordance with one or more aspects of the present disclosure.

FIG. 13 illustrates a block diagram of a surgical system 1930 for use with one or more surgical instruments, tools, and/or robotic systems in accordance with one or more aspects of the present disclosure. The system 1930 includes a control circuit 1932. The control circuit 1932 includes a microcontroller 1933 comprising a processor 1934 and a storage medium such as, for example, a memory 1935.

A motor assembly 1939 includes one or more motors, driven by motor drivers. The motor assembly 1939 operably couples to a drive assembly 1941 to drive, or effect, one or more motions at an end effector 1940. The drive assembly 1941 may include any number of components suitable for transmitting motion to the end effector 1940 such as, for example, one or more linkages, bars, tubes, and/or cables, for example.

One or more of sensors 1938, for example, provide real-time feedback to the processor 1934 about one or more operational parameters monitored during a surgical procedure being performed by the surgical system 1930. The operational parameters can be associated with a user performing the surgical procedure, a tissue being treated, and/or one or more components of the surgical system 1930, for example. The sensor 1938 may comprise any suitable sensor, such as, for example, a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

Further to the above, in various arrangements, the sensors 1938 may comprise any suitable sensor for detecting one or more conditions at the end effector 1940 including, without limitation, a tissue thickness sensor such as a Hall Effect Sensor or a reed switch sensor, an optical sensor, a magneto-inductive sensor, a force sensor, a pressure sensor, a piezo-resistive film sensor, an ultrasonic sensor, an eddy current sensor, an accelerometer, a pulse oximetry sensor, a temperature sensor, a sensor configured to detect an electrical characteristic of a tissue path (such as capacitance or resistance), or any combination thereof. As another example, and without limitation, the sensors 1938 may include one or more sensors located at, or about, an articulation joint extending proximally from the end effector 1940. Such sensors may include, for example, a potentiometer, a capacitive sensor (slide potentiometer), piezo-resistive film sensor, a pressure sensor, a pressure sensor, or any other suitable sensor type. In some arrangements, the sensor 1938 may comprise a plurality of sensors located in multiple locations in the end effector 1940.

In certain aspects, the system 1930 includes a feedback system 1952 which includes one or more devices for providing a sensory feedback to a user. Such devices may comprise, for example, visual feedback devices (e.g., an LCD display screen, a touch screen, LED indicators), audio feedback devices (e.g., a speaker, a buzzer) or tactile feedback devices (e.g., haptic actuators).

The microcontroller 1933 may be programmed to perform various functions such as precise control over the speed and position of the drive assembly 1941. In one aspect, the microcontroller 1933 may be any single-core or multicore processor such as those known under the trade name ARM Cortex by Texas Instruments. In one aspect, the main microcontroller 1933 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

The microcontroller 1933 may be configured to compute a response in the software of the microcontroller 1933. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

The motor assembly 1939 includes one or more electric motors and one or more motor drivers. The electric motors can be in the form of a brushed direct current (DC) motor with a gearbox and mechanical links to the drive assembly 1941. In one aspect, a motor driver may be an A3941 available from Allegro Microsystems, Inc.

In various forms, the motor assembly 1939 includes a brushed DC driving motor having a maximum rotational speed of approximately 25,000 RPM. In other arrangements, the motor assembly 1939 may include a brushless motor, a cordless motor, a synchronous motor, a stepper motor, or any other suitable electric motor. The motor driver may comprise an H-bridge driver comprising field-effect transistors (FETs), for example.

The motor assembly 1939 can be powered by a power source 1942. In certain aspects, the power source 1942 includes one or more batteries which may include a number of battery cells connected in series that can be used as the power source to power the motor assembly 1939. In certain circumstances, the battery cells of the power assembly may be replaceable and/or rechargeable. In at least one example, the battery cells can be lithium-ion batteries which can be couplable to and separable from the power assembly.

Further to the above, the end effector 1940 includes a first jaw 1921 and a second jaw 1931. At least one of the first jaw 1921 and the second jaw 1931 is rotatable relative to the other during a closure motion that transitions the end effector 1940 from an open configuration toward a closed configuration. The closure motion may cause the jaws 1921, 1931 to grasp tissue therebetween. In certain arrangements, sensors, such as, for example, a strain gauge or a micro-strain gauge, are configured to measure one or more parameters of the end effector 1940, such as, for example, the amplitude of the strain exerted on the one or both of the jaws 1921, 1931 during a closure motion, which can be indicative of the closure forces applied to the jaws 1921, 1931. The measured strain is converted to a digital signal and provided to the processor 1934, for example. Alternatively, additionally, sensors such as, for example, a load sensor, can measure a closure force and/or a firing force applied to the jaws 1921, 1931.

In various arrangements, a current sensor can be employed to measure the current drawn by a motor of the motor assembly 1939. The force required to advance the drive assembly 1941 can correspond to the current drawn by the motor, for example. The measured force is converted to a digital signal and provided to the processor 1934.

In one form, strain gauge sensors can be used to measure the force applied to the tissue by the end effector 1940, for example. A strain gauge can be coupled to the end effector 1940 to measure the force on the tissue being treated by the end effector 1940. In one aspect, the strain gauge sensors can measure the amplitude or magnitude of the strain exerted on a jaw of an end effector 1940 during a closure motion which can be indicative of the tissue compression. The measured strain is converted to a digital signal and provided to a processor 1934.

The measurements of the tissue compression, the tissue thickness, and/or the force required to close the end effector on the tissue, as respectively measured by the sensors 1938 can be used by the microcontroller 1933 to characterize the selected position of one or more components of the drive assembly 1941 and/or the corresponding value of the speed of one or more components of the drive assembly 1941. In one instance, a memory (e.g. memory 1935) may store a technique, an equation, and/or a lookup table which can be employed by the microcontroller 1933 in the assessment.

The system 1930 may comprise wired or wireless communication circuits to communicate with surgical hubs (e.g. surgical hub 1953), communication hubs, and/or robotic surgical hubs, for example. Additional details about suitable interactions between a system 1930 and the surgical hub 1953 are disclosed in U.S. patent application Ser. No.

16/209,423 entitled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Application Publication No. 2019/0200981, the entire disclosure of which is incorporated by reference in its entirety herein.

In various aspects, the control circuit 1932 can be configured to implement various processes described herein. In certain aspects, the control circuit 1932 may comprise a microcontroller comprising one or more processors (e.g., microprocessor, microcontroller) coupled to at least one memory circuit. The memory circuit stores machine-executable instructions that, when executed by the processor, cause the processor to execute machine instructions to implement various processes described herein. The processor may be any one of a number of single-core or multicore processors known in the art. The memory circuit may comprise volatile and non-volatile storage media. The processor may include an instruction processing unit and an arithmetic unit. The instruction processing unit may be configured to receive instructions from the memory circuit of this disclosure.

Alternatively, in certain instances, the control circuit 1932 can be in the form of a combinational logic circuit configured to implement various processes described herein. The combinational logic circuit may comprise a finite state machine comprising a combinational logic configured to receive data, process the data by the combinational logic, and provide an output.

Alternatively, in certain instances, the control circuit 1932 can be in the form of a sequential logic circuit. The sequential logic circuit can be configured to implement various processes described herein. The sequential logic circuit may comprise a finite state machine. The sequential logic circuit may comprise a combinational logic, at least one memory circuit, and a clock, for example. The at least one memory circuit can store a current state of the finite state machine. In certain instances, the sequential logic circuit may be synchronous or asynchronous. In other instances, the control circuit 1932 may comprise a combination of a processor (e.g., processor 1934) and a finite state machine to implement various processes herein. In other aspects, the finite state machine may comprise a combination of a combinational logic circuit (and the sequential logic circuit, for example.

Figure 14:
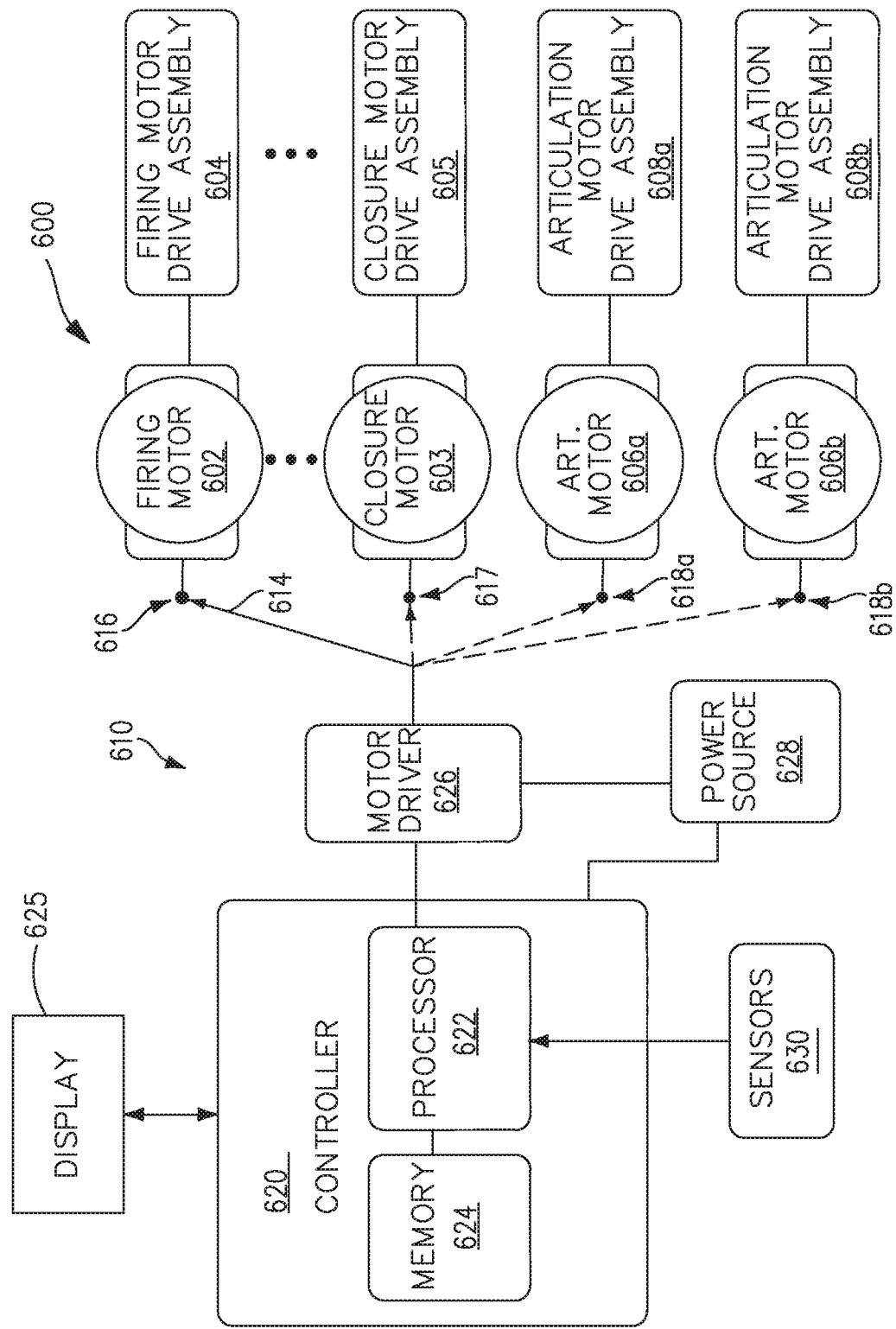
FIG. 14 illustrates a block diagram of a surgical system for use with one or more surgical instruments, tools, and/or robotic systems in accordance with one or more aspects of the present disclosure.

FIG. 14 illustrates a block diagram of a surgical system 600 for use with one or more surgical instruments, tools, and/or robotic systems in accordance with one or more aspects of the present disclosure. The surgical system 600 is similar in many respects to the surgical system 1930, which are not repeated herein at the same of detail for brevity. For example, like the surgical system 1930, the surgical system 600 includes a control circuit comprising a microcontroller 620 comprising a processor 622 and a memory 624, sensors 630, and a power source 628, which are similar, respectively, to the microcontroller 1933, the processor 1934, the memory 1935, and the power source 1942. Additionally, the surgical system 600 includes a plurality of motors and corresponding driving assemblies that can be activated to perform various functions.

In certain instances, a first motor can be activated to perform a first function, a second motor can be activated to perform a second function, a third motor can be activated to perform a third function, a fourth motor can be activated to perform a fourth function, and so on. In certain instances, the plurality of motors can be individually activated to cause firing, closure, and/or articulation motions in an end effector 1940, for example. The firing, closure, and/or articulation motions can be transmitted to the end effector 1940 through a shaft assembly, for example.

In certain instances, the system 600 may include a firing motor 602. The firing motor 602 may be operably coupled to a firing motor drive assembly 604 which can be configured to transmit firing motions, generated by the motor 602 to the end effector, in particular to displace the I-beam element. In certain instances, the firing motions generated by the motor 602 may cause the staples to be deployed from a staple cartridge into tissue captured by the end effector 1940 and/or the cutting edge of the I-beam element to be advanced to cut the captured tissue, for example. The I-beam element may be retracted by reversing the direction of the motor 602.

In certain instances, the system 600 may include a closure motor 603. The closure motor 603 may be operably coupled to a closure motor drive assembly 605 which can be configured to transmit closure motions, generated by the motor 603 to the end effector 1940, in particular to displace a closure tube to close an anvil and compress tissue between the anvil and the staple cartridge. The closure motions may cause the end effector 1940 to transition from an open configuration to an approximated configuration to grasp tissue, for example. The end effector 1940 may be transitioned to an open position by reversing the direction of the motor 603.

In certain instances, the system 600 may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to a shaft, for example.

As described above, the system 600 may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore, the closure motor 603 may be activated simultaneously with the firing motor 602 to cause the closure tube and the I-beam element to advance distally as described in more detail hereinbelow.

In certain instances, the system 600 may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 14, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 14, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610.

In certain instances, the memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

In certain instances, one or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the I-beam of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

In various instances, one or more mechanical outputs of a motor system including a motor and a drive train connected to the motor can be used as an input to a motor control circuit which controls the motor to increase the efficiency of the motor system. In at least one instance, the drive train includes a closure member coupled to a motor configured to clamp tissue with an end effector. In at least one instance, the drive train includes a firing member coupled to a motor configured to move a firing member through a firing stroke. In at least one instance, the firing stroke includes a staple firing stroke. In at least one instance, the firing stroke includes a portion of which where the firing member clamps tissue with jaws of the end effector and another portion of which where the firing member deploys staples from the end effector to staple and cut the tissue clamped with the end effector.

Mechanical outputs of the motor can include any suitable mechanical output. For example, mechanical outputs may include the actual speed of the motor, the actual displacement of the motor (measured with an encoder, for example), and/or the amount of elapsed time the motor runs. Further to the above, mechanical outputs may include heat generated by the motor and/or forces generated with the drive train, for example. Such outputs can be measured in any suitable fashion directly and/or indirectly.

In various instances, a motor system including a motor and a drive train connected to the motor may be underutilized (the motor speed can be increased without fear of overstraining the motor system, for example), over utilized (the motor is running at a speed which may be close to, or is already, overstraining the motor system, for example), and/or adequately utilized (the motor is running at a speed where the motor system is not overstrained nor is there room for a speed increase of the motor, for example). In other words, the motor system is operating below maximum, or optimal, capacity, motor system is operating at maximum capacity, and/or the motor system is operating beyond its maximum capacity.

Depending on the degree of utilization of the motor system, adjustments can be made by a motor control circuit so as to increase the efficiency of the motor system, for example. Such adjustments can include dynamic adjustments of the motor. In at least one instance, the adjustments include dynamic control of the speed of the motor. Overstraining the motor system may include running a motor at a duty cycle outside of a threshold duty cycle range which may cause a motor to fail sooner than expected, for example. In various instances, the capacity of the motor system can be measured to determine the degree of utilization of the motor system. Duty cycles of pulse width modulation (PWM) motor control can differ in width percentage and magnitude, for example.

In at least one instance, a motor control circuit is configured to interrogate and/or determine the relative capacity of a motor system. In at least one instance, interrogation of the relative capacity of the motor system includes monitoring a parameter of one or more components of the drive train and/or the motor. The relative capacity of the motor system may be monitored at any suitable time, for example. In at least one instance, the relative capacity of the motor system is automatically monitored prior to a clamping stroke, during the clamping stroke, after the clamping stroke but before a staple firing stroke, during the staple firing stroke, near an end of the staple firing stroke, and/or after the end of the staple firing stroke. In at least one instance, interrogation of the relative capacity of the motor system is manually initiated by a user of the instrument. Relative capacity of the motor system can be also be referred to as the unused, or available, capacity of the motor and/or motor system relative to a maximum capacity, for example.

Adjustments of the motor system can be made by a motor control circuit at any suitable time. For example, adjustments of the motor system can be made simultaneously, and/or at least substantially simultaneously, when the motor system is interrogated and the relative capacity of the motor system is determined. Interrogation of the motor system may be referred to as the interrogation action, a sensory action, and/or a micro-step. These actions can also be referred to as steps such as, for example, interrogation steps and/or sensory steps. In at least one instance, adjustments of the motor system can be made after a predetermined set time interval measured from the time of the interrogation action and/or after the completion of the interrogation action, for example.

In at least one instance, the relative capacity of a motor system is repeatedly monitored, and/or measured, over a period of time at a desired frequency. Further to the above, adjustments can be made to the motor system based on the measured relative capacity. Such adjustments can be made with the same and/or different frequency as the frequency at which the relative capacity of the motor system is measured. Each frequency can be adjusted automatically and/or manually to better suit different scenarios, for example. For example, the frequency at which the relative capacity of a motor system which clamps a jaw of an end effector is measured may be higher than the frequency at which a motor system which deploys a firing member or vice versa. In at least one instance, the frequency at which the relative capacity of a motor system which deploys a firing member is monitored is higher than the corresponding frequency at which adjustments are made to the same motor system. Such an arrangement can increase the stability of the motor system during the staple firing stroke, for example.

Various types of adjustments can be made upon determining the relative capacity of the motor system. For example, the motor system can be paused, a lockout can be activated, the motor can be slowed down, the motor can be sped up, the speed of the motor can be kept the same, and/or another interrogation action can be performed to verify the previously determined relative capacity.

In at least one instance, the speed of the motor is increased incrementally at a frequency in an effort to maximize the operational efficiency of the motor system, for example. With each incremental speed increase, the relative capacity of the motor system is determined by measuring an actual mechanical output of the motor system such as, for example, the actual speed of the motor. The actual speed of the motor can be used to determine if the motor system is operating at a predicted, or anticipated, state in response to each incremental increase in motor speed. For example, if the actual speed of the motor is as anticipated after an incremental speed increase is made to the motor, it may be determined that the motor system is operating at or below its maximum, or optimal, capacity. In such an instance, the speed of the motor is, again, increased incrementally and the relative capacity of the motor system is, again, determined. After one or more incremental speed increases, the actual speed of the motor may be not as anticipated and it may be determined that the motor system is operating beyond its maximum capacity. In such an instance, a variety of things can happen, discussed in greater detail below.

If the motor system is determined to be operating at or beyond maximum, or optimal, capacity after an incremental speed increase, a user may be alerted, the motor system can be adjusted in any suitable manner, and/or no adjustments are made to the motor system. In at least one instance, the speed of the motor is reduced back to its previous speed. For example, if the motor undergoes five incremental speed increases from a starting speed and at the fifth incremental speed increase it is determined that the motor system is operating beyond its maximum capacity, the speed of the motor can be reverted back to the speed set for the fourth incremental speed increase. In at least one instance, the reversion speed is equal to the speed set for the fourth incremental speed increase. In at least one instance, the reversion speed is a percentage of the speed set for the fourth incremental speed increase so as to not operate the motor system near its maximum capacity, but, operate the motor system a percentage below maximum capacity. Such an arrangement may increase the longevity of the motor system, for example, by rarely operating the motor system at its maximum capacity. In at least one instance, the maximum capacity is predefined below an actual maximum capacity, such as absolute mechanical capacity, for example, of the motor system. The actual maximum capacity of the motor system may be manufacturer-suggested, for instance.

In various instances, the incremental speed increases are not noticeable, or imperceptible, to a user. Such imperceptibility can be measured by vibration yield of the surgical instrument system, for example, being below a predefined perceptible threshold, for example. In at least one instance, a time period with which a speed increase is executed is below a perceptible time threshold so as to reduce the likelihood of a user noticing the speed increase. In at least one instance, the frequency at which the speed is increased is high but the magnitude of each incremental speed increase is low compared to the actual speed of the motor. Thus, the motor system is capable of constantly adjusting the speed of the motor to improve efficiency and/or maintain maximum efficiency, for example, while not effecting the user's experience. Such an arrangement may prevent jerkiness of a system which increases the speed of a motor substantially during a staple firing stroke, for example.

In at least one instance, after it is determined that the motor system is operating at maximum, or optimal, capacity, a delay is employed so as to not immediately reinitiate the interrogation of the motor system. In at least one instance, a delay is not employed and the motor system is constantly interrogated regardless of the adjustments made to the motor.

Interrogating the relative capacity of the motor system may also be referred to as sensing the relative capacity of the motor system. One or more sensory actions can be performed to determine when the speed of the motor can be increased, for example.

Figure 15:
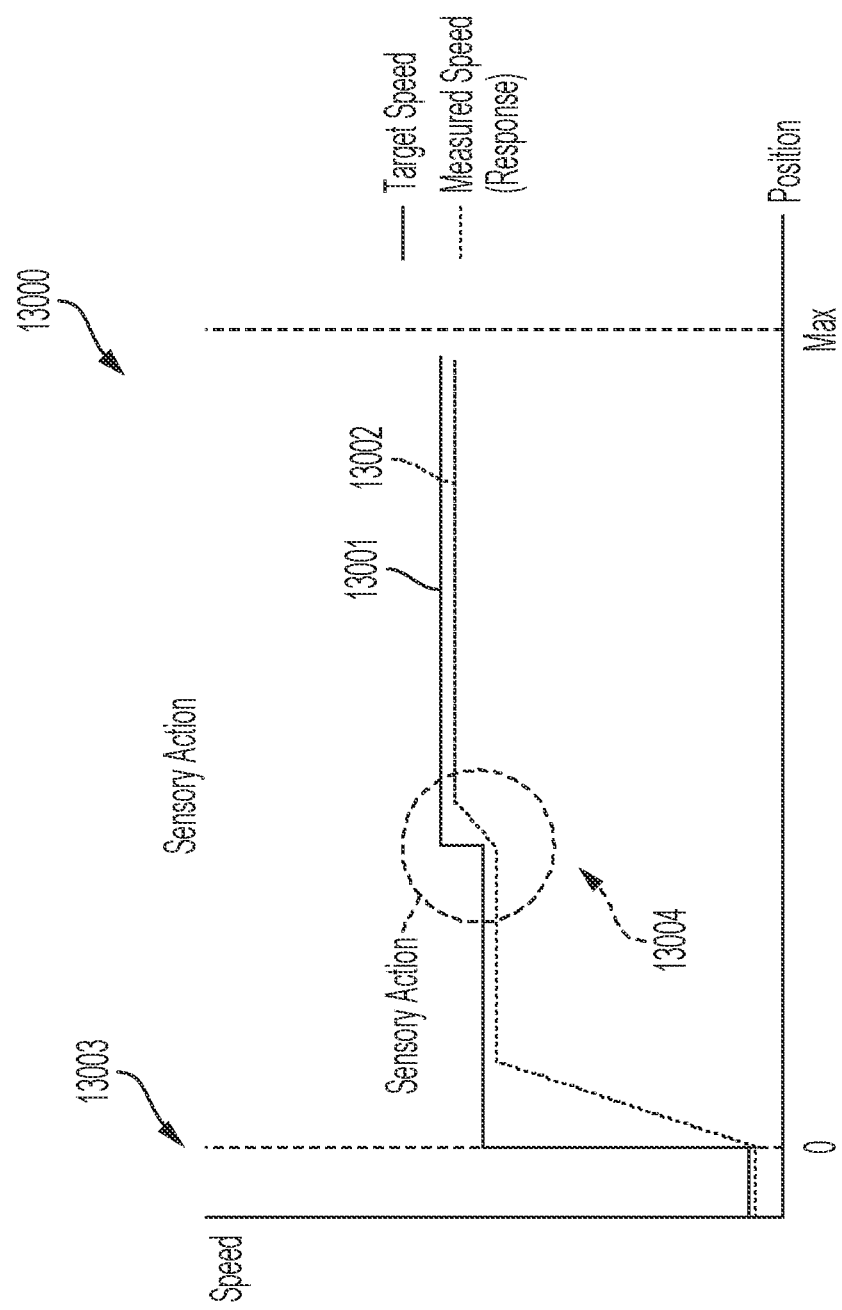
FIG. 15 is a graph depicting a firing stroke performed by a motor system that includes a motor, a drive train, and a motor control circuit, wherein the motor control circuit performs a sensory, or interrogation, action during a firing stroke in order to determine if the speed of the motor is capable of being increased to a target speed.

FIG. 15 is a graph 13000 depicting an example of a sensory action 13004 performed in order to determine if the speed of the motor is capable of being increased. As can be seen in the graph 13000, the target speed 13001 is increased at the beginning of the stroke 13003 (position 0) to a first target, or set, speed. In response, the measured speed 13002 increases until the motor reaches a first measured speed. In at least one instance, the first measured speed is as anticipated and thus a sensory action can be performed. The first target speed and the first measured speed may or may not be identical. At the sensory action 13004, the speed of the motor is increased a predetermined amount to a second target speed. In response, the measured speed 13002 gradually increases to a second measured speed. The measured, or actual, speed 13002 may vary due to a variety of factors such as, for example, motor performance, type of tissue encountered, and/or drive train backlash. At such point, based on the system response (actual measured speed of the motor relative to the second target speed, for example) to the sensory action 13004, the second target speed is maintained to run the motor at the second target speed. It may be determined that additional, or excess, capacity was, in fact, present based on the difference, or magnitude of deviation, between the actual measured speed of the motor relative to the second target speed. In at least one instance, the target speed may be reverted back to the first target speed if excess capacity is not available.

In various instances, a sensory action leads into a permanent action where a final, or optimal, speed is set by a control circuit. In other words, the increase in speed of the motor performed during the interrogation action of the motor system is maintained for the rest of a stroke or, in the case where a target speed, or predetermined percentage of the target speed, is not attained upon the performance of the sensory action, it is determined that additional capacity is not available and the speed of the motor is reverted back to the speed at which the motor was operating prior to the speed increase.

Figure 16:
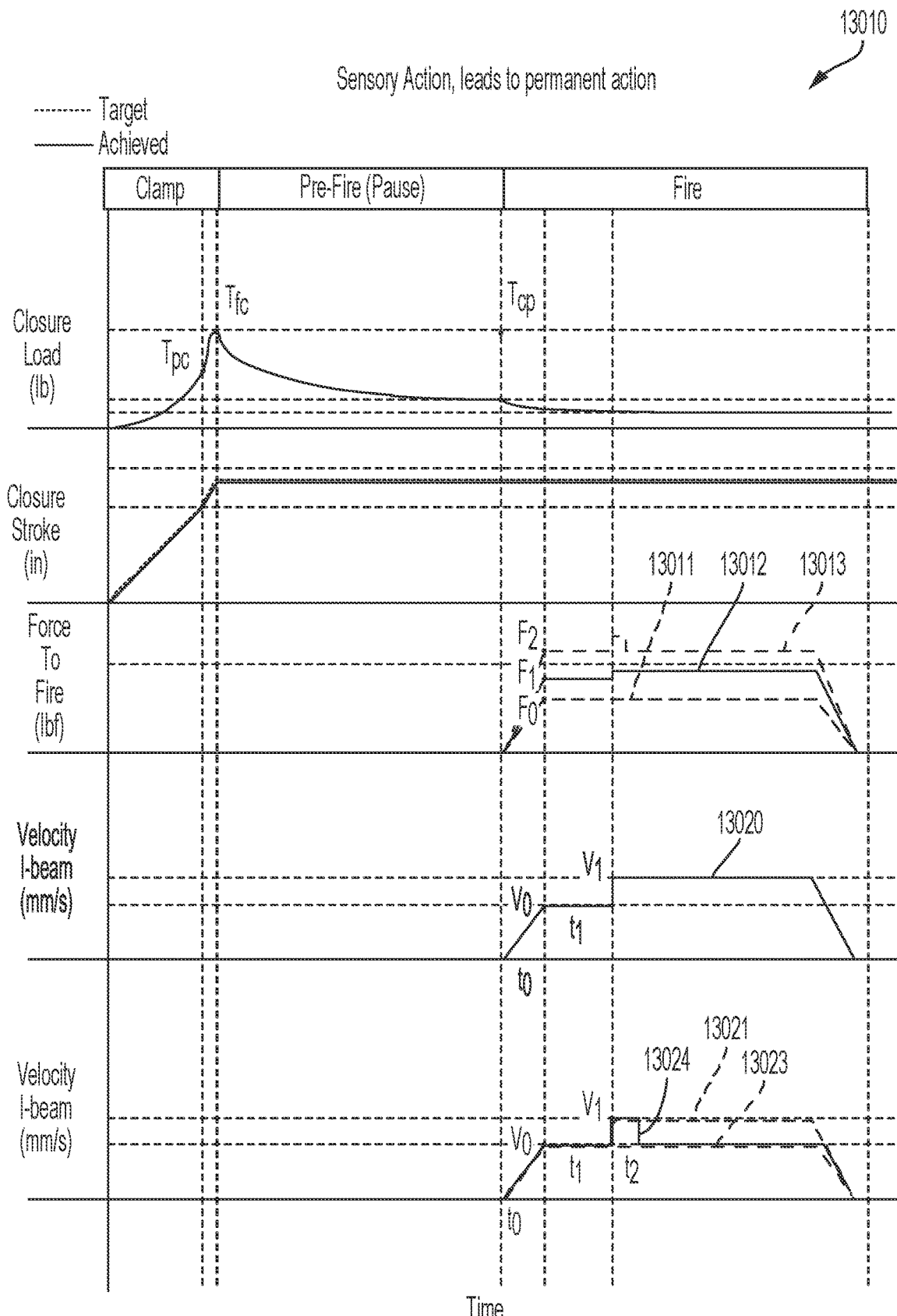
FIG. 16 is a graph depicting several firing strokes performed by a motor system that includes a motor, a drive train, and a motor control circuit, wherein different sensory actions are performed with different outcomes.

FIG. 16 is a graph 13010 depicting different staple firing strokes 13011, 13012, and 13013 and the results of interrogating a motor system performing the different staple firing strokes 13011, 13012, and 13013 in an effort to determine the relative capacity of the motor system. Closure load (the load experienced by clamping the jaws) and stroke position (the position of the firing member throughout the closure stroke and firing stroke) are also depicted. The force required to fire a firing member, for example, is also depicted for each staple firing stroke 13011, 13012, and 13013. The initial force to fire for stroke 13011 is F0, the initial force to fire for stroke 13012 is F1, and the initial force to fire for stroke 13013 is F2. As can also be seen in FIG. 16, various events corresponding to a surgical stapling instrument, for example, are also illustrated on the graph 13010: the clamping time period (with a partial clamp indicator Tpc and a fully clamp indicator Tfc), the pre-fire, or pause, time period, and the fire time period.

In addition to the above, the actual speed, or velocity, of the i-beam, or firing member, for example is depicted for each staple firing stroke 13011, 13012, and 13013 as well as the target speed 13020 utilized in the sensory action for each firing stroke. As can be seen in the graph 13010, the target speed 13020 increases from zero to V0 in the beginning of the firing stroke by a motor control circuit, for example. Speed V0 can be used to apply full clamping pressure to the jaws of an end effector with an i-beam, for example. After time t1, a sensory action is performed by the motor control circuit and an attempt is made to increase the speed of the motor to V1 for each staple firing stroke 13011, 13012, and 13013.

In response to the speed increase of the motor during staple firing stroke 13011, the force to fire is relatively low and, thus, the actual speed 13021 of the motor remains at or within an acceptable percentage of the target speed of V1. The actual speed 13021 is measured and, once it is determined that the actual speed 13021 of the motor is at or within the acceptable percentage of the target speed of V1, a motor control circuit maintains the target speed of V1 through the rest of the staple firing stroke 13011. In response to the speed increase of the motor during staple firing stroke 13012 where an increased force to fire is experienced in addition to a mid-stroke increase of the force to fire, the actual speed of the motor remains within an acceptable level relative to the target speed V1. For clarity, the actual speed of the staple firing stroke 13012 is represented as being identical to the actual speed 13021. In such an instance, the motor control circuit maintains the target speed of V1 through the rest of the staple firing stroke 13012. In response to the speed increase of the motor during staple firing stroke 13013 where the force to fire is relatively high to begin with and a larger mid-stroke increase of the force to fire is experienced, the actual speed 13023 of the motor is not able to achieve the target speed of V1 nor is the actual speed 13023 of the motor able to achieve a speed within the acceptable percentage of the target speed of V1. In such an instance, the motor control circuit reverts the target speed of the motor back to target speed V0 after a time period t2. In at least one instance, the motor control circuit reverts the target speed of the motor back to a predetermined percentage of target speed V0 and/or a predetermined magnitude of speed above and/or below the target speed V0. In at least one instance, the magnitude of the adjustment is based on the magnitude of the deviation between the actual measured speed and the target speed.

The sensory action performed during the staple firing strokes 13011, 13012, and 13013 includes a time period of t2. In other words, target speed V1 may be held at V1 for the time period t2. The time period t2 may be any suitable time period.

In various instances, the sensory action occurs before, or prior to, a reaction, or permanent action, for example. In other words, the speed of the motor is increased, the relative capacity of the motor system is determined, the speed of the motor is reverted back to its original speed and, later during the staple firing stroke, the speed of the motor is increased in response to the determined relative capacity of the motor system attained during the sensory action. In at least one instance, a plurality of sensory actions are performed prior to a reaction.

Figure 17:
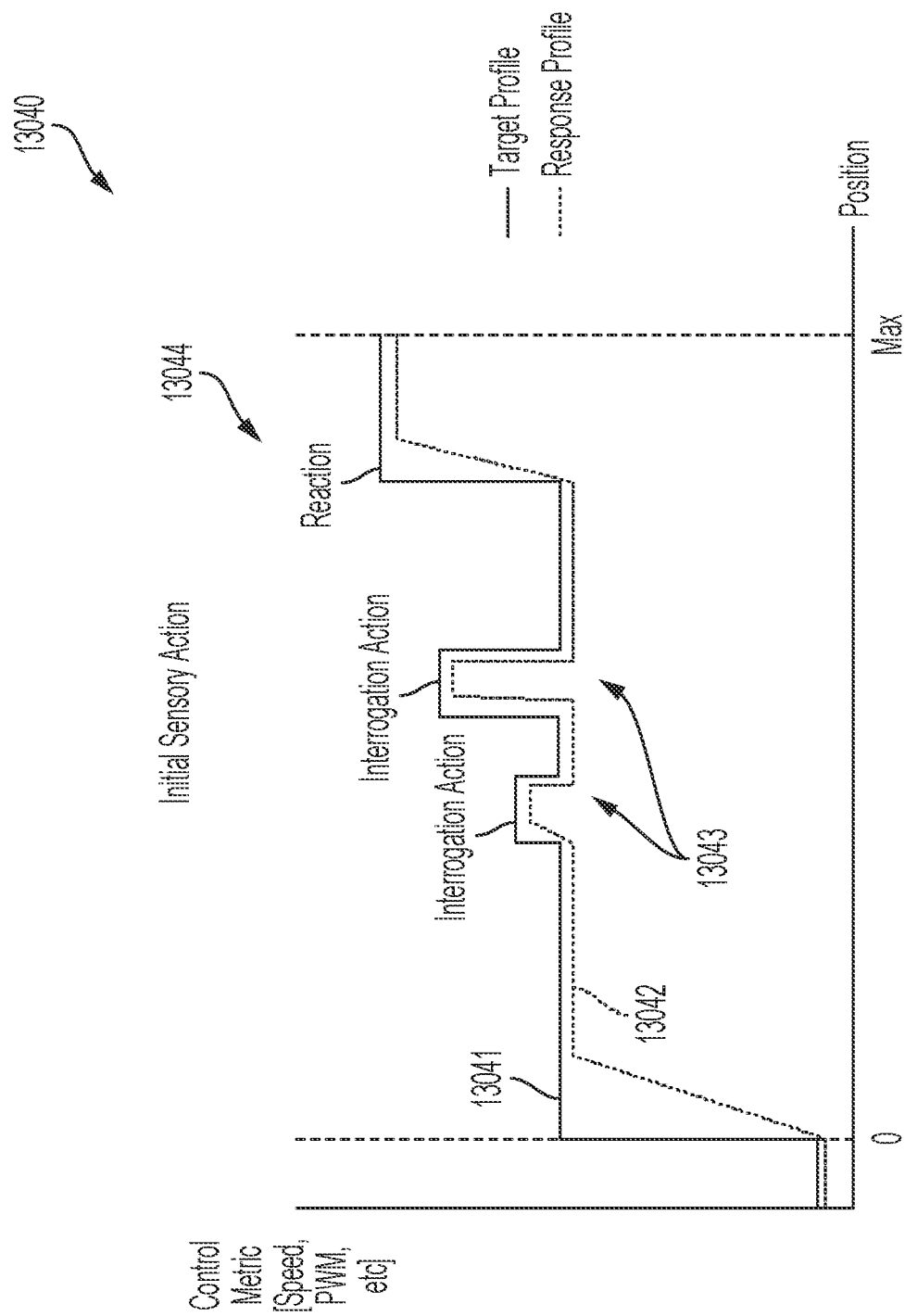
FIG. 17 is a graph depicting a firing stroke performed by a motor system that includes a motor, a drive train, and a motor control circuit, wherein the motor control circuit performs multiple discrete sensory actions and, in response to the sensory actions, performs a reaction a period of time after the completion of the sensory actions.

FIG. 17 is a graph 13040 depicts actual speed 13042 of a staple firing stroke relative to a target speed 13041 of the staple firing stroke. The relative capacity of the motor system is interrogated during interrogation actions 13043. The interrogation actions 13043 occur prior to a reaction, or optimized action, 13044. The interrogation actions 13043 each include an increase in motor speed. In at least one instance, the interrogation actions 13043 include different target speeds. In at least one instance, the target speed of subsequent interrogation actions 13043 is set based on the response, or determined relative capacity, of the motor system during previous interrogation actions 13043. During the staple firing stroke, the target speed is increased after the completion of one or more interrogation actions during the reaction, or optimized action, 13044. In at least one instance, a period of time elapses after the last interrogation action 13043 before the target speed of the motor is increased during the reaction action 13044.

In at least one instance, a user is alerted prior to a reaction, or optimized action, being performed. For example, a user may be notified through a user interface that the motor system is operating below maximum capacity after a motor control circuit performs one or more unnoticeable interrogation actions. A user may then be able to select whether or not to perform a recommended reaction and/or modify the recommended reaction, for example.

Figure 18:
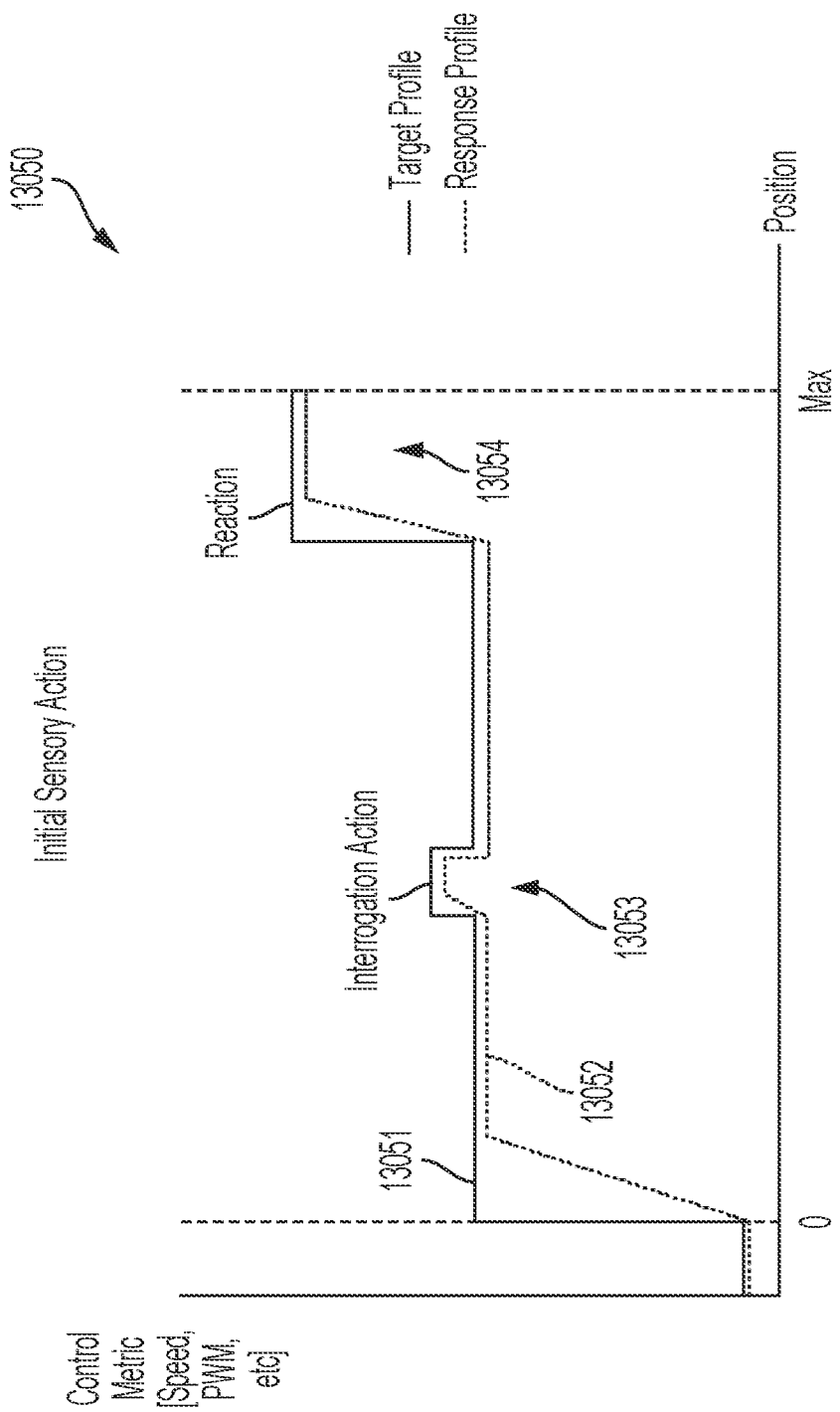
FIG. 18 is a graph depicting a firing stroke performed by a motor system including a motor, a drive train, and a motor control circuit, wherein the motor control circuit performs a sensory action and, in response to the sensory action, performs a reaction a period of time after the completion of the sensory action.

In various instances, the magnitude of the speed increase of the motor during a plurality of sensory, or interrogation, actions gradually increases in magnitude for each subsequent interrogation action. FIG. 18 is a graph 13050 depicting a target speed 13051 and an actual speed 13052 of a staple firing stroke including an interrogation action 13053 and a reaction 13054. During the staple firing stroke, the speed of the motor is increased to a first target speed from a first current speed during the interrogation action 13053. Subsequent to the completion of the interrogation action 13043, a reaction 13054 takes place where, upon determining that the relative capacity of the motor system is not near, at, or above maximum capacity during the interrogation action 13053, the speed of the motor is increased to a second target speed which is greater than the first target speed. In at least one instance, the ratio of the first target speed and second target speed is predefined. For example, the target speed of the interrogation action may include between about 10% and 90% of the target speed of the reaction, for example. In at least one instance, the target speed of the interrogation action may include half of, a quarter of, and/or a third of the target speed of the reaction, for example. Any suitable ratio can be utilized. In at least one instance, the target speed of the interrogation action is greater than the target speed of the reaction.

Figure 19:
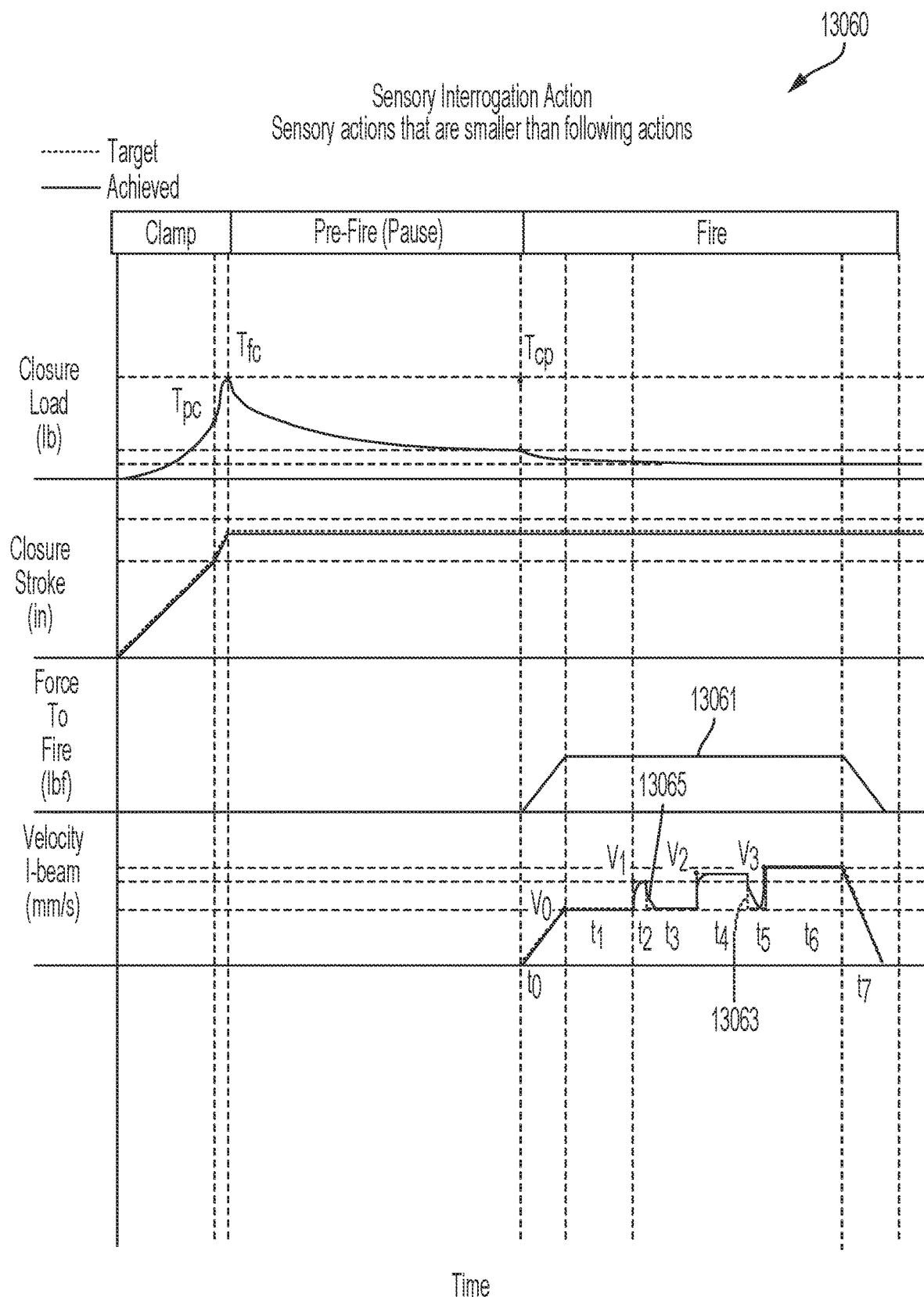
FIG. 19 is a graph depicting a firing stroke performed by a motor system including a motor, a drive train, and a motor control circuit, wherein multiple sensory actions are performed, each including a different target speed magnitude and different time periods.

FIG. 19 is a graph 13060 depicting a staple firing stroke 13061 of a motor system undergoing a plurality of interrogation actions. Closure load (the load experienced by clamping the jaws) and stroke position (the position of the firing member throughout the closure stroke and firing stroke) are also depicted. The force required to fire a firing member, for example, is also depicted for the staple firing stroke 13061. In addition to the above, the actual, or response, speed, or velocity 13065, of the i-beam, or firing member, for example is depicted for the staple firing stroke 13061 as well as the target speed 13063. As can be seen in graph 13060, a plurality of sensory actions are performed targeting speed V1, V2, and V3. Target speed V1 is interrogated for time t2, target speed V2 is interrogated for time t4, and target speed V3 is interrogated for time t6. The time periods t2, t4, and t6 are different. In at least one instance, the time periods of each sensory action are identical. As can be seen in graph 13060, the times t2, t4, and t6 get gradually longer for each subsequent sensory action. As can be also be seen in graph 13060, the magnitude of each target speed increase gradually increases for each subsequent sensory action. During the staple firing stroke 13061, the actual speed 13065 of the motor is within an acceptable level relative to the target speed 13063 for each sensory action. As can be seen in FIG. 19, the load experienced by the firing member does not cause the target speeds V1, V2, and V3 to be missed. In other words, the control circuit determines that the motor system can be run at the target speeds V1, V2, and V3 with the load. In at least one instance, however, the actual speed may vary if the load increases and, as a result, the motor system may not achieve the target speeds V1, V2, and/or V3. In at least one instance, the target speed V3 is a final, optimal, speed set by the control circuit as a result of achieving target speeds V1 and V2.

In at least one instance, the time period at which a target speed is maintained for each sensory action doubles for each subsequent sensory action. In at least one instance, the magnitude of the target speed for each sensory action is identical until the target speed can be achieved. In such an instance, the speed of the motor is permanently set at the target speed and a new target speed is set for subsequent sensory actions until the new target speed can be achieved.

In at least one instance, the collection of target speeds selected for sensory actions during a staple firing stroke can be referred to as a target speed profile. In at least one instance, the target speed profile can be preselected for different types of instruments and/or predefined by a user. For example, a surgical stapling instrument with a 60 mm cartridge may include a first target speed profile while a surgical stapling instrument with a 45 mm cartridge may include a second target speed profile which is different than the first target speed profile. In at least one instance, one surgical stapling instrument may require sensory actions which include target speeds having a greater magnitude than another surgical stapling instrument to increase operating efficiency of each corresponding motor. In other words, a motor of one system designed to operate at a higher speed as compared to a motor of a second system designed to operate at a lower speed may require sensory actions with target speeds having greater magnitude than the second system to have more effective reactions during a staple firing stroke, for example. In at least one instance, the time period of each sensory action includes a length which is imperceptible to a user during use of a surgical stapling instrument, for example. In at least one instance, the magnitude of the target speed of each sensory action includes a magnitude which is imperceptible to a user during use of a surgical stapling instrument, for example.

Figure 20:
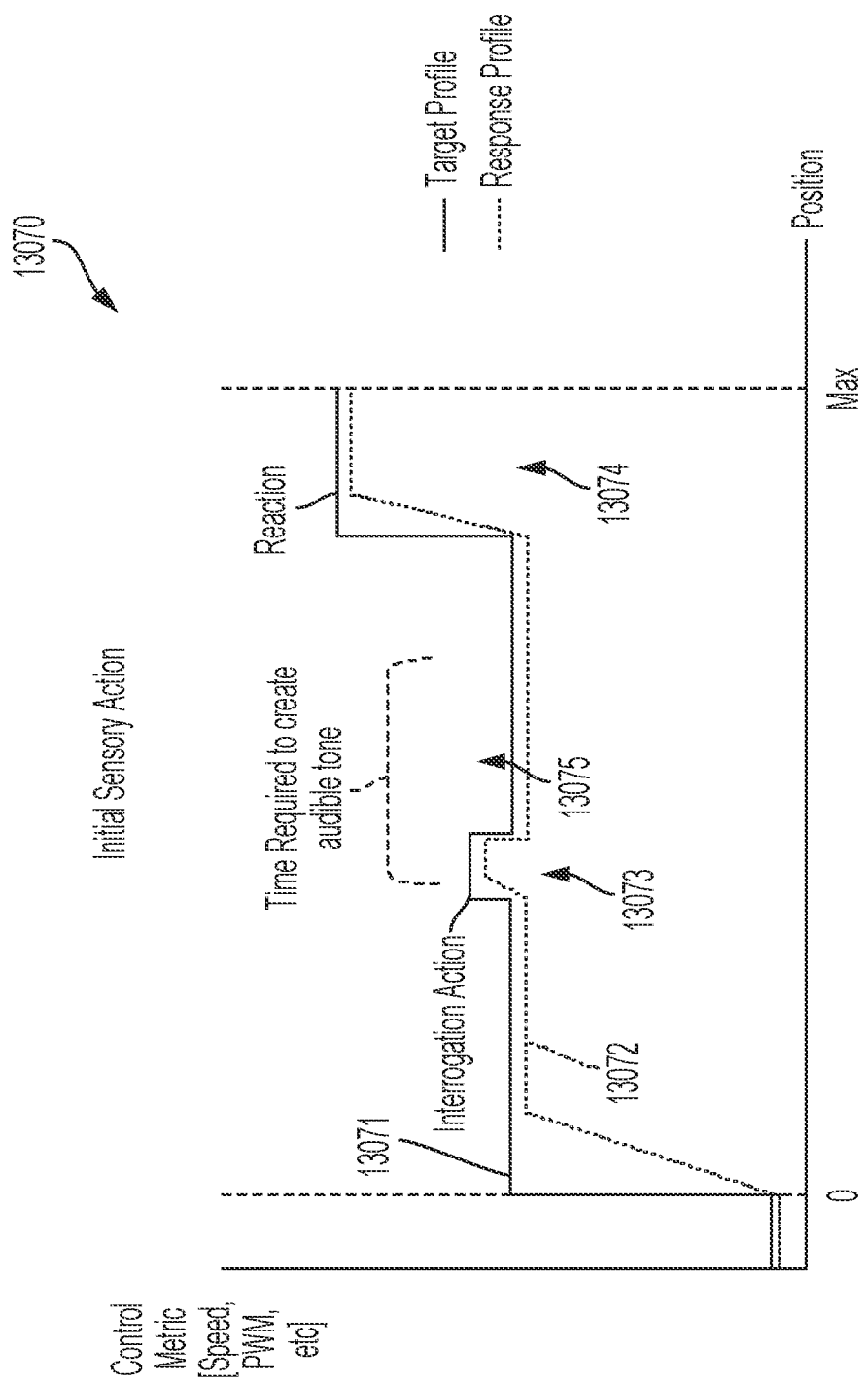
FIG. 20 is a graph depicting a firing stroke performed by a motor system including a motor, a drive train, and a motor control circuit, wherein the motor control circuit performs a sensory action and, in response to the sensory action, after a predefined time period, performs a reaction.

FIG. 20 is a graph 13070 depicting a target speed 13071 and an actual speed 13072 of a staple firing stroke including an interrogation action 13073 and a reaction 13074. During the staple firing stroke, the speed of the motor is increased to a first interrogation target speed during the interrogation action 13073. Subsequent to the completion of the interrogation action 13073, a reaction 13074 takes place where, upon determining that the relative capacity of the motor system is not near, at, or above maximum capacity during the interrogation action by comparing an interrogation response speed to the first interrogation target speed, the speed of the motor is increased to a second reaction target speed which is greater than the first interrogation target speed. In at least one instance, a time period 13075 is set to alert a user, for example, that a reaction is about to take place. Because the first interrogation target speed was achieved, or at least an acceptable percentage of the first interrogation target speed was achieved, during the interrogation action 13073, the motor control circuit alerts a user that a condition has been met to set a reaction, or permanent action, within the time period 13075. In at least one instance, the time period 13075 includes audibly alerting a user at the beginning of the time period 13075 and, at the end of the time period 13075, the reaction 13074 is initiated (the motor is set to the second reaction target speed).

In various instances, a sensory action involves a motor control circuit setting a sensory, or interrogation, target speed for a motor to achieve. However, any suitable variable of the motor system can be set. For example, in at least one instance, displacement of a firing member is set and measured. For instance, a target displacement may be set and actual displacement measured and compared to the target displacement to determine if the motor system is below, near, at, and/or above maximum capacity. In at least one instance, motor current, motor voltage, motor duty cycle, and/or motor displacement are used to set a target variable and compare a measured, or response, variable against the target variable.

Figure 21:
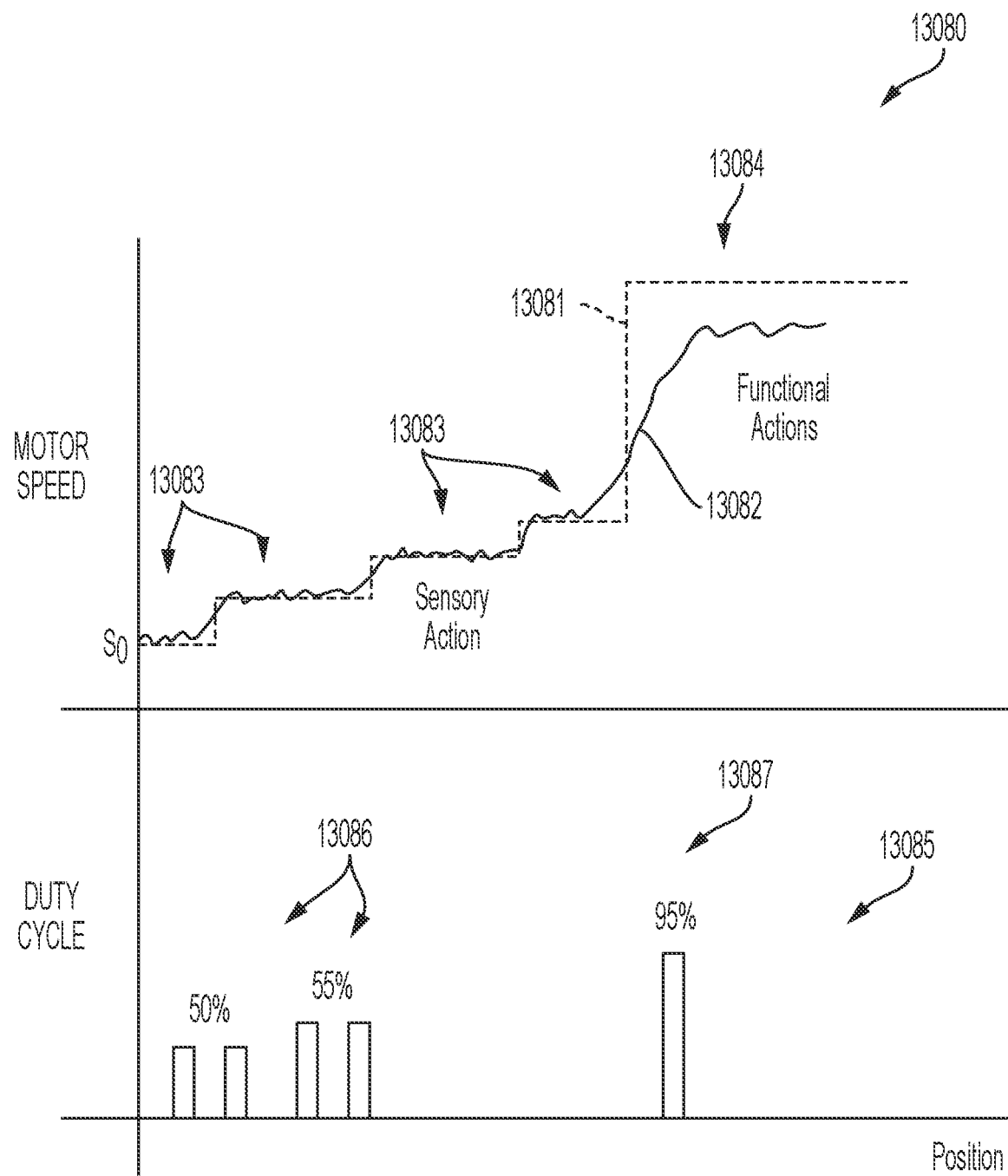
FIG. 21 is a graph depicting a firing stroke performed by a motor system including a motor, a drive train, and a motor control circuit, wherein the motor control circuit performs multiple sensory actions by increasing a target motor duty cycle and, after the completion of the sensory actions, performs a functional action or reaction.

FIG. 21 is a graph 13080 depicting a target speed 13081 and an actual speed 13082 of a staple firing stroke including a plurality of incremental interrogation actions 13083 and a reaction, or functional action, 13084. The graph 13080 also illustrates the set duty cycle 13085 of a pulse width modulation circuit of the motor during the staple firing stroke. As can be seen in the graph 13080, the set duty cycle incrementally increases 13086 during the sensory, or interrogation, actions 13083 and the set duty cycle is increased substantially 13087 during the reaction 13084. The duty cycle may be incrementally increased at any suitable rate at any suitable magnitude. In at least one instance, the rate of change of the duty cycle and/or the magnitude of the duty cycle changes is based on the length of the interrogation actions, the length of the staple firing stroke, and/or the desired speed of the staple firing stroke. In at least one instance, the delta between each set duty cycle is small enough to be imperceptible to a user during a staple firing stroke. As can be seen in FIG. 21, an incremental increase of 5% is made to the duty cycle during each interrogation action and an increase to 95% is made during the reaction. In at least one instance, the incremental increase includes increasing the duty cycle between about 1% and about 10%, for example. In at least one instance, the increase made to the duty cycle during the reaction includes increasing the duty cycle a predefined percentage (between about 25% and about 50%, for example). In at least one instance, the increase made to the duty cycle during the reaction includes increasing the duty cycle to a maximum percentage such as, for example, about 85%, about 90%, about 95%, and/or about 99%.

In at least one instance, type, thickness, and/or toughness of tissue, force to fire a firing member during a staple firing stroke, and/or system losses (backlash, for example) can be the deciding factor for determining whether or not the motor system can handle a substantive speed increase during either a subsequent interrogation action and/or a reaction. For example, thicker tissue may cause higher forces to fire which may place the motor system at, near, and/or above its maximum capacity. Thinner tissue may cause lower forces to fire which may place the motor system well below its maximum capacity. In such an instance, the magnitude of the set variable of the reaction can be substantially increased to reflect the increased relative capacity of the motor system.

As discussed herein, the relative capacity of the motor system can be determined in any suitable manner. In at least one instance, the relative capacity of the motor system can be determined by monitoring a relationship between a set target variable and the corresponding actual measured variable during either an interrogation action and/or a reaction.

In the instance of motor speed, for example, a first target speed is set and the corresponding actual speed is measured. This speed can be measured at the motor output (the speed of the output shaft) and/or within the end effector (the speed of the firing member, knife and/or sled, for example). In at least one instance, the actual speed of the motor output shaft as well as the actual speed of the firing member within the end effector are compared and averaged. At any rate, the actual speed of the motor output shaft, for example, is compared to the set first target speed. In at least one instance, the difference in target speed and actual measured speed can reflect relative capacity of the motor system. For example, it may be determined that a 10% difference in speed indicates that the motor system is not at full capacity (and/or anywhere between about 5% and about 95%, for example). The 10% difference may be a result of system losses such as heat and/or backlash, for example. If the difference in target speed and actual measured speed is 15% (greater difference than at 10%), this may indicate less relative capacity of the motor system is available. If the difference in target speed and actual measured speed is near or at about 100%, this may indicate that the motor system is near, at, or beyond maximum capacity.

In at least one instance, a threshold magnitude is set by a user, automatically set by a control circuit, or predetermined for one or more sensory actions and/or one or more reactions. In various instances, the threshold magnitudes for the sensory actions and/or the reactions are tuned based on the type of instrument, a length of the staple cartridge, the size of the staples in the staple cartridge, the type of tissue being incised and stapled, and/or the articulated position of the end effector. For example, in some instances, firing shafts are flexible and traverse an articulation joint into the end effector. In such an instance, the firing shaft may experience increased load when the end effector is in an articulated position such as, for example, a fully articulated position. As a result, the threshold magnitude of a target variable for the sensory actions and/or the reactions can be reduced so as to prevent overstraining the motor system more quickly.

In at least one instance, a control circuit monitors the articulation position based on inputs from one or more sensors. The control circuit may select the threshold magnitude of a target variable for the sensory actions and/or the reactions based on the inputs from the one or more sensor that are indicative of the articulation position.

It may be desirable to reduce the threshold magnitude of the target parameter (such as target speed, for example) for one or more sensory actions when the end effector is in an articulated position so as to reach optimal efficiency at a similar rate at which optimal efficiency is attained while the end effector is in its straight configuration. In other words, more torque may be required to drive a flexible firing member, for example, through an articulation joint when the end effector is articulated and, thus, through a staple firing stroke. In such an instance, a control circuit can determine that, notwithstanding any other variable, more motor capacity is going to be used to deploy the firing member through a staple firing stroke when the end effector is in an articulated position. In such an instance, the control circuit can automatically reduce the target speed, for example, when the end effector is articulated relative to a target speed at which the control circuit would set for an end effector in a straight configuration in an effort to reduce one or more failed sensory actions.

In at least one instance, the duration of the sensory actions may be tuned based on the type of instrument, a length of the staple cartridge, the size of the staples in the staple cartridge, the type of tissue being incised and stapled, and/or the articulated position of the end effector, for example. In at least one instance, a maximum time threshold is set for the duration of the sensory actions. In at least one instance, a minimum time threshold is set for the initiation of a reaction, or functional action. For example, a request for an increase in speed of the motor, by a user or automatically by a motor control circuit, can be made at which point a timer is set so as to prevent a reaction from occurring until the timer has concluded. In at least one instance, a reaction including a further increase of speed is delayed until the timer has concluded. In at least one instance, a reaction including a decrease in speed is delayed until the timer has concluded.

In at least one instance, a sensory action is performed on a motor system by a motor control circuit during pre-compression. In at least one instance, pre-compression is referred to as the time after the tissue is initially clamped but before the beginning of the staple firing stroke where additional clamping load may be applied to the tissue. In at least one instance, the !-beam within an end effector is configured to travel a predefined amount of distance prior to the beginning of the firing stroke (such as, for example, prior to contacting an unfired sled and/or a lockout) and after the tissue is initially clamped. As discussed herein, the firing and clamping functions may be actuated independently with separate and distinct drive systems. As also discussed herein, the firing and clamping functions may be actuated with a single firing drive member. Pre-compression may be present in each of these arrangements. In at least one instance, pre-compression is defined as the time, or distance, between partially clamping tissue and fully clamping tissue.

Within the predefined amount of distance, one or more sensory actions may be performed to determine a speed at which to deploy the firing member through the staple firing stroke. In at least one instance, the firing member is driven forward, reversed, and forward again one or more times within the predefined amount of distance so as to continuously monitor the relative capacity of the motor system prior to beginning the staple firing stroke, for example. In at least one instance, the number of times the firing member is driven forward and reversed to perform the one or more sensory actions is dependent on the tissue clamped within the end effector. The tissue clamped within the end effector can require time to settle and/or stabilize, for example. In at least one instance, the firing member is repeatedly cycled through a forward and reverse cycle until the tissue is stabilized. This initial movement of the firing member prior to contacting the sled may provide an arrangement which is capable of assessing initial firing loads to be expected during the staple firing stroke. As discussed herein, the length, time, and/or speed of this initial movement in addition to the sensory actions and/or reactions occurring within the initial movement of the firing member may be selected, set, and/or defined so as to be imperceptible to a user.

Figure 22:
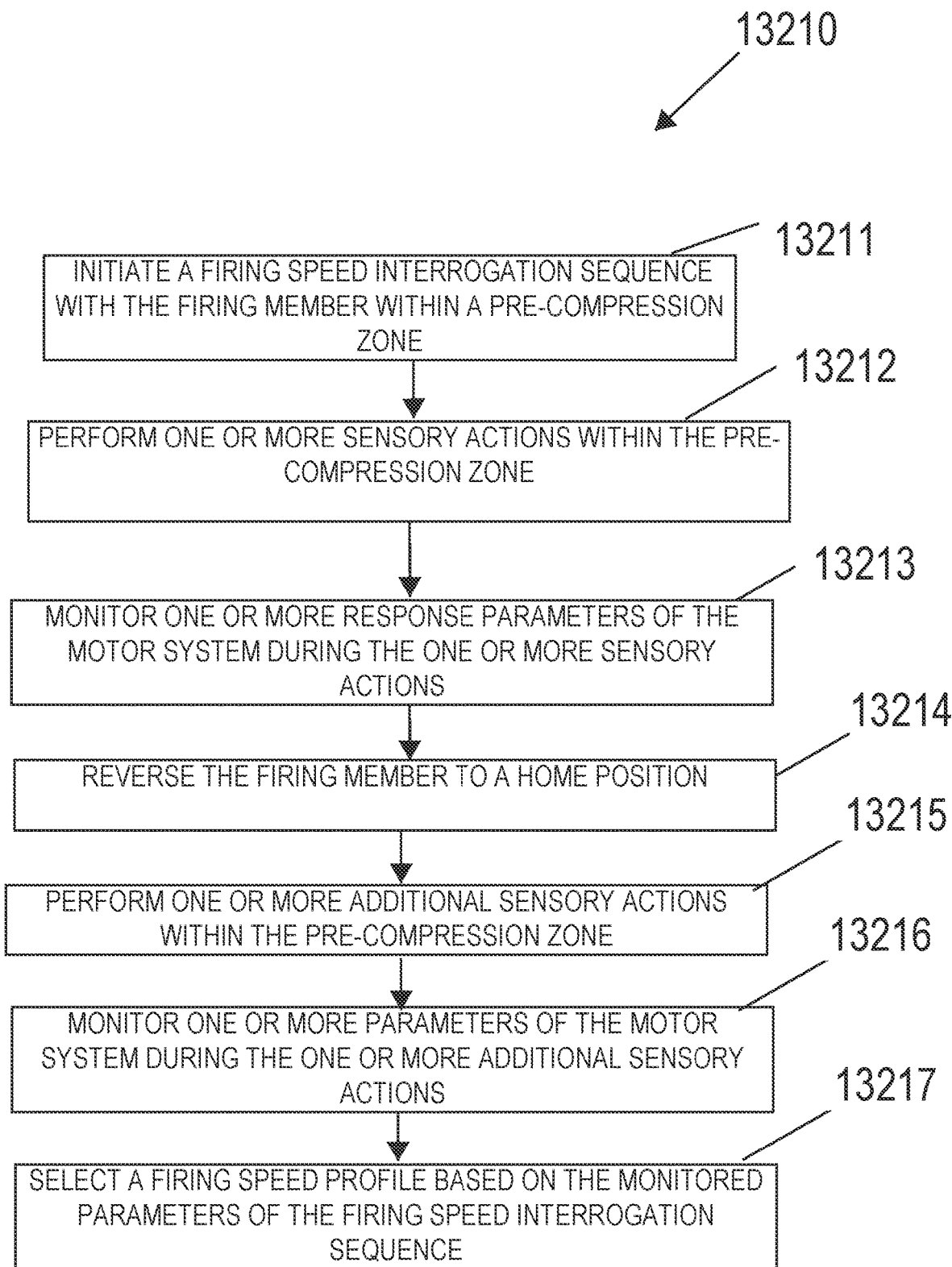
FIG. 22 is a logic flow chart depicting a process executable by a control circuit, wherein the process includes actions for controlling the motor of a surgical instrument system, wherein the control circuit is configured to perform a plurality of sensory action sequences during a pre-compression stage to determine a firing speed of the motor for a staple firing stroke.

FIG. 22 is a logic flow chart depicting a process 13210 executable by a control circuit, such as the control circuit 1932 illustrated in FIG. 13 and/or the control circuit illustrated in FIG. 14, for example, for controlling the motor of a motor system of a surgical instrument system such as those disclosed herein. The control circuit is configured to initiate 13211 a firing speed interrogation sequence of a firing member within a pre-compression zone. The control circuit is configured to perform 13212 one or more sensory actions within the pre-compression zone. During the one or more sensory actions, the control circuit is configured to monitor 13213 one or more response parameters of the motor system. The control circuit is configured to reverse 13214 the firing member to a home position. The control circuit is configured to perform 13215 one or more additional sensory actions within the pre-compression zone. During the one or more additional sensory actions, the control circuit is configured to monitor 13216 one or more response parameters of the motor system. In at least one instance, the firing speed interrogation sequence occurs one or more times such as, for example, 3, 5, and/or about 10 times, for example. In at least one instance, the firing speed interrogation sequence occurs a predetermined number of times before a firing speed is selected for a subsequent staple firing stroke. Nonetheless, the control circuit is configured to select 13217 a firing speed profile based on the monitored parameters of the cyclical sensory actions performed within the pre-compression zone. In at least one instance, the firing speed interrogation sequence occurs within a clamping zone of the firing member and/or after clamping but before firing any staples, for example.

In at least one instance, cycling the firing member in the manner discussed above during the pre-compression stage can also help identify and understand the process of the tissue stabilization. For example, if relatively thick tissue is clamped, a firing member cycled during the pre-compression stage in the manner discussed herein may reveal that the motor system is near, at, and/or above maximum, or optimal, capacity prior to firing, for example, indicating that relatively thick tissue has been clamped and/or indicating that the relatively thick tissue clamped within the end effector is taking longer than expected to stabilize. Adjustments can be made to various parameters of the motor system based on information gleaned from the initial movement of the firing member during the pre-compression stage. For example, if thick tissue is clamped within the end effector and determined during the pre-compression stage, the parameters and variables of the sensory actions and/or the reactions can be tuned based on the detection of the thick tissue during the pre-compression stage, for example. The information gleaned from the initial movement of the firing member during the pre-compression stage can also be used to decide how long to allow the tissue to stabilize. Referring to FIG. 22, the information is gleaned from monitoring 13213 and monitoring 13216 one or more parameters of the motor system during the sensory actions and the additional sensory actions, for example.

In various instances, an imperceptible sensory, or interrogation, action is skipped and reactions, or functional actions, are performed to determine if there exists excess capacity within the motor system. For example, the speed of the motor can be increased a perceptible amount. Similar to the sensory actions discussed above, a motor control circuit can determine if the perceptible increased speed is achieved or not achieved by measuring the actual speed attained in response to the perceptible speed increase. In at least one instance, a functional action configured to increase the speed of the motor until it is determined that the target speed cannot be realized is terminated once it is determined that the target speed cannot be realized. For example, the functional action may gradually increase the speed of the motor in a stepped and/or continuous fashion until the actual speed of the motor deviates from the target speed below a differential threshold.

In at least one instance, sensory actions and/or functional actions are performed throughout an entire staple firing stroke in an effort to maintain optimal operational efficiency of the motor system. For example, the speed of a firing motor may be slowed down and sped up constantly while the relative capacity of the motor system is constantly monitored and evaluated. In at least one instance, a limited number of sensory actions and/or functional actions are performed. In at least one instance, the limited number is set by a user and/or a motor control program, for example. The limited number may be based on the age of the instrument and/or the motor system, the type of the instrument, the function of which the motor system actuates, or any suitable parameter, for example.

Figure 23:
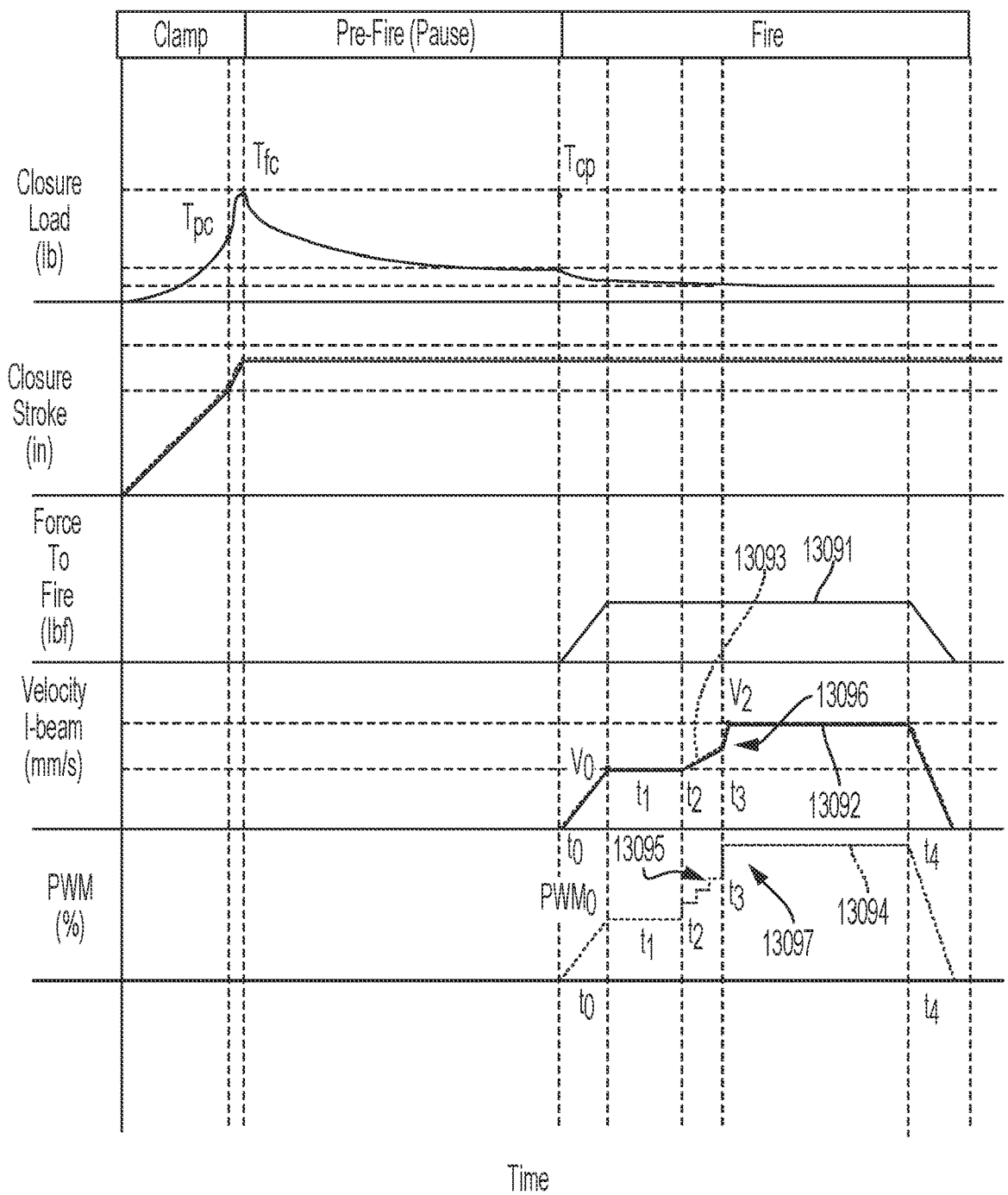
FIG. 23 is a graph depicting a firing stroke performed by a motor system including a motor, a drive train, and a motor control circuit, wherein multiple sensory actions are performed by incrementally increasing the target motor duty cycle and, after the sensory actions are complete, performs a reaction.

FIG. 23 is a graph 13090 illustrating a clamping stroke and a firing stroke of a surgical instrument system. In at least one instance, the clamping and firing strokes are performed by separate drive members. In at least one instance, the clamping and firing stroke are performed by a single drive member. A force-to-fire 13091 is depicted for the staple firing stroke. The target speed 13093 and actual speed 13092 of the firing member during the staple firing stroke are also depicted. In addition to the above, the PWM signal, 13094 of the motor is also illustrated. As can be seen in the graph 13090, the PWM signal 13094 is incrementally increased 13095, by increasing the duty cycle, for example. In at least one instance, it is determined that there exists excess capacity within the motor system to reach a speed V2 at which point a function action 13096 is taken to increase the speed of the motor to speed V2. This is achieved by increasing 13097 the PWM signal. In at least one instance, the PWM signal is increased to a duty cycle 13097.

In at least one instance, sensory actions are also performed during retraction of a firing member through an end effector. Such an arrangement can provide a quicker retraction stroke without increasing the speed of the motor to, or beyond, its maximum, or optimal, capabilities, which could cause instability in a motor system.

Figure 24:
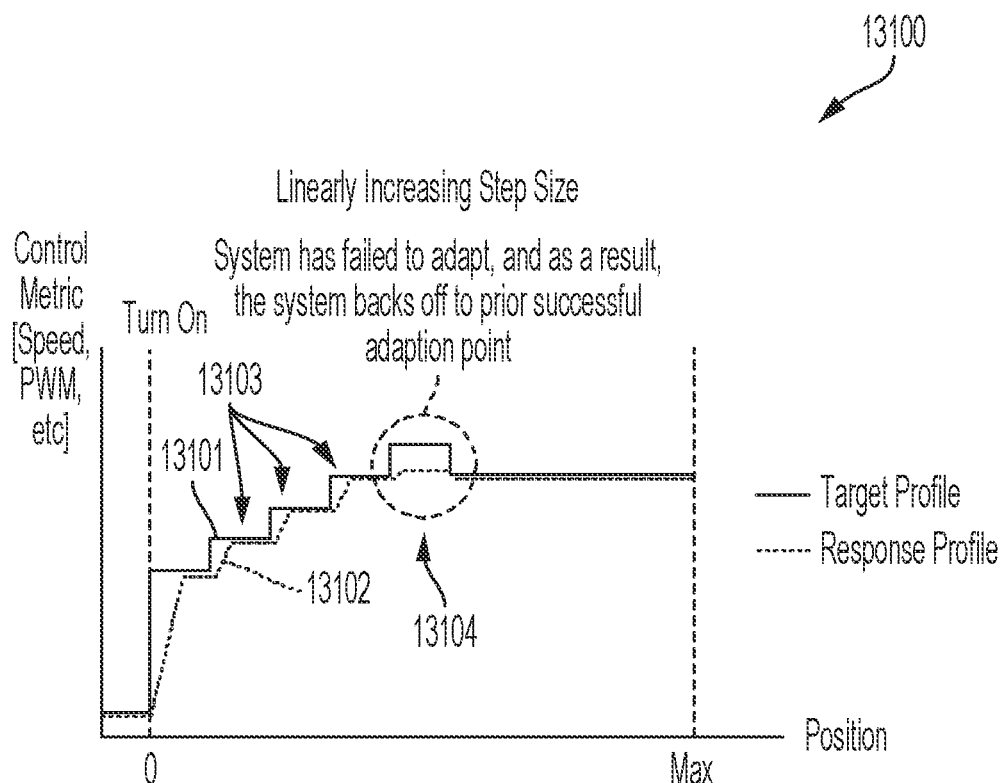
FIG. 24 is a graph depicting a firing stroke performed by a motor system including a motor, a drive train, and a motor control circuit, wherein the motor control circuit performs multiple sensory actions by linearly increasing a target speed magnitude for each subsequent sensory action, wherein the motor control circuit is configured to revert the target speed of the motor back to a target speed achieved during a prior successful sensory action.

FIG. 24 is a graph 13100 depicting a target speed 13101 and an actual speed 13102 of a staple firing stroke of a motor system including a plurality of discrete interrogation actions 13103. In at least one instance, each interrogation action 13103 includes an identical magnitude of change such as, for example, an identical increase in speed. In certain instances, the step size can increase linearly among the discrete interrogations. In other instances, the step size can vary among the discrete interrogations.

In the illustrated example, the plurality of discrete interrogations 13103 includes a final interrogation action 13104. During the staple firing stroke, the speed of the motor is increased incrementally during each interrogation action 13103. At the final interrogation 13104, an anticipated response of the actual speed 13102 is not realized and, thus, a motor control circuit reverts the speed of the motor back to the target speed of the previous interrogation action 13103. In at least one example, the motor control circuit determines that a response is not realized where the difference between the actual speed 13102 and the set target speed is beyond a predetermined threshold.

Figure 25:
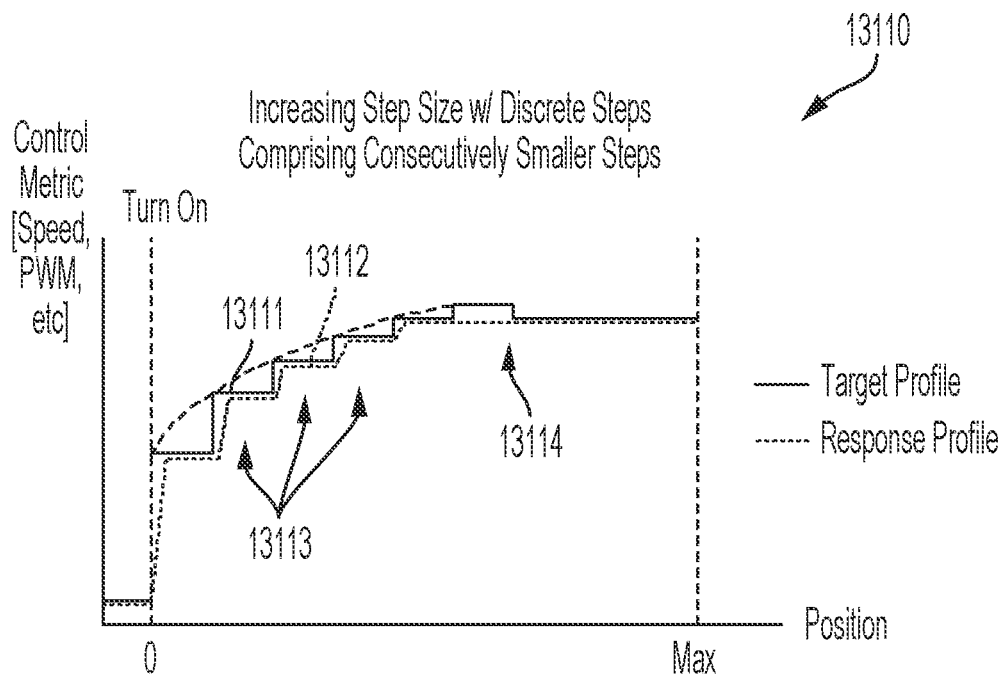
FIG. 25 is a graph depicting a firing stroke performed by a motor system including a motor, a drive train, and a motor control circuit, wherein the motor control circuit performs multiple sensory actions by increasing a target speed magnitude for each subsequent sensory action with consecutively smaller target speed magnitudes, wherein the motor control circuit is configured to revert the target speed of the motor back to a target speed achieved during a prior successful sensory action.

FIG. 25 is a graph 13110 depicting a target speed 13111 and an actual speed 13112 of a staple firing stroke of a motor system including a plurality of discrete interrogation actions 13113. In at least one instance, the magnitude of each interrogation action 13113 decreases with each subsequent action. For example, the increase in speed of the motor for each subsequent interrogation action 13113 decreases. In at least one instance, the decrease in magnitude of each interrogation action 13113 corresponds to the determination of the relative capacity of the motor system through the actual speed, or response profile, 13112 relative to the target speed, or target profile, 13111. For example, if the actual speed 13112, at some point, starts to gradually deviate further away from the anticipated speed with each interrogation action 13113, employing consecutively smaller interrogation actions can help achieve maximum efficiency by reducing overshoot. In at least one instance, the rate at which the magnitude of each interrogation action 13113 decreases is selected by a motor control circuit based on the rate of deviation of the actual speed 13112 relative to the target speed 13111. The plurality of discrete interrogation actions 13113 includes a final action 13114. At the final action 13114, the target speed 13111 is not realized and, thus, the motor control circuit reverts the speed of the motor back to the target speed of the previous interrogation action 13113.

Figure 26:
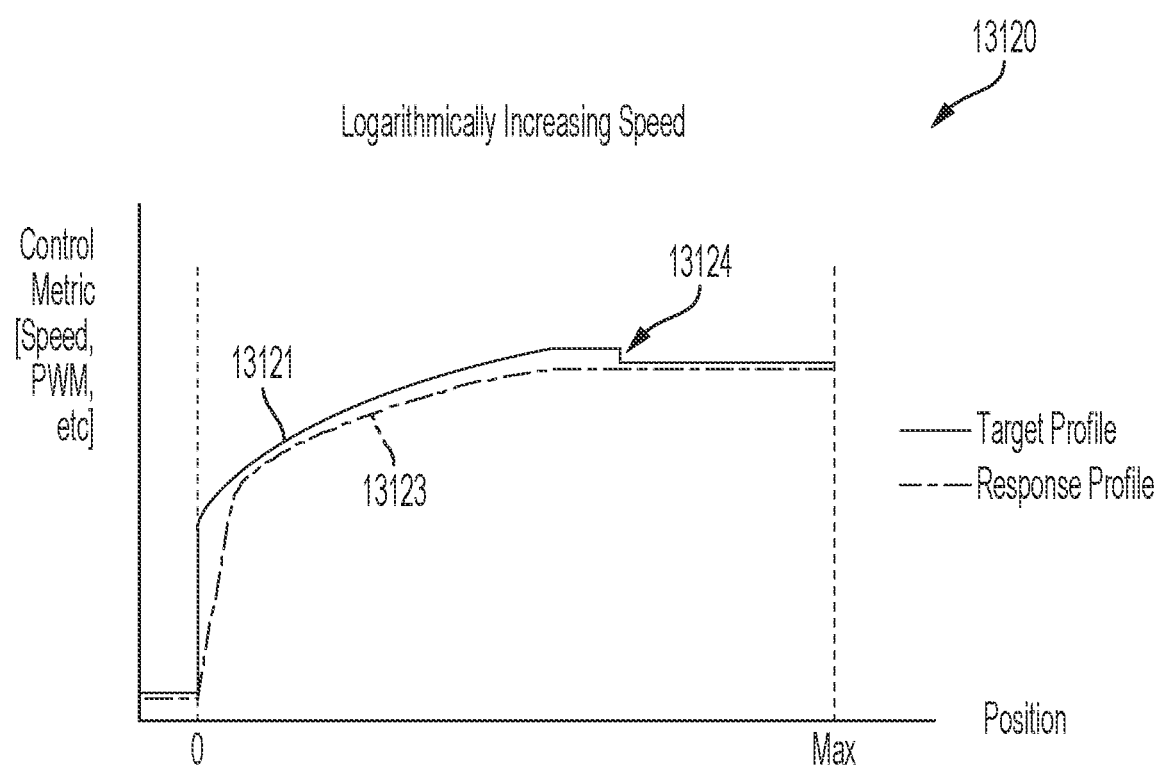
FIG. 26 is a graph depicting a firing stroke performed by a motor system including a motor, a drive train, and a motor control circuit, wherein the motor control circuit performs multiple sensory actions by logarithmically increasing a target speed magnitude for each subsequent sensory action, wherein the motor control circuit is configured to revert the target speed of the motor back to a target speed achieved during a prior successful sensory action.

FIG. 26 is a graph 13120 depicting a target speed 13121 and an actual speed 13123 of a staple firing stroke of a motor system including a target profile including a logarithmic increase in a control metric of the firing stroke such as, for example, a speed or PWM, and a response action 13124. Logarithmically increasing the control metric, e.g. PWM or speed, of the motor may reduce overshoot, for example. As can be seen in the graph 13120, the target speed 13121 is held constant for a period of time following the logarithmic interrogation. In at least one instance, a motor control circuit can hold the target speed 13121 constant upon determining a threshold deviation between the target speed 13121 and the actual speed 13123 has been reached. The period of time may provide the motor system time to settle or overcome an unexpected section of tissue, for example, thus giving the actual speed 13123 time to settle. In at least one instance, the actual speed 13123 never recovers and the response action 13124 is initiated. In at least one instance, the actual speed 13123 recovers to at least a certain degree and the motor system reinitiates interrogation of the motor system and continues to increase the speed of the motor. During the response action 13124, the target speed 13121 is reduced a predefined amount and/or reverted back to a previous target speed threshold. In at least one instance, the magnitude of the reduction of speed at the response action 13124 is based on the magnitude of deviation between the target speed 13121 and the actual speed 13123. In at least one instance, logarithmically increasing the speed of the motor to interrogate the relative capacity of the motor system can increase efficiency and reduce the amount of deviation between actual speed and target speed.

Figure 27:
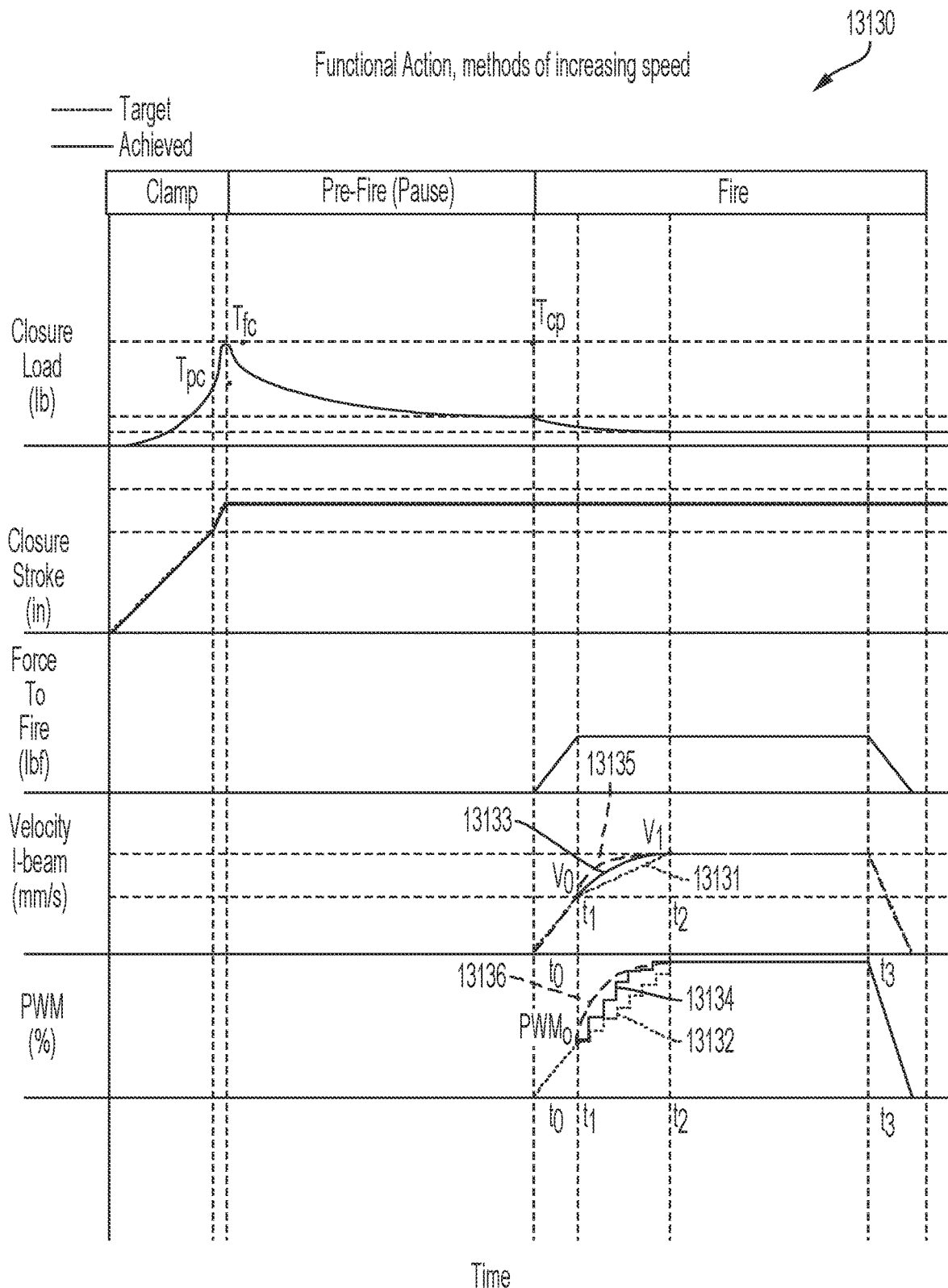
FIG. 27 is a graph depicting several firing strokes performed by a motor system including a motor, a drive train, and a motor control circuit, wherein different sensory action sequences are performed by modulating a motor duty cycle of the motor.

FIG. 27 is a graph 13130 illustrating a clamping stroke and a firing stroke of a surgical instrument system. In at least one instance, the clamping and firing strokes are performed by separate drive members. In at least one instance, the clamping and firing stroke are performed by a single drive member. A force-to-fire is depicted for the staple firing stroke, as well as the closure stroke and the closure load. Three different scenarios are illustrated for interrogating the motor system which drives the firing member. In scenario one, a percentage PWM signal of the motor is increased in discrete linear steps 13132 including an identical magnitude speed increase for each step resulting in a linearly increasing firing member velocity 13131. In scenario two, the percentage PWM signal of the motor is increased in discrete steps 13134; however, the magnitude of each speed increase decreases with each subsequent step resulting in a logarithmically increasing firing member velocity 13133. In scenario three, the percentage PWM signal of the motor is increased logarithmically 13136 resulting in a logarithmically increasing firing member velocity 13135.

Figure 28:
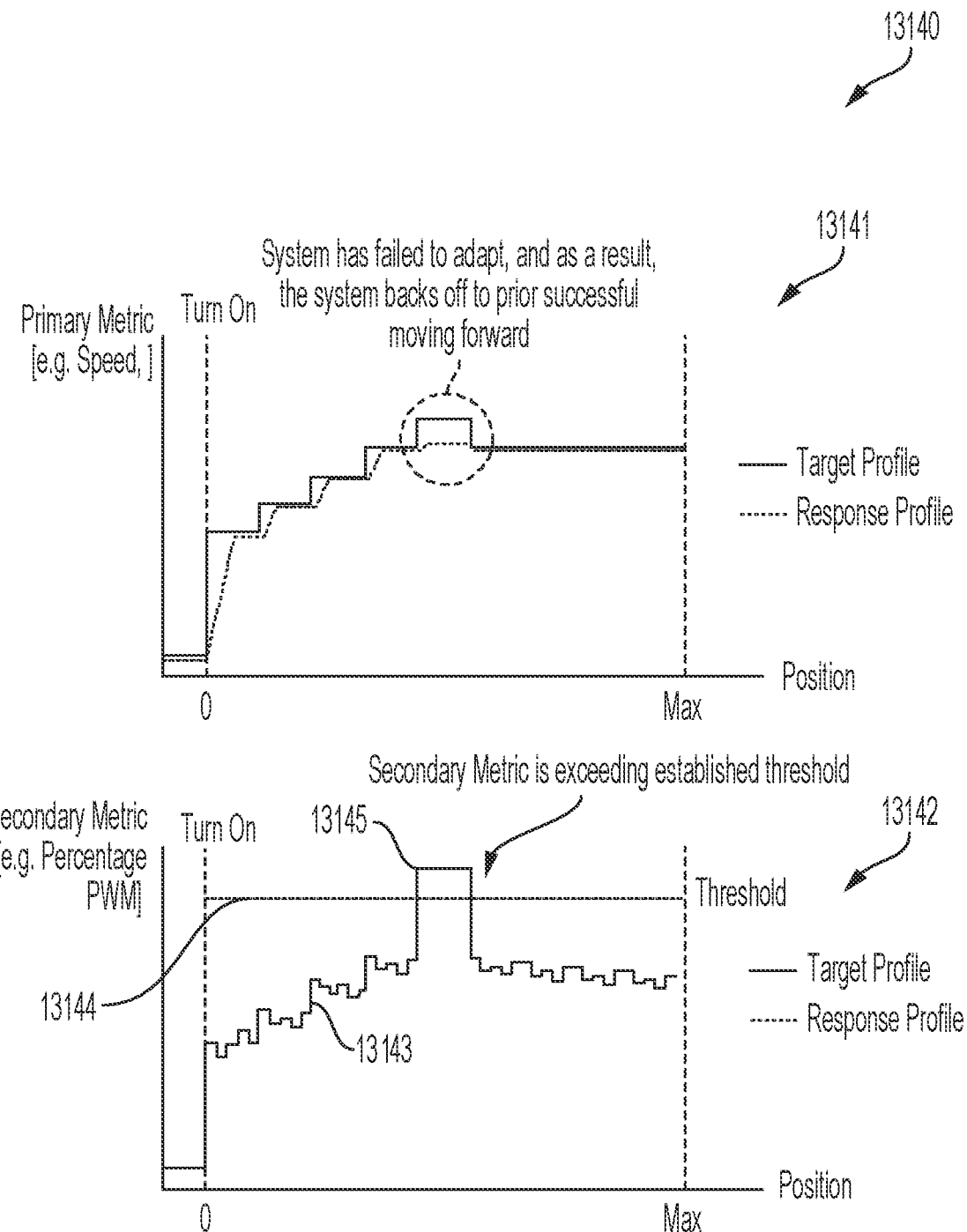
FIG. 28 is a graph depicting a primary sensory metric and a second sensory metric of a motor control circuit configured to control the speed of a motor.

FIG. 28 is a graph 13140 depicting a primary sensory metric 13141 and a secondary sensory metric 13142. In at least one instance, the primary sensory metric 13141 is similar to that of others disclosed herein. For example, the primary sensory metric 13141 involves incrementally increasing the target speed of the motor, monitoring the actual speed of the motor and, upon detecting that the actual speed of the motor deviates from the target speed beyond a predetermined threshold percentage, for example, the motor control circuit reverts the speed of the motor back to a target speed of a prior successful sensory action. In at least one instance, the motor control circuit selects a new target speed based on the failed sensory action which is different than the target speed of the prior successful sensory action and, rather, based on the rate at which the motor deviated from the target speed over time, for example. The secondary sensory metric 13142 is used by the motor control circuit as a redundancy, for example, to reinforce the detected output of the primary sensory metric 13141. For example, a PWM percentage signal 13143 of the motor can be monitored and, upon determining that the PWM percentage signal 13143 exceeds 13145 a predetermined threshold 13144, the motor control circuit determines that the motor system is at or above capacity. In such an instance, this determination coincides with the determination made within the primary sensory metric 13141. Further adjustments to the speed of the motor can be made based on both the primary sensory metric 13141 and the secondary sensory metric 13142. In least one instance, the PWM percentage signal 13143 is attained by converting one or more analog output parameters such as motor speed, for example, to a digital PWM signal.

Figure 29:
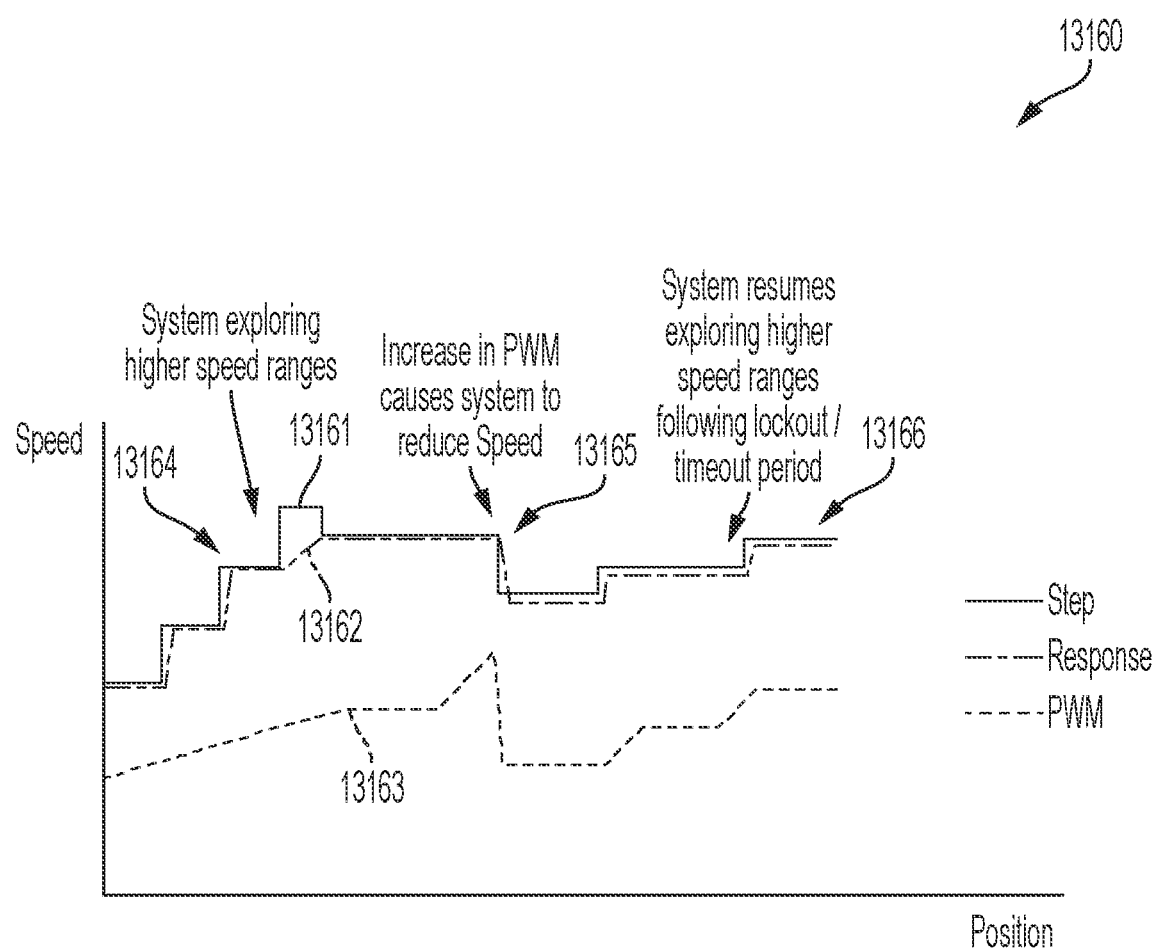
FIG. 29 is a graph depicting a firing stroke performed by a motor system including a motor, a drive train, and a motor control circuit, wherein the motor control circuit employs a speed control algorithm during the firing stroke, and wherein the speed control algorithm utilizes a lockout period upon satisfying a lockout condition.

FIG. 29 is a graph 13160 of an example staple firing stroke performed by a motor system illustrating target speed 13161, actual speed 13162, and pulse width modulation signal 13163 of a motor of the motor system. As can be seen in the graph 13160, the motor system performs sensory actions, or interrogation actions, 13164 in an attempt to increase the speed of the motor within a capacity limit of the motor system. The sensory actions 13164 end when the actual speed 13162 deviates from the target speed 1361 beyond a predetermined threshold, for example.

In at least one instance, the pulse width modulation signal 13163 is increased in an attempt to maintain motor speed through a thick section of tissue, for example. After traversing the thick section of tissue, the PWM signal 13163 is reduced causing a reduction 13165 in speed 13162. At such point, a time delay and/or a lockout period may be instituted by the motor system to prevent the motor system from initiating additional sensory actions, for example. After the time delay and/or the lockout period, the motor system may resume interrogating the relative capacity of the motor system in an effort to achieve an optimal efficiency speed. Such an arrangement may allow for locally optimal speed throughout the length of a staple firing stroke, for example. A cutting member, for example, may encounter a thicker section of tissue but only for a certain length of the staple firing stroke. The tissue may be thinner after the thicker section and, thus, capacity for increasing the speed of the firing stroke may increase after the cutting member passes the thicker section of tissue. At this point, the motor system can reinitiate an interrogation sequence in an effort to maximize the speed of the motor along the entire length of the staple firing stroke. In at least one instance, interrogation sequences initiated after a lockout or time delay is employed may vary in length of time and magnitude as compared to interrogation sequences which occurred prior to the lockout or time delay.

Figure 30:
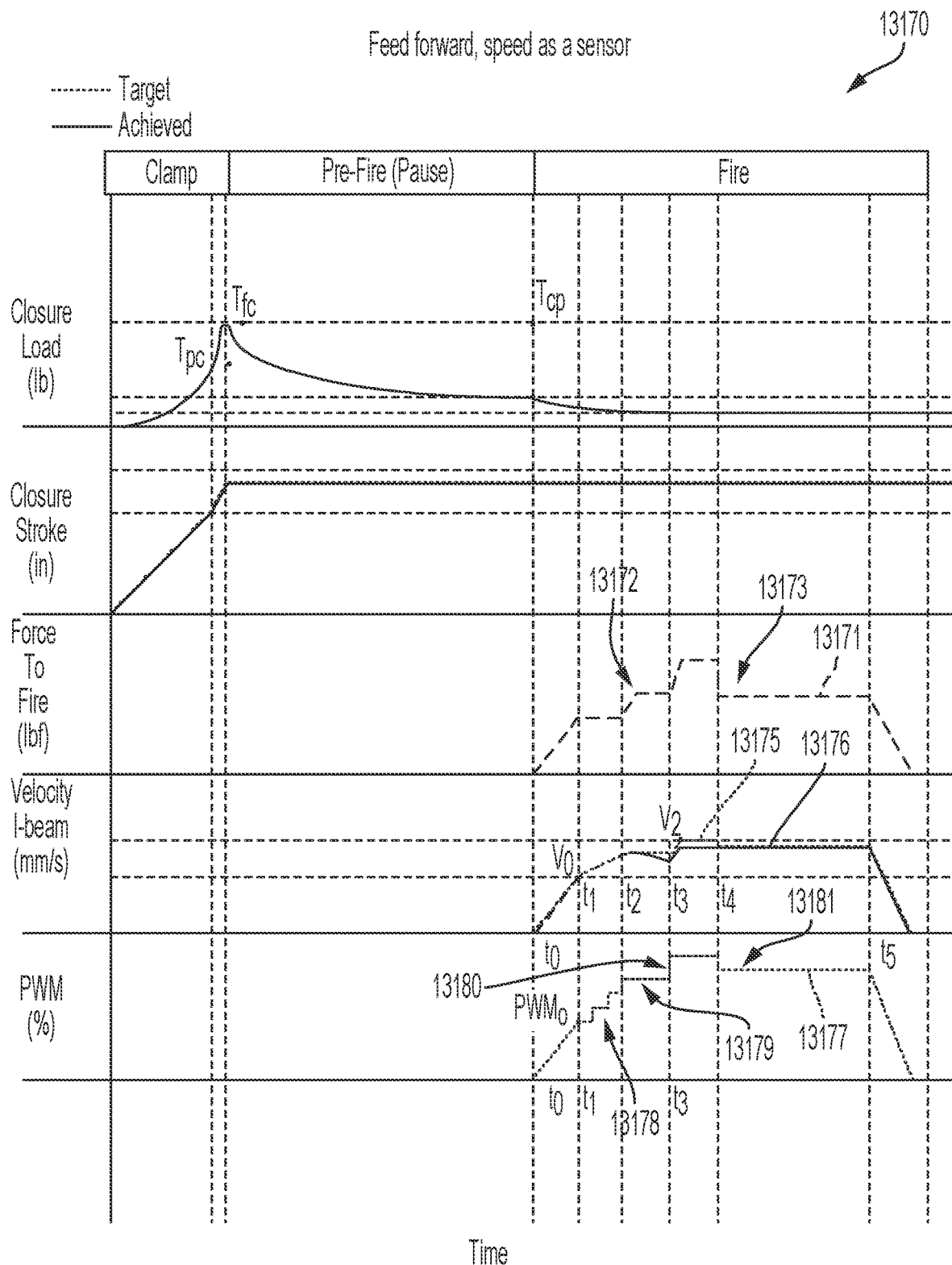
FIG. 30 is a graph depicting a firing stroke performed by a motor system including a motor, a drive train, and a motor control circuit, wherein the motor control circuit performs sensory actions and functional actions.

FIG. 30 is a graph 13170 of a staple firing stroke performed by a motor system including a motor and a firing member configured to be actuated by the motor. The closure load and closure stroke are illustrated. The force to fire 13171 the firing member is also illustrated. As can be seen by the force to fire 13171 plot, the force to fire the firing member increases 13172 between t1, t2, t3, and t4 and decreases 13173 at t4. The actual speed 13176 of the firing member as well as the target speed 13175 of the firing member are also depicted. In at least one instance, the actual speed includes the actual speed of the motor. Further to the above, the PWM percentage 13177 is also depicted. Between t1 and t2, the relative capacity of the motor system is interrogated by increasing the PWM percentage 13177 in discrete steps 13178 in an effort to achieve a set speed. The set speed is achieved at t2. During the time between t1 and t2, the actual speed 13176 of the firing member does not deviate from the target speed 13175.

At t2, the PWM percentage 13177 remains unchanged and the actual speed 13176 begins to deviate from the target speed 13175. At this point, the motor system tries to compensate to re-attain the set speed by sharply increasing the PWM percentage 13177. In at least one instance, the PWM percentage 13177 is unchanged 13179 between t2 and t3 because the actual speed 13176 started to deviate from the target speed 13175. As can also be seen in the graph 13170, the force to fire 13171 the firing member increases between t2 and t3 which may cause the deviation between the actual speed 13176 and the target speed 13175. In at least one instance, the increase in the force to fire can be due to a change in tissue thickness. At time t3, a functional action 13180 is taken by the motor control circuit where the PWM percentage 13177 is sharply increased in an effort to increase the speed 13176 of the motor and/or firing member, for example, back to the previously attained set target speed. Between time t3 and time t4, the speed 13176 of the firing member increases and, while the speed 13176 has not attained the new target speed 13175 of V2, the firing member has re-attained and surpassed the previously attained set speed. In at least one instance, not being able to attain the new speed of V2 is a result of yet another increase in firing force 13171 experienced by the firing member between t3 and t4. Because the target speed V2 is not attained but the previously attained set speed has been re-attained, the PWM percentage 13177 is slightly reduced 13181 (not reverted back to the PWM percentage 13177 utilized between t2 and t3) to achieve optimal efficiency and maintain the optimal speed. At time t4, the PWM percentage is reduced and can be triggered by the reduction in force to fire at t4. At time t4 to time t5, the actual speed 13176 and the target speed 13175 are equal or at least do not deviate beyond a threshold deviation, for example. At such point, the PWM percentage 13177 is held constant until the end of the staple firing stroke. In at least one instance, the set speed is modified during the staple firing stroke based on the response of the motor system to the sharp increase in duty cycle. In at least one instance, the set speed is decreased after the sharp increase in duty cycle. In at least on instance, the set speed is increased after the sharp increase in duty cycle.

In at least one instance, one or more predetermined shifting thresholds are utilized during a sensory action. For example, as the speed of a motor is increased in an effort to determine if there is available capacity to increase the speed of the motor, a relative capacity of the motor system can be defined as a quantifiable amount. For example, it may be determined that the motor system is operating at 50% capacity and has 50% available capacity. A first predetermined shifting threshold can be set at a first percentage of available capacity, for example, to set a threshold for determining that a target speed which is greater than an current speed can be set. Thus, as the speed of the motor is increased and the relative capacity of the motor system is determined, once it is determined that there is the first percentage of available capacity or more available, the motor control signal can be adjusted to shift the speed of the motor to an increased target speed. In at least one instance, the system performs another sensory action and, if there still exists the first percentage of available capacity or more, the speed of the motor is increased again. In at least one instance, an additional predetermined shifting threshold is set to determine when to shift the speed of the motor to a decreased new speed. For example, 5% available capacity can be set as a second predetermined shifting threshold. Thus, when 5% available capacity or less is detected, the motor control circuit can reduce the speed of the motor to the decreased new speed. As discussed herein, the percent deviation from the threshold values can be utilized to determine the magnitude of the new speeds. For example, if there exists 75% relative capacity in a system with a 25% first predetermined shifting threshold, the relatively large availability in capacity can cause the motor control circuit to increase the magnitude of the motor speed increase accordingly. On the other hand, if 0% capacity exists and/or the motor system is beyond maximum capacity (0%, for example), a large magnitude of speed decrease can be utilized to more appropriately adjust the motor toward an optimum operating speed, for example, in response to being at or beyond maximum motor capacity.

Figure 31:
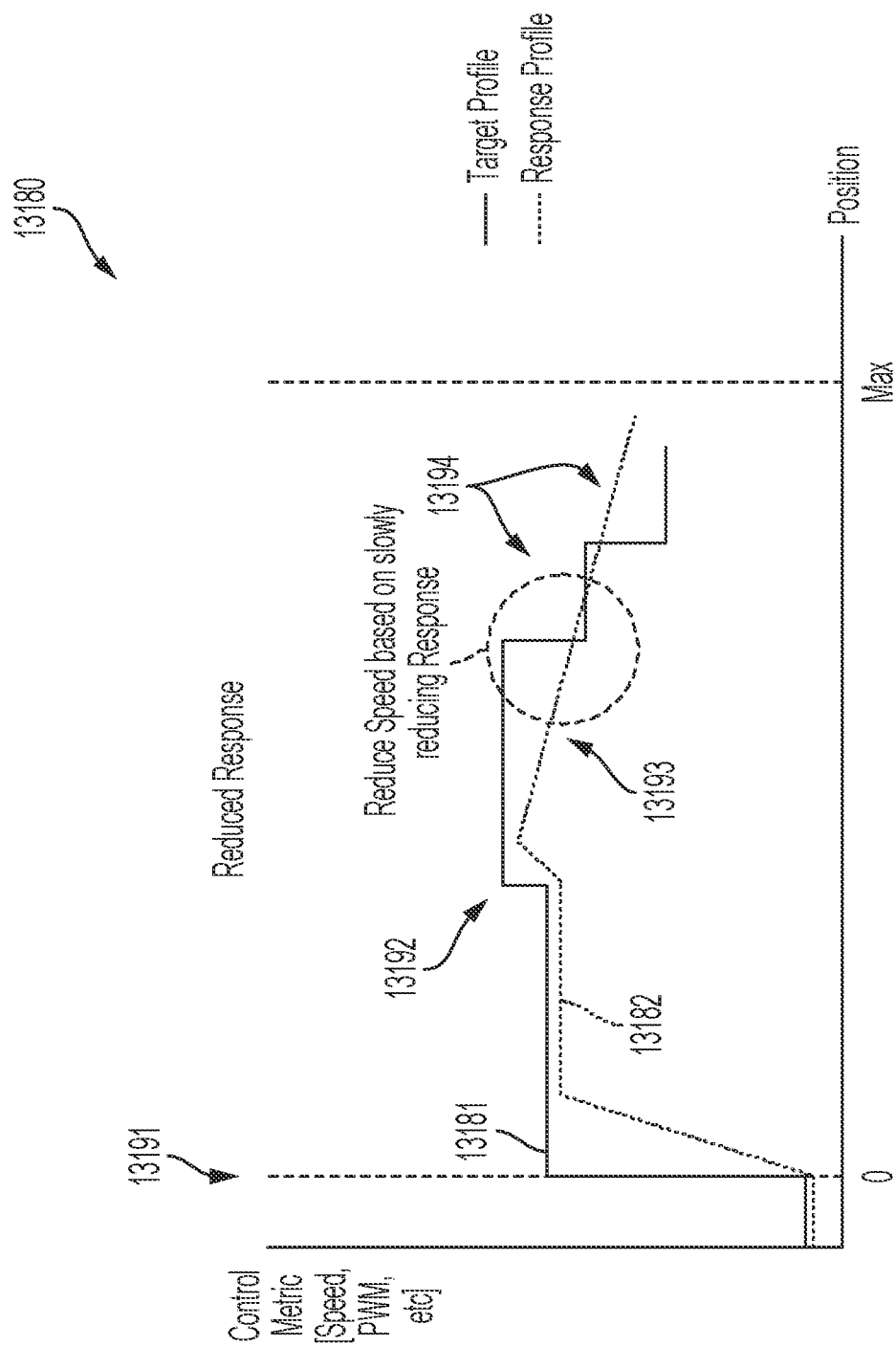
FIG. 31 is a graph depicting a firing stroke performed by a motor system including a motor, a drive train, and a motor control circuit, wherein the motor control circuit performs a sensory action and, in response to the monitored actual speed of the motor during the sensory action gradually declining, performs multiple functional actions to reduce the speed of the motor.

FIG. 31 is a graph 13180 of an example staple firing stroke performed by a motor system illustrating target speed 13181 and actual speed 13182. In at least one instance, the motor control circuit is configured to reduce the speed of the motor upon determining that a threshold deviation between the actual speed 13182 and the target speed 13181 is detected. In at least one instance, the rate at which the deviation between the actual speed 13182 and the target speed 13181 increases and/or decreases is monitored and, upon reaching a rate of change threshold (e.g. the actual speed 13182 is falling too quickly relative to the target speed 13181), speed adjustments are made through one or more reactions. As can be seen in the graph 13180, the motor system initiates 13191 the firing sequence and sets the target speed 13181 to a first target speed. At some point, the motor system then performs a sensory action 13192 by increasing the target speed 13181 of the motor to a second target speed for a specific time period during which the actual speed 13182 and/or percent deviation between the actual speed 13182 and second target speed is monitored. Upon determining that the actual speed 13182 falls below a predetermined threshold and/or upon determining that a threshold deviation between the actual speed 13182 and the target speed 13181 is reached or passed, a reduction reaction 13194 is initiated. As can be seen in the graph 13180 the actual speed 13182 gradually decreases 13193 after the second target speed is attempted. In at least one instance, the rate at which the actual speed 13182 decreases can trigger the reduction reaction. Nonetheless, the motor system reduces the target speed 13181 of the motor to one or more new reduced target speeds relative to the second target speed. In at least one instance, the target speed of the motor is reduced in steps. At such point, additional monitoring of the actual speed relative to the new target speeds can be performed so as to analyze the effect of the reduction reactions on the relative capacity of the motor and determine whether or not further adjustments are necessary.

Figure 32:
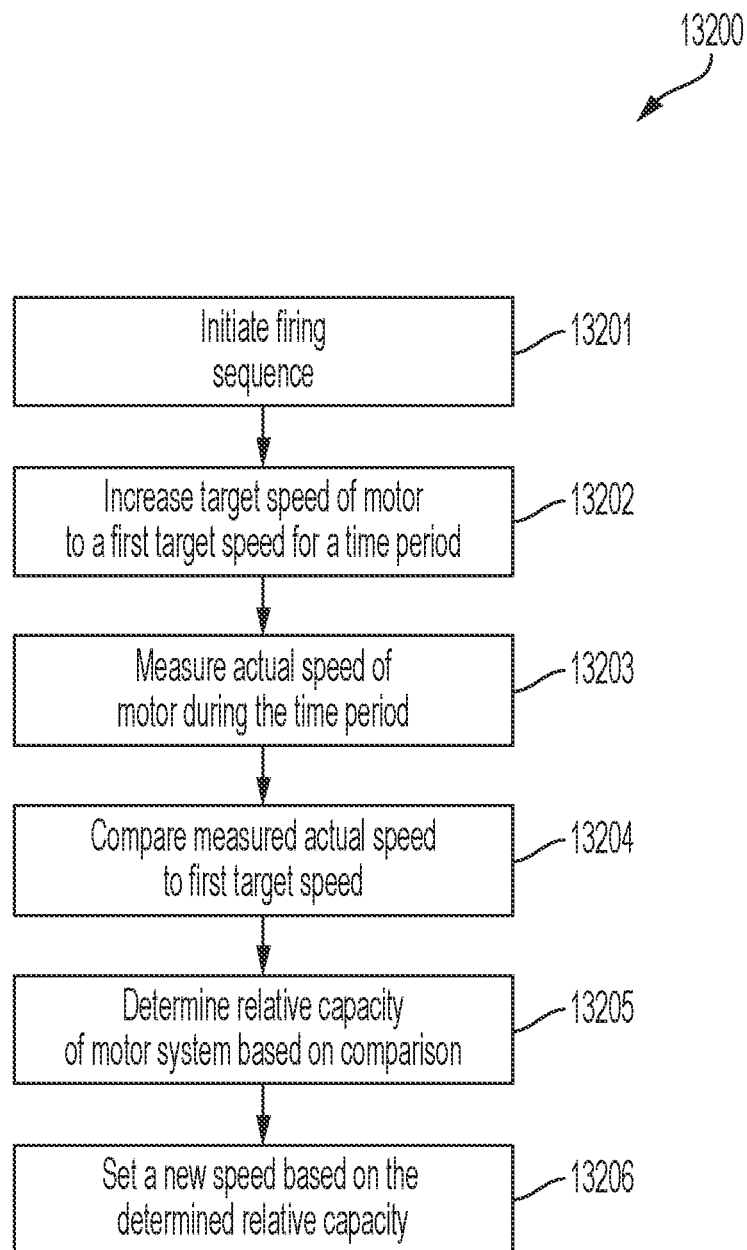
FIG. 32 is a logic flow chart depicting a process executable by a control circuit, wherein the process includes actions which interrogate a motor system to determine whether or not excess capacity exists within the motor system during a drive stroke of a drive train.

FIG. 32 is a logic flow chart depicting a process 13200 executable by a control circuit, such as the control circuit 1932 illustrated in FIG. 13 and/or the control circuit illustrated in FIG. 14, for example, configured to interrogate a motor system to determine whether or not excess capacity exists, for example, within the motor system during a firing sequence of a drive train. In this instance, the control circuit controls a firing sequence. The control circuit initiates 13201 the firing sequence, increases 13202 the target speed of the motor to a first target speed for a time period, measures 13203 the actual speed of the motor during the time period, compares 13204 the measured actual speed to the first target speed, determines 13205 the relative capacity of the motor system based on the comparison 13204, and sets 13206 a new speed based on the determined 13205 relative capacity. In at least one instance, the new speed is equal to the first target speed.

As discussed herein, a motor control circuit can perform the interrogation actions and/or reactions during a closure stroke and/or a firing stroke. The motor control circuit can also measure the speed of the motor in response to the increase in target speed during any suitable time period. The time period of each interrogation, or sensory, action may be predetermined and/or preselected. The time period of each interrogation action may vary from one interrogation action to the next. Comparing the target speed to the actual speed can involve analyzing the percent deviation between the target speed and the actual speed. In at least one instance, a fixed threshold speed is utilized to determine whether or not to perform additional interrogation actions or set a new speed. A pause can be utilized between interrogation actions. In at least one instance, no pause is utilized. In at least one instance, a pause may include a time period during which no interrogation actions are performed. In at least one instance, a pause may include a pause in motion of a firing member, for example, between interrogation actions. In at least one instance, the motor system automatically interrogates the relative capacity of the motor system during an entire stroke of the drive train in an effort to maximum the efficiency of the motor system throughout the entire stroke. In such an instance, a series of speed increases and decreases can occur throughout the stroke.

The control circuits disclosed herein can employ any of the steps and/or actions disclosed herein. The processes can be performed by any suitable components such as those disclosed in FIGS. 13 and 14. The processes disclosed herein can be performed utilizing any suitable drive train such as those disclosed herein in FIGS. 1-12, for example. The processes executable by a control circuit may include any suitable additional steps and/or actions, eliminate one or more steps and/or actions, and/or modify one or more of the steps and/or actions according to any of the scenarios discussed herein.

As discussed herein, a motor control circuit can be configured to perform any combination of and any number of sensory actions, interrogation actions, and/or functional actions, among others in an effort to control the speed, for example, of a motor of a motor system during a drive stroke of a drive train of the motor system. In at least one instance, these actions can be referred to as speed control actions. While speed is one variable capable of being controlled, adjusted, and/or monitored during these actions, any suitable variable can be used such as those disclosed herein, for example. In at least one instance, the outcome of each of these actions can be utilized to modify future actions and/or trigger other events, as discussed in greater detail below. Functional actions may be automatically triggered by one or more events and/or manually triggered by a user. For example, a user may manually trigger a speed increase during a drive stroke at which point a motor control circuit can be configured to increase the target speed of the motor and determine if the target speed can be and/or is achieved. Reactions to the manual increase in speed can include any suitable reactions such as those disclosed herein.

In at least one instance, further speed adaptations and/or speed control actions can be halted if one or more conditions are satisfied as a result of one or more previous actions. The outcomes, or results, of the previous actions can be constantly monitored. In at least one instance, the outcomes, or results, include whether or not the target speed of the previous action was achieved or the target speed was not achieved. Not achieving the target speed can be considered a failed action, for example. In at least one instance, the outcome, or result, includes whether or not the target speed of the previous action was achieved within a predefined deviation percentage, and/or the magnitude of failure and/or success of the previous action. In at least one instance, further actions can be halted temporarily and/or permanently, for example. In at least one instance, further actions to automatically control the speed of a motor can be automatically and/or manually re-activated. In at least one instance, further actions are automatically reactivated when a new firing stroke is initiated, for example.

In various instances, based on previous speed control action outcomes, or results, a motor control circuit can be configured to prevent further speed control actions from occurring whether triggered automatically and/or manually for a predetermined time period. In at least one instance, the motor control circuit is configured to prevent further speed control actions from occurring automatically but not manually or from occurring manually but not automatically.

Figure 33:
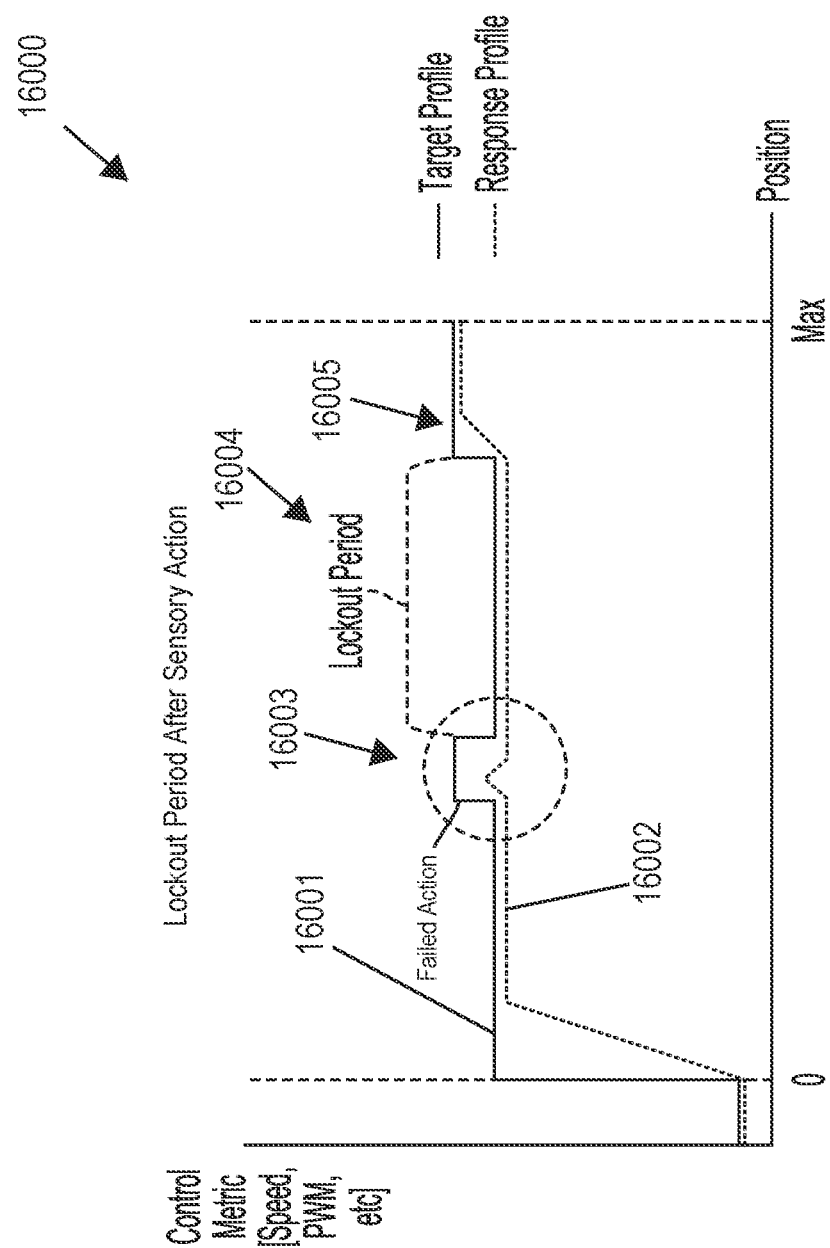
FIG. 33 is a graph depicting a firing stroke performed by a motor control circuit of a motor system, wherein the motor control circuit employs a lockout time period after a failed sensory action to prevent a subsequent action from occurring during the lockout time period.

Prevention of further speed control actions, or motor control adjustment actions, from occurring can protect from oscillation and/or hysteresis, for example, where without a pause, or lockout time period, after a previous action, a motor control circuit can incidentally perform undesirable adjustments based on a default control algorithm, for example. In at least one instance, a motor control circuit is configured to lockout any adjustment action from occurring during a lockout time period after a failed action occurs (a target speed was not achieved, for example). FIG. 33 depicts a graph 16000 depicting an example firing stroke performed by a motor control circuit of a motor system where target speed 16001 and actual monitored speed 16002 are illustrated. As can be seen in the graph 16000, the motor control circuit performs a sensory, or functional, action 16003 attempting to increase the speed of the motor to a new target speed 16001. The actual speed 16002 is monitored and it is determined that there is not capacity to run the motor system at the new target speed. The target speed 16001 is reverted back to the speed prior to the new target speed. As disclosed herein, the success of the sensory action can be referred to the actual speed reaching a desired percentage of the new target speed, for example. A failure of the sensory action can be referred to the actual speed not reaching a desired percentage of the new target speed. In at least one instance, a successful sensory action indicates that there exists excess capacity to permit the motor system to run at the new target speed. In at least one instance, a failed sensory action indicates there does not exist excess capacity to run the motor system at the new target speed.

As can be seen in FIG. 33, the motor control circuit employs a lockout time period 16004 configured to prevent any subsequent actions from occurring during the lockout time period 16004. In at least one instance, the lockout time period 16004 is predefined. In at least one instance, the magnitude of the lockout time period depends on one or more variables of the outcome of the previous failed sensory action. For example, if the magnitude of the previous sensory action fails by a large margin, the lockout time period may be longer as compared to if the sensory action fails by a smaller margin. The magnitude of the failure can be measured in percent deviation as discussed herein. Deviation thresholds can be utilized to determine the length of the lockout time period. After the lockout time period, one or more additional actions 16005 can be performed. In at least one instance, the number of additional actions which can be performed and/or the magnitude of the additional actions which can be performed is limited based on the failed sensory action where, if no failed sensory action occurred, additional actions may not be limited in any way. In at least one instance, additional actions are not limited regardless of the occurrence of a failed sensory action, for example.

In at least one instance, the length of the timeout, or lockout time period, depends on a current speed of the motor. For example, the magnitude of the current speed of the motor can be used to determine the magnitude of the lockout time period. In at least one instance, a faster speed triggers a longer timeout period whereas a slower speed triggers a shorter lockout time period. In at least one instance, a faster speed triggers a shorter timeout period and a slower speed triggers a longer lockout time. In various instances, the success status of one or more previous speed control actions triggers different length timeout periods. For example, a lockout period may be employed during a drive stroke for a successful speed control action and an unsuccessful, or failed, speed control action. In such an instance, the lockout time period may be shorter for the successful speed control action as compared to the lockout time for failed speed control action.

In at least one instance, a prevention, or lockout time period, can prevent inadvertent re-shifting immediately after the motor control circuit intentionally performs a functional action. For example, a user can choose to increase the speed of a motor from a first speed to a second speed. The motor control circuit may determine that the second speed was not achieved. However, instead of reverting back to the first speed, the motor control circuit can employ a lockout time period as result of the manual input change of speed so as not to automatically undo the speed change desired by the user, for example. In at least one instance, the motor control circuit is configured to undo the user desired speed change regardless of the fact that the user manually inputted the speed change. In at least one instance, further intentional manual speed change inputs are prohibited during the lockout time period.

In at least one instance, a motor control circuit is configured to disable automatic speed control after a predetermined number of lockout time periods are triggered during a firing stroke. Such an arrangement can prevent a motor system from continuously being adjusted when a certain adjustment constantly results in a failed action.

In at least one instance, a lockout distance period is employed by a motor control circuit. For example, after a failed action occurs, the motor control circuit is configured to prevent any speed control action from occurring during a predefined distance of a drive stroke. In other words, when the firing member is determined to be within a lockout zone between position A and position B, for example, further adjustment actions are prohibited. For example, the motor control circuit can prevent any speed control actions, or adjustments, from occurring for the following 10 mm after the previous failed action is complete. The magnitude of the lockout distance may vary based on the magnitude of the failed action, for example. For example, if the actual speed of the motor deviates from the target speed above a threshold deviation percentage, the lockout distance can be set at a first distance. If the actual speed of the motor deviates from the target speed below a threshold deviation percentage but still fails, the lockout distance can be set at a second distance which is less than the first distance. In at least one instance, the second distance is half of the first distance.

In at least one instance, speed adjustment actions are prohibited from occurring prior to the staple firing stroke. In at least one instance, speed adjustment actions are prohibited from occurring between an unfired position of a firing member and a defeated lockout position of the firing member. The defeated lockout position may be the position at and/or just after the firing member has passed a lockout of a surgical stapling instrument such as, for example, a no cartridge lockout and/or a spent cartridge lockout. In at least one instance, speed adjustments are prohibited from occurring when the firing member is positioned within a zone immediately preceding an end of the staple firing stroke and/or the end of the staple cartridge.

Firing members discussed herein may refer to any suitable component such as, for example, any combination of an I-beam of a firing shaft and/or any portion thereof, a sled configured to eject staples from a staple cartridge and/or any portion thereof, a firing shaft and/or any portion thereof, a firing rod and/or any portion thereof, and/or any portion of a firing drive train.

In at least one instance, the average actual speed monitored during the time period of the sensory, functional, and/or interrogation action can be utilized to determine if the target speed is achieved or not achieved. In at least one instance, the maximum actual speed monitored during the time period of the sensory, functional, and/or interrogation action can be utilized to determine if the target speed is achieved or not achieved. In at least one instance, the minimum actual speed monitored during the time period of the sensory, functional, and/or interrogation action can be utilized to determine if the target speed is achieved or not achieved. In at least one instance, any combination of the aforementioned metrics can be utilized to determine if the target speed is achieved or not achieved. Predetermined deviation percentages can be stored in a memory and can be accessed when determining if the target speed is achieved or not achieved. Predetermined deviation percentages can change for different types, such as length and/or staple height, for example, of staple cartridges being fired.

In various instances, a motor control circuit is configured to halt, or prohibit, motor control parameter adjustments (such as PID controller parameters, for example) during the lockout time periods and/or lockout distance. In at least one instance, PID controller parameter adjustments could be frozen for a period of time which is the same as or different than the predefined lockout time period. In at least one instance, the thresholds and/or conditions required to be met by the motor control circuit to change one or more of the PID controller parameters during a drive stroke can be widened or softened, for example, to minimize the number of noticeable, or perceptible, re-adjustments of speed after a failed action. For example, a greater error may be required in order to trigger an adjustment of one or more PID controller parameters after a failed action than an error required in order to trigger an adjustment prior to the failed action.

In various instances, the motor control circuit is configured to learn over time and adjust future speed control actions of future drive strokes according to previous drive stroke data. In at least one instance, certain outputs monitored during a drive stroke can be utilized to identify opportunities to update feedforward network weights. The network weights can include thresholds. The thresholds can indicate an out of bounds condition.

In at least one instance, a motor control circuit is configured to revert the motor system back to a last known good state. This can be triggered by a failed action, for example. In at least one instance, the last known good state includes a state where the motor system was running adequately and not near and/or at full capacity.

In at least one instance, a motor control circuit is configured to perform speed control actions during firing member advancement and/or firing member retraction.

In various instances, a motor control circuit is configured to alter a speed control algorithm in response to a cumulative sequence of events and/or triggers, for example. In at least one instance, a predetermined number of failed actions have to occur, failed actions have to occur at a predetermined frequency, and/or a predetermined plurality of failed actions have to fail by a certain percentage before the motor control circuit reacts. Any suitable reaction can occur such as those disclosed herein. For example, parameters of further actions can be adjusted, lockout time periods and/or lockout zones can be employed, PID motor controller parameters can be adjusted etc. In at least one instance, both a sequence of events must occur in addition to a predetermined single event to cause the motor control circuit to react. Such an arrangement can provide greater situation-specific control of a motor system during a firing stroke. For example, during a firing stroke, a predetermined plurality of sensory actions may fail. While this alone will not trigger further action, this in combination with a single event such as, for example, a single sensory action fails below a certain threshold, may trigger a cool down period or a pause. The sequence of failed actions in addition to the larger failed action may indicate that the motor was struggling to perform the firing stroke to begin with and, at the detection of the larger failed action, indicated to the motor control circuit that the motor may have been overheating and/or operating beyond its maximum, or optimal, capacity. The automatic activation of a cool down period can allow tissue to relax as well as the motor to cool down, for example.

In various instances, a motor control circuit is configured to utilize events of previous firings of an instrument to adjust and/or alter speed control algorithms of a subsequent firing. For example, a first cartridge may be used with an instrument and, during the firing of the first cartridge, data collected about the outcomes of various speed control actions, for example, performed during the firing stroke of the first cartridge. The motor control circuit can then be configured to adjust one or more parameters of the firing stroke of a second cartridge to be fired based on the data collected about the outcomes of the various speed control actions performed during firing of the first cartridge. Such an arrangement can allow a motor control circuit of a specific motor system to be more efficiently operated between multiple different staple cartridges by monitoring events of each cartridge firing and optimizing each subsequent firing based on the performance of previous firings.

One example of a motor control circuit utilizing data from multiple different firings as discussed herein is discussed below. A motor system of a surgical instrument fires two different staple cartridges. At the 50 mm position the motor control circuit detects an irregularity in the firing stroke. In at least one instance, there is a speed discrepancy detected at the 50 mm mark. In at least one instance, there is a displacement discrepancy detected between the motor and the firing member at the 50 mm mark. The motor control circuit is configured to adjust any subsequent firing of another staple cartridge to increase the speed of the motor prior to the 50 mm mark such as, for example, at the 45 mm mark. Such an increase in speed can ensure that for any subsequent firing with that instrument that the motor system does not lag and/or compensates for the known, recurring, irregularity at the 50 mm mark of that instrument. In at least one instance, the motor control circuit is configured to perform a speed burst at and/or near the 50 mm mark. In at least one instance, the motor control circuit is configured to pulse an additional burst of power to the motor just before the 50 mm mark and only for a short period of time. In at least one instance, the motor control circuit is configured to adjust a speed control algorithm of subsequent firings in an effort to maintain a constant speed through the 50 mm mark and eliminate the irregular stroke. Such a configuration can overcome recurring stroke irregularities between firings which may distract a user, cause abnormal cutting of tissue, and/or unpredictable staple formation.

In various instances, a predetermined level of repeatability threshold must be met before speed control adjustments are made to subsequent firing strokes. For example, a motor control circuit can determine a stroke irregularity, or anomaly, at a 30 mm mark during both an advancement stroke and a retraction stroke. This may indicate a location where interfacing components (such as I-beam and channel and/or anvil, for example) have a tighter interference. Such a tighter interference can be caused by tissue ingress and/or a manufacturing anomaly, for example, which are increasing forces to fire at this location. Because of this stroke irregularity, staple formation and/or tissue cutting may not be as predictable. In at least one instance, a motor control circuit adjusts parameters for all subsequent strokes at this location to reduce the force to fire at this location in an effort to more predictably form staples and/or cut tissue, for example. In at least one instance, the adjusted parameters could be reverted back to normal after passing this location; either during advancement and/or during retraction, for example. In at least one instance, the motor control circuit is configured to anticipate the previously detected stroke irregularity during subsequent strokes by adjusting parameters of subsequent strokes to specifically look for the stroke irregularity but not taking any action unless the newly monitored irregularity is detected. In at least one instance, spikes in force are monitored and associated with stroke irregularities.

In various instances, a sequence of stroke irregularities are detectable and acted upon to adjust motor control of a drive stroke. For example, a motor control circuit can detect a plurality of force spikes within the motor system each time a staple leg contacts an anvil to be formed. In at least one instance, this initial contact can cause the largest spike in the motor system within the staple formation process which can be detectable and stand out in a plurality of force spikes of a firing stroke. This spike can be detected by the motor control circuit as being the highest peak force during the formation of each staple each of which include a known location relative to the firing stroke. In at least one instance, if the spike detected for a staple, or a plurality of staples (sequence of stroke irregularities), exceeds a predetermined threshold, or predetermined threshold profile, the motor control circuit can perform one or more speed control actions to reduce the spike in force for each leg-anvil contact event. In at least one instance, the spike exceeding a threshold during initial leg-anvil contact could indicate that the leg is not hitting the anvil in an anticipated and/or desired location. Such a spike could indicate that tissue is being bunched up by the knife and pushing the staple legs distally relative to the anvil causing the tips of the staples to miss target pocket locations and, as a result, increasing the force to fire the staples and, also, causing staple malformation, for example. Reducing the speed of the motor to increase the likelihood of the tips of the staples contacting their intended target location can reduce the force to fire and increase the likelihood of proper staple formation.

In at least one instance, a motor control circuit is configured to monitor the number of failed/successful speed control actions and, once a predetermined number of failed/successful speed control actions occur, adjust a magnitude of subsequent speed control actions. For example, a motor control circuit can place a limit on target speeds of subsequent speed control actions when a predetermined number of failed actions occur. In at least one instance, a user can try to increase the speed of the motor by a certain amount; however, the motor control circuit can set a target speed threshold which cannot be surpassed automatically and/or manually, for example. If the user tries to increase the speed of the motor beyond the target speed threshold which is a limit triggered by a sequence of prior failed speed control actions, the motor control circuit can automatically adjust the actual target speed down to the threshold target speed and attempt to increase the speed of the motor to the threshold target speed. In at least one instance, such a configuration can prevent a user and/or a motor control circuit from increasing the speed of an already struggling motor beyond a certain threshold based on a plurality of previously failed speed increase actions, for example. In at least one instance, after a predetermined plurality of successful speed control actions performed with the newly set limit threshold target speed, the limit threshold target speed can be removed, or lifted. In at least one instance, the limit threshold target speed cannot be lifted and/or removed until a new staple cartridge is installed and/or a new firing stroke is performed. In at least one instance, the limit threshold target speed is never lifted for that surgical instrument.

In various instances, a motor control circuit is configured to monitor a pattern of outcomes of speed control actions and based on the pattern, make adjustments to one or more future speed control actions based on the monitored pattern. For example, during a first firing, a plurality of failed actions can occur. If the degree of failure increases for each subsequent failed action to correspond to a predetermined pattern of increased failure, the motor control circuit can detect the predetermined pattern of increased failure and adjust subsequent firings accordingly. In at least one instance, magnitudes and/or frequency of speed control actions of subsequent firings are adjusted. In at least one instance, the motor control circuit is configured to place a limit on the number of subsequent firings permitted of the surgical instrument based on the detected predetermined pattern of increased failure. In at least one instance, a lockout time period is employed and the magnitude, or length, of the lockout time period can be increased based on the detected predetermined pattern of increased failure. Such a configuration can provide an amount of time for the motor system to reduce its power use and/or mechanical energy burden.

In various instances, a motor control circuit is configured to adjust the frequency of subsequent sensory actions based on detecting a predetermined, cumulative, amount of sensory action failures. For example, after detecting the predetermined amount of sensory action failures, the motor control circuit can reduce the frequency at which speed control adjustments are automatically and/or manually made for the rest of the firing and/or subsequent firings. In at least one instance, the motor control circuit is configured to adjust the definition of a failed action for subsequent firings or the rest of a firing based on detecting a predetermined, cumulative, amount of sensory action failures. For example, the motor control circuit can increase the threshold required to be considered a successful sensory action, for example.

Figure 34:
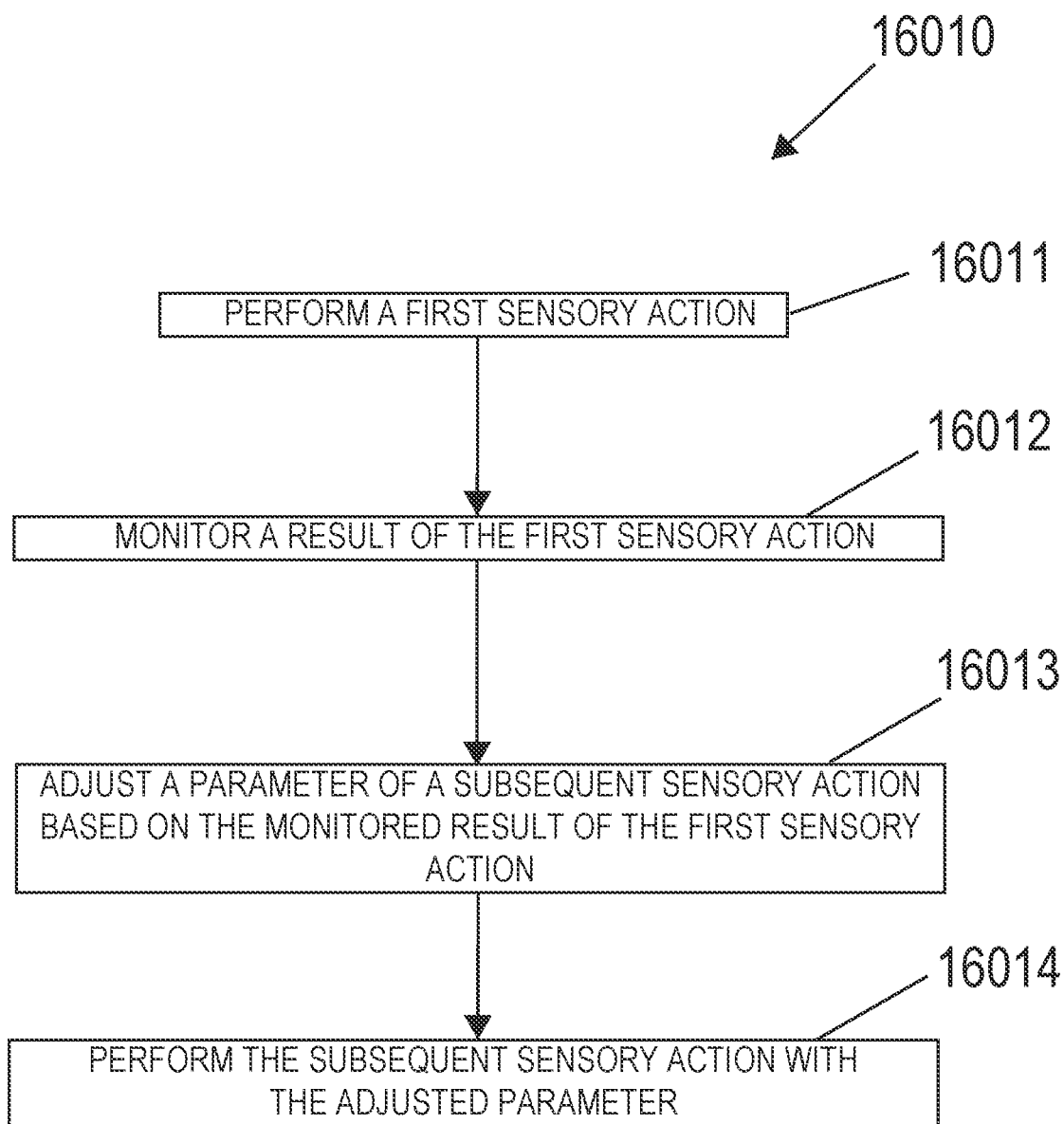
FIG. 34 is a logic flow chart depicting a process executable by a control circuit for use in a surgical instrument system, wherein the control circuit is configured to adjust a parameter of a subsequent sensory action, wherein the adjustment is based on a monitored result of a first sensory action.

FIG. 34 is a logic flow chart depicting a process 16010 executable by a motor control circuit, such as the control circuit 1932 illustrated in FIG. 13 and/or the control circuit illustrated in FIG. 14, for example, for use in a surgical instrument system such as those disclosed herein. The motor control circuit is configured to perform 16011 a first sensory action. In at least one instance, the first sensory action is performed during a staple firing stroke. The sensory action may be manually initiated and/or automatically initiated. In at least one instance, the sensory action is performed in an attempt to increase the speed of the motor. The motor control circuit is configured to monitor 16012 the result of the first sensory action. In at least one instance, the monitored result can include any suitable outcome, or response, of the surgical system as a result of the first sensory action. In at least one instance, the monitored result includes a success status of the first sensory action and/or a percent deviation between a target speed relative to an actual speed of the motor, for example. The motor control circuit is further configured to adjust, or modify, 16013 a parameter of a subsequent sensory action based on the monitored result of the first sensory action. Any suitable parameter can be adjusted such as, for example, the timing of the subsequent sensory action (length of the action, when the action occurs relative to the stroke, etc.), the target of the subsequent sensory action (target speed, target displacement, etc.), and/or the existence of the subsequent sensory action (perform the subsequent sensory action vs. do not perform the subsequent sensory action). The motor control circuit is further configured to perform 16014 the subsequent sensory action with the adjusted parameter. In at least one instance, the subsequent sensory action is performed during the current stroke. In at least one instance, the subsequent sensory action is performed during a subsequent stroke of the surgical instrument system.

Figure 35:
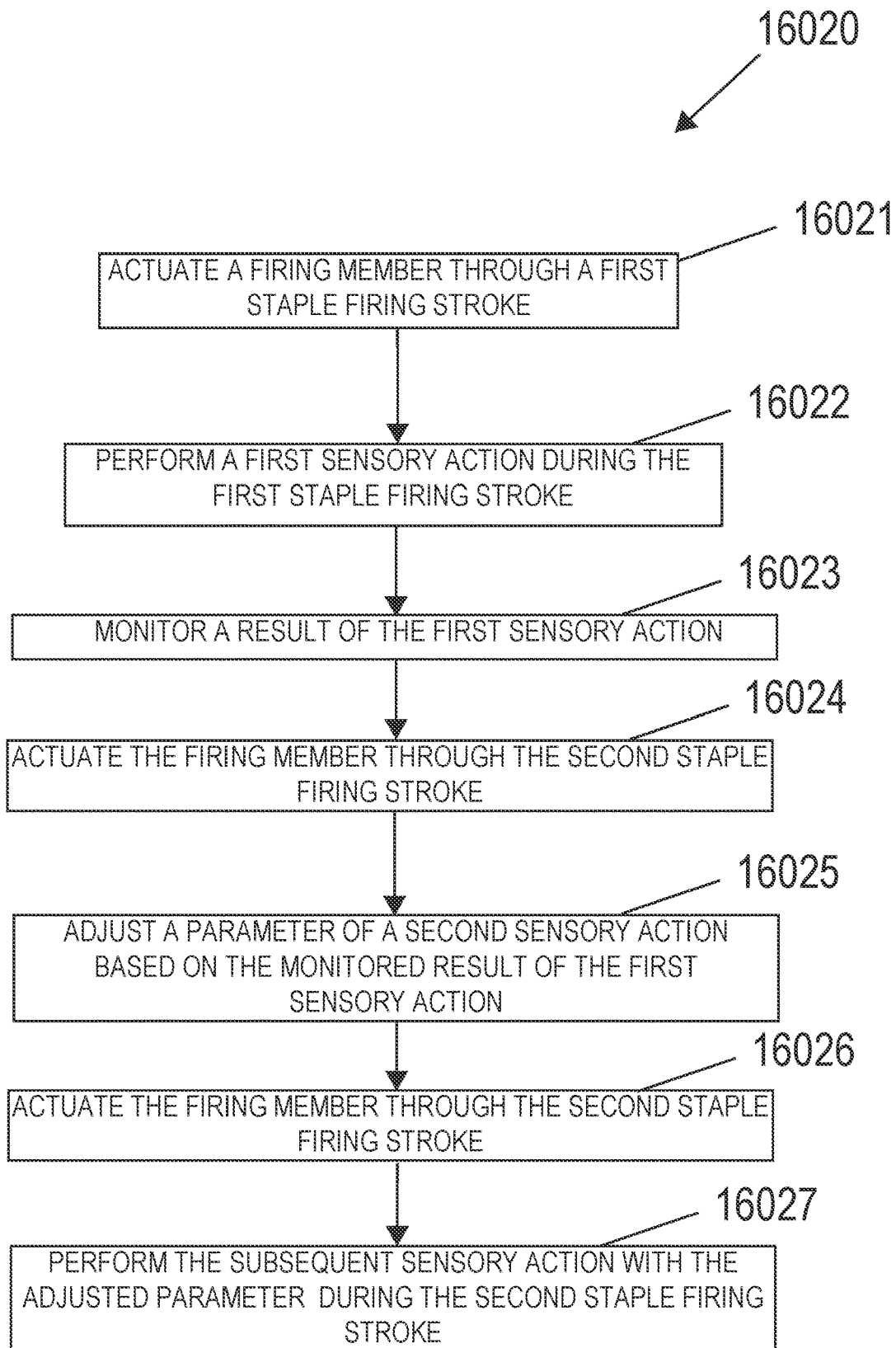
FIG. 35 is a logic flow chart depicting a process executable by control circuit for use in a surgical instrument system, wherein the control circuit is configured to adjust a parameter of one or more sensory actions performed during a second staple firing stroke, and wherein the adjustment is based on a monitored result of a first sensory action performed during a first staple firing stroke.

FIG. 35 is a logic flow chart depicting a process 16020 executable by a motor control circuit, such as the control circuit 1932 illustrated in FIG. 13 and/or the control circuit illustrated in FIG. 14, for example, for use in a surgical instrument system such as those described herein. The motor control circuit is configured to actuate 16021 a firing member through a first staple firing stroke, perform 16022 a first sensory action during the first staple firing stroke, and monitor 16023 a result of the first sensory action. The motor control circuit is further configured to actuate 16024 the firing member through a second staple firing stroke, adjust 16025 a parameter of a second sensory action based on the monitored result of the first sensory action, and actuate 16026 the firing member through the second staple firing stroke. The motor control circuit is further configured to perform 16027 the subsequent sensory action with the adjusted parameter during the second staple firing stroke.

Figure 36:
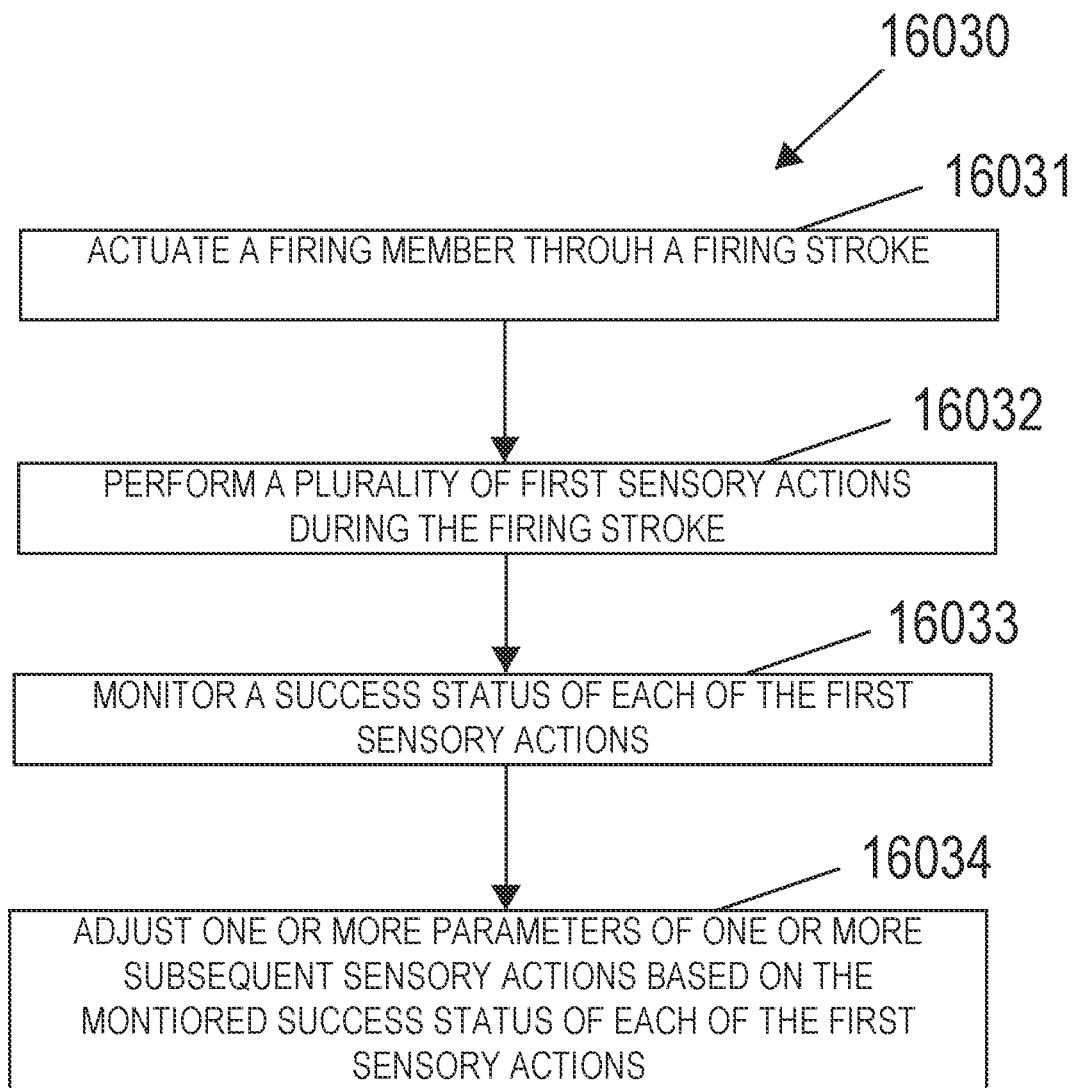
FIG. 36 is a logic flow chart depicting a process executable by control circuit for use in a surgical instrument system, wherein the control circuit is configured to adjust a parameter of one or more subsequent sensory actions, wherein the adjustment is based on a monitored success status of one or more first sensory actions.

FIG. 36 is a logic flow chart depicting a process 16030 executable by a motor control circuit, such as the control circuit 1932 illustrated in FIG. 13 and/or the control circuit illustrated in FIG. 14, for example, for use in a surgical instrument system such as those described herein. The motor control circuit is configured to actuate 16031 a firing member through a firing stroke, perform 16032 a plurality of first sensory actions during the firing stroke, and monitor 16033 a success status of each of the first sensory actions. The motor control circuit is further configured to adjust 16034 one or more parameters of one or more subsequent sensory actions based on the monitored success status of each of the first sensory actions. In at least one instance, adjustments are based on how many previous sensory actions failed as compared to succeeded. In at least one instance, the control circuit is further configured to adjust the parameter according to a first adjustment profile upon monitoring a threshold number of successful first sensory actions. In at least one instance, the threshold number can be automatically determined and/or manually set.

In various instances, a motor control circuit is utilized to control a motor of a motor system including a drive train such as, for example, a firing drive train. In at least one instance, the motor control circuit is operable within a set of adjustable parameters. For example, the motor control circuit may set a minimum speed threshold at a first speed and a maximum speed threshold at a second speed which is greater than the first speed to begin a staple firing stroke. These threshold speeds, for example, can be adjusted and/or fine-tuned during the staple firing stroke of the motor system to optimize operation of the motor system and/or maximize the efficiency of the motor system within a single drive stroke in real-time. Various factors such as, for example, drive train backlash and/or heat loss within the motor can cause the motor system to run less efficiently. However, adjusting the adjustable parameters during the staple firing stroke can account, mitigate, and/or compensate for things like drive train backlash and/or heat loss within the motor, for example. The magnitude of the adjustment made to these threshold speeds can be based on a variety of factors. For instance, any suitable parameter or combination of parameters of the motor system can be monitored. In such an instance, a new threshold speed can be determined based on the magnitude of the monitored parameter and/or the rate at which the monitored parameter changes over a period time, for example. In at least one instance, multiple monitored parameters are compared and analyzed to determine an appropriate adjustment to the adjustable parameters.

In at least one instance, a maximum motor current limit is set by a motor control circuit to limit the amount of current drawn by the motor to a predetermined threshold current. In at least one instance, the predetermined threshold current can be changed in different portions of a drive stroke such as, for example, a staple firing stroke. For example, a first portion of the stroke can include a first threshold current limit and a second portion of the stroke can include a second threshold current limit which is different than the first threshold current limit. In at least one instance, a lower current limit threshold is utilized in the beginning of a drive stroke where a drive member may encounter a lockout condition so as to prevent a relative large amount of current draw during a lockout condition which is detectable based on a small uptick in current and, thus does not need large amounts of current that can unnecessarily overstress the system, for example. Such an arrangement may provide some protection to the drive train through the beginning of a firing stroke. In at least one instance, a threshold current limit for the retraction stroke of a drive member is set relatively high as compared to a threshold current limit set for an advancement part of the stroke so as to ensure the motor can retract the drive member, even if the threshold current limit was met during the advancement part of the stroke. This can be as result of having a threshold current limit for the retraction stroke which is always greater than a maximum threshold current limit for the advancement stroke. In at least one instance, if the drive member cannot retract fully, the jaws of an end effector may be stuck clamped.

Figure 37:
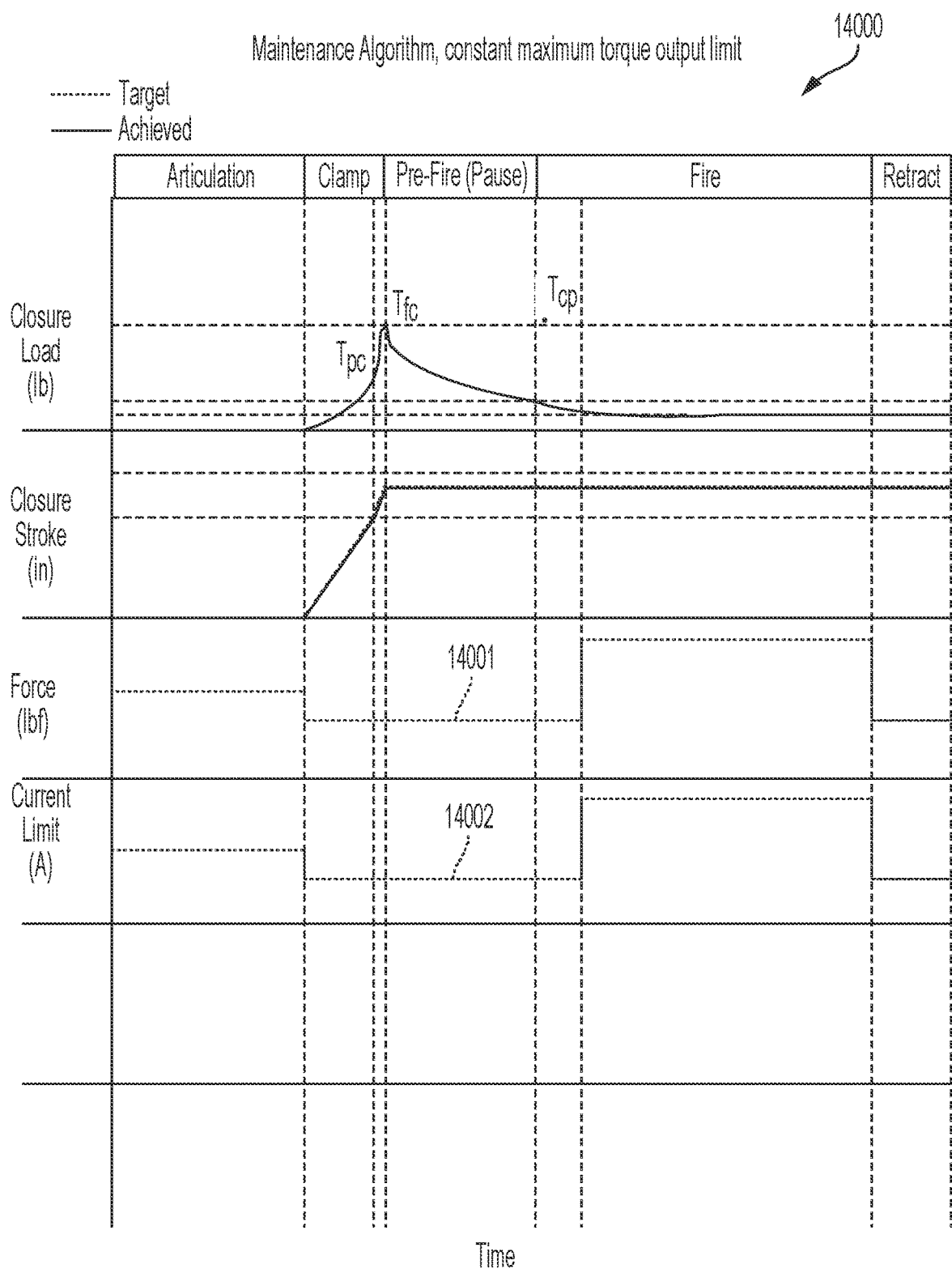
FIG. 37 is a graph depicting a firing stroke performed by a motor system including a motor, a drive train, and a motor control circuit, wherein the motor control circuit is configured to set maximum torque output limits during different periods of the firing stroke.

FIG. 37 is a graph 14000 depicting various parameters of a motor control algorithm executable by a control circuit of a staple firing stroke. The graph 14000 illustrates motor torque limits 14001 and motor current limits 14002 during various stages of use of a surgical instrument system. As can be seen in the graph 14000, the torque limits 14001 and current limits 14002 vary through different portions of the drive stroke. In at least one instance, the torque limit 14001 and the current limit 14002 peak during the staple firing stroke portion of the drive stroke. As discussed herein, the limits 14001, 14002 can be adjusted during the drive stroke based on at least one monitored parameter and at a variety of different times throughout the drive stroke to fine-tune the limits 14001, 14002 in real time during the drive stroke.

Figure 38:
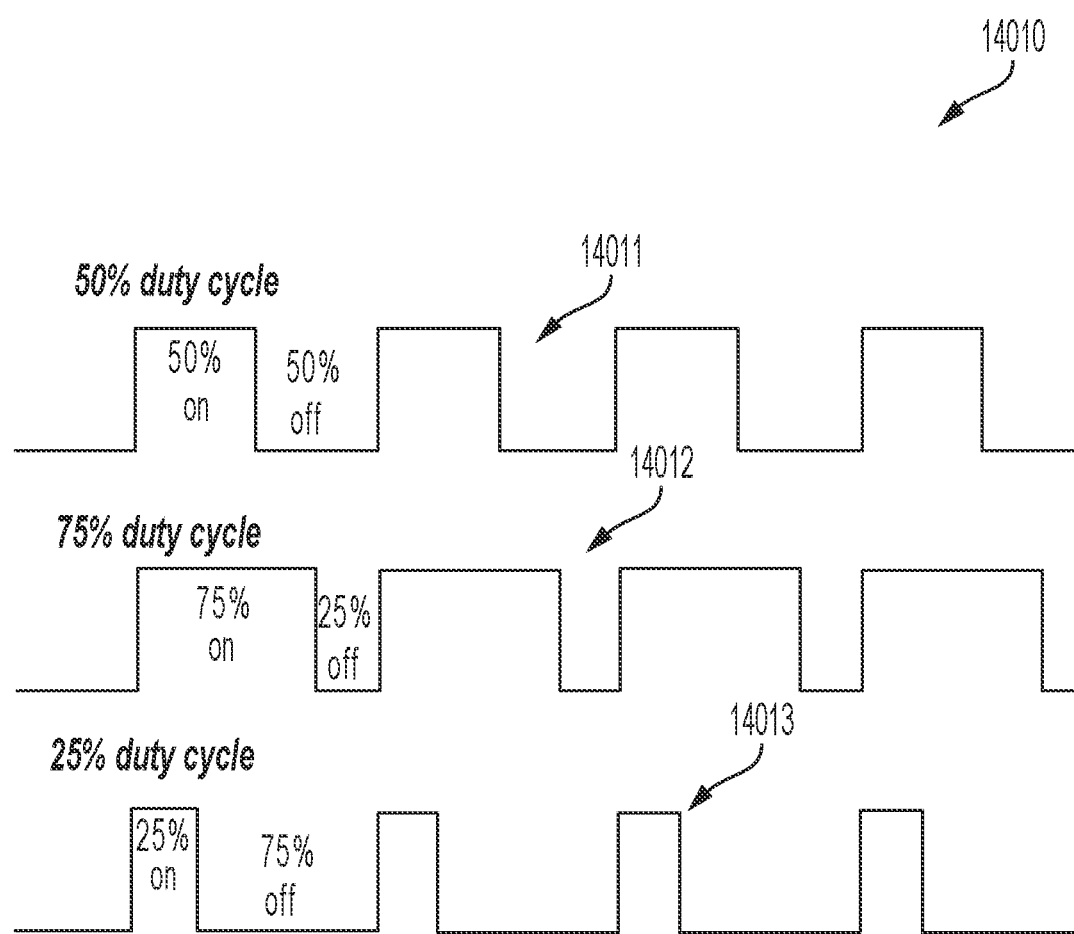
FIG. 38 is a schematic representation of different motor duty cycles for a motor of a surgical instrument.

In various instances, duty cycle ranges of pulse width modulation (PWM) motor control are set by a motor control circuit. In at least one instance, the motor duty cycle ranges are adjusted during a drive stroke based on one or more monitored parameters. FIG. 38 illustrates a plurality of motor duty cycles 14010. In at least one instance, a motor control circuit employs a 25% minimum duty cycle 14013 so that the motor runs with at least a 25% duty cycle and the motor control circuit employs a 75% optimal duty cycle 14012 so that the motor does not run beyond a 75% duty cycle. If the motor control circuit attempts to adjust the speed of the motor, for example, which would cause the motor duty cycle to surpass 75%, the motor control circuit would determine that the 75% duty cycle threshold would be met and/or exceeded and thus the adjustment would not be made and/or a magnitude of the adjustment is altered so that the adjustment would not cause the 75% duty cycle threshold to be met and/or exceeded. An optimal duty cycle 14011 may include 50%, for example. In at least one instance, the motor control circuit is configured to base any speed adjustments based on the optimal duty cycle 14011. Adjustment of PWM duty cycles as disclosed herein can be referred to as PWM speed control.

In various instances, a motor performance curve of the motor is utilized to determine an optimal duty cycle range. In at least one instance, the motor performance curve of the motor is utilized to set a maximum duty cycle threshold and a minimum duty cycle threshold. The motor performance curve can be used to determine the most efficient range of duty cycles. In at least one instance, the minimum duty cycle limit is set based on frictional losses and/or inertial properties of the drive train in an effort to eliminate jerkiness, oscillation, and/or vibration of the motor system. In at least one instance, the maximum duty cycle limit is set based on heat generation of the motor. Further to the above, an older motor may generate more heat over time. In such an instance, the maximum duty cycle limit is adjusted for the increased heat generation owing to the age and/or overall life of the motor, or motor performance degradation over time, for example. Setting the maximum duty cycle limit in such a manner can consistently minimize heat generation in the motor between strokes and/or even during a single stroke, for example. In at least one instance, an ideal range of duty cycle limits includes a maximum duty cycle limit of about 85% and a minimum duty cycle limit of about 25%. In at least one instance, a maximum range of duty limit includes a maximum duty cycle limit of about 90% and a minimum duty cycle limit of about 10%.

In at least one instance, a motor stall condition is set and, once detected, a control circuit can turn off the motor after a predetermined amount of non-moving torque application. For example, if the firing member encounters a piece of tissue which is so thick that the firing member stops moving, the predetermined amount of non-moving torque can be exceeded, which causes the control circuit to cause the motor to shut down reducing inadvertent heat generation upon meeting the motor stall condition.

In at least one instance, motor duty cycle and/or displacement are used to adapt and/or select target motor speeds. For example, a decreased target motor speed may be triggered in an instance where the motor duty cycle is relatively high in percentage and/or magnitude in an attempt to reduce the percentage and/or magnitude of the motor duty cycle. Similarly, an increased target speed may be triggered in an instance where the motor duty cycle is relatively low in percentage and/or magnitude in attempt to increase the utilization of the motor system, for example.

Figure 39:
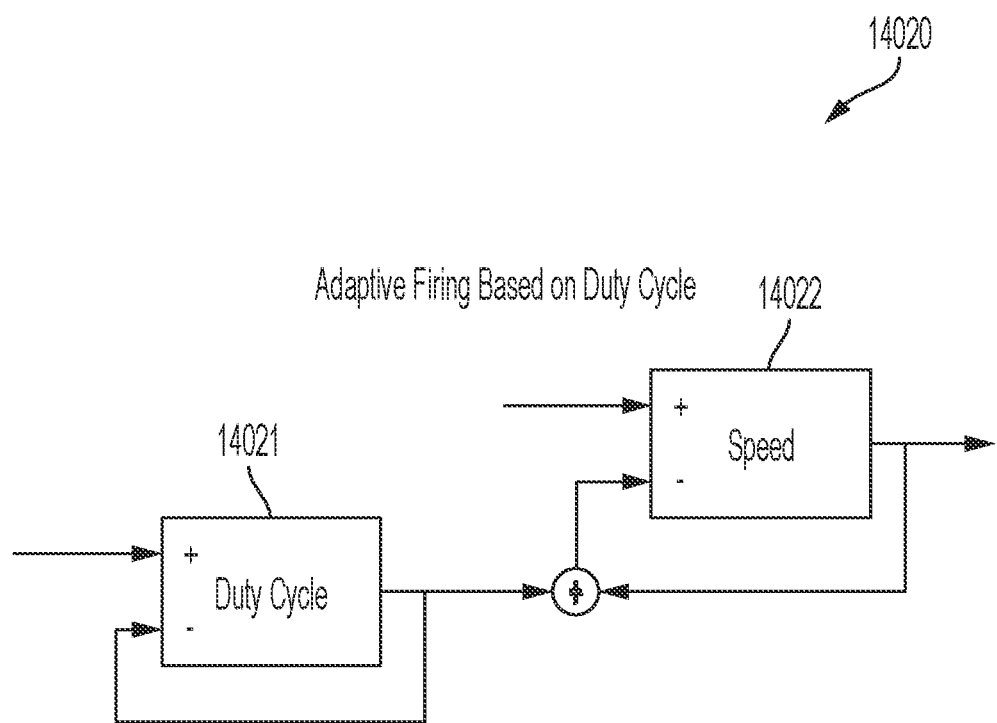
FIG. 39 depicts a control process of a motor control circuit of a surgical instrument configured to utilize both monitored motor duty cycle and monitored motor speed and/or firing member speed as inputs for adjusting the speed of the motor during a drive stroke.

FIG. 39 depicts a control process 14020 configured to utilize both monitored duty cycle 14021 and monitored motor speed and/or firing member speed, for example, 14022 as inputs for adjusting the speed of the motor during a drive stroke, for example. For example, the higher the duty cycle utilization is (for example, close to maximum, or optimal, capacity, for example) when a target velocity and/or target displacement, for example, is not achieved, the higher the magnitude of the speed decrease adjustment will be in an effort to bring the motor system well within its optimal operating range in response to the missed target. Similarly, in at least one instance, if a lower utilization is detected when a target velocity or target displacement is missed, the magnitude of the speed increase adjustment is selected based on the determined level of utilization of the motor system.

One situational non-limiting example will be described. A firing member is moving at 10 mm/sec, for example, in thick tissue and is succeeding in meeting its displacement and/or speed target(s), for example. The firing member then encounters a calcified portion of extra thick tissue and misses one or more displacement targets, for example. At such point, the motor control circuit determines that the motor should be slowed down to allow the tissue to relax, settle, loosen, and/or creep in front of the firing member such as, for example, the cutting knife. In other words, slowing the firing member down relieves some of the load on the firing member applied by a tight, bunched up portion, for example, of extra thick portion of tissue. In at least one instance, it can be determined that the duty cycle is also already at nearly 100% when the displacement target was missed indicating that the motor system may have been already been nearly missing its displacement targets prior to the actual detection of the missed displacement target. The system can then slow the firing member down 150% of its target speed of 10 mm/sec, for example. Where the motor control circuit would have normally slowed the firing member down from 10 mm/sec to 7 mm/sec (a 3 mm/sec anticipated slow down action), the motor control circuit determines to slow down the firing member to 5.5 mm/sec (150% of the original 3 mm/sec anticipated slow down action—4.5%) because the motor system both missed the displacement target and the motor system was nearly at 100% utilization when the displacement target was missed.

In at least one instance, a motor control circuit is configured to set target travel lengths, or displacement targets, which the firing member is expected to travel during a predetermined time period. In such an instance, the motor control circuit, utilizing a PID controller, for example, can monitor the error terms (proportional, integral, and derivative terms, for example) and uses these error terms as inputs to the motor control circuit to make adjustments to the motor control. In at least one instance, the error terms include displacement error, velocity error, and overshoot error. Any combination of these errors terms can be utilized as inputs by a motor control circuit.

In at least one instance, one or more parameters are monitored during a firing stroke, for example, and are utilized as inputs into a motor control circuit including a PID controller, for example, for adjusting motor control.

In at least one instance, PID controller parameters, such as proportional, integral, and/or derivative, parameters are adjusted, or fine-tuned, based on one or moor monitored parameters within a motor system. Such monitored parameters can include motor response, firing member load, speed, displacement, and/or tissue properties, for example.

In at least one instance, a PID feedback control system includes a PID controller comprising a proportional element (P), an integral element (I), and a derivative element (D). The outputs of the P, I, D elements are summed by a summer, which provides the control variable to a process. The output of the process is the process variable. The summer calculates the difference between a desired set point and a measured process variable. The PID controller continuously calculates an error value (e.g., difference between closure force threshold and measured closure force) as the difference between a desired set point (e.g., closure force threshold) and a measured process variable (e.g., velocity and direction of closure tube) and applies a correction based on the proportional, integral, and derivative terms calculated by the proportional element (P), integral element (I), and derivative element (D), respectively. The PID controller attempts to minimize the error e(t) over time by adjustment of the control variable (e.g., velocity and direction of the closure tube).

In accordance with a PID algorithm, the "P" element accounts for present values of the error. For example, if the error is large and positive, the control output will also be large and positive. The error term is the difference between a reference, or target, speed, for example and an actual output speed. The "I" element accounts for past values of the error. For example, if the actual speed does not achieve the target speed over a period of time, the integral of the error will accumulate over time, and the controller will respond by applying a stronger action. The "D" element accounts for possible future trends of the error, based on its current rate of change. For example, continuing the P example above, when the large positive control output succeeds in bringing the error closer to zero, it also puts the process on a path to large negative error in the near future. In this case, the derivative turns negative and the D module reduces the strength of the action to prevent this overshoot. More detail of PID control of a surgical instrument system is disclosed in U.S. patent application Ser. No. 15/636,829, now U.S. Patent Application Publication No. 2021/0244407 entitled METHODS FOR CLOSED LOOP VELOCITY CONTROL FOR ROBOTIC SURGICAL INSTRUMENT, which is incorporated by reference herein in its entirety.

Fine tuning the PID controller parameters can provide greater motor control in a variety of scenarios. For example, the PID controller parameters can be adjusted corresponding to the type and/or thickness of tissue that is to be stapled and cut. In at least one instance the PID controller parameters can be adjusted based on the type of cartridge installed within an end effector, size of staples within the installed cartridge, and/or length of the installed cartridge, for example.

In at least one instance, an expected compressive clamping load (pressure owing to clamped tissue within a predefined tissue gap between the cartridge and the anvil) can dictate PID tuning, or control, parameters. For example, if the expected compressive clamping load is exceeded during the clamping stage of the end effector, the PID controller parameters can be adjusted accordingly to compensate. Similarly, if the excepted compressive clamping load is not exceeded during the clamping stage of the end effector, the PID controller parameters can be set accordingly or, in at least one instance, not adjusted from a preset parameter profile which was set prior to clamping the tissue.

In at least one instance, outcomes of anticipated stroke events can trigger one or more adjustments to the PID controller parameters. For example, portions of the stroke where anticipated impacts occur (end of stroke where the firing member may ram the end of the staple cartridge, initial contact between the firing member and the sled during the beginning of the stroke, and/or engagement between the jaw camming surfaces which control a tissue gap between the jaws) can all trigger PID control parameter adjustments. For example, a load within the motor system may be detected as the firing member contacts the sled during the beginning of the stroke and, depending on the magnitude of the detected load, the PID controller parameters can be set according to the magnitude of the detected load. In at least one instance, maximum acceptable inertial impacts are set, or predetermined, and, if exceeded, PID controller parameters are adjusted and/or safety motor control algorithms are initiated, for example.

In at least one instance, overshoot is monitored throughout a stroke and PID controller parameters are adjusted according to the overshoot during the stroke so as to reduce the possibility of the firing member from traveling too far and/or not far enough. For example, PID controller parameters are adjusted so the firing member of the motor system does not crash into the end of the staple cartridge and/or end effector. In at least one instance, PID controller parameters are adjusted so the firing member of the motor system does not stop prematurely before achieving its expected full firing stroke distance, for example. Such an arrangement can reduce unnecessary load on the motor system and/or an unfinished staple firing stroke, for example.

In at least one instance, the PID controller parameters are adjusted to place a motor of the motor system into a different efficiency band of the motor curve. Such an arrangement can reduce motor heat generation and performance degradation over time.

In various instances, the PID controller parameters are adjusted, or modified, such as PID controller gain, for example, based on any number of variables. In at least one instance, one or more PID controller parameters are adjusted based on the activation of a no-cartridge lockout. In at least one instance, the one or more PID controller parameters are adjusted based on an accuracy of the motor. For example, motor performance may vary over time. A rotary position sensor, such as a cross over gear encoder, for example, may be used to measure the accuracy of the motor. Depending on the measured accuracy, the gain, for example, of the PID controller can be modified according to the measured accuracy and, in at least one instance, modified to compensate for an increasing decline in accuracy, for example. In at least one instance, the one or more PID controller parameters are modified based on the position of a cutting edge. In at least one instance, the one or more PID controller parameters are modified based on the set values of the PID parameters themselves. For example, if a PID controller parameter is automatically adjusted beyond a threshold, for example, a new set of values may be selected for the PID controller parameters. In at least one instance, the one or more PID controller parameters are modified based on where the end of the staple firing stroke is. In at least one instance, the end of the staple firing stroke is predetermined. In at least one instance, the end of the staple firing stroke changes per use. For example, a user may not actuate a firing member through a full staple firing stroke. The actual end of the firing stroke can be utilized to adjust the gain of the PID controller.

In at least one instance, the one or more PID controller parameters are adjusted based on one or more staple cartridge characteristics such as, for example, the type of cartridge installed. In at least one instance, a sensor is used to determine the color of the cartridge color and one or more PID controller parameters are adjusted to values corresponding to the detected cartridge color. For example a cartridge of a first color may require more force to fire its staples than a cartridge of a second color. The one or more PID controller parameters can be adjusted to compensate for the increased force requirement, for example.

In at least one instance, the one or more PID controller parameters are adjusted based on motor impedance, the variation of Kt (motor torque constant)/Ke(back EMF constant) from a nominal Kt/Ke of the motor due to self-heating, and/or demagnetization of the motor due to prolonged use in heated conditions, for example.

In at least one instance, the one or more PID controller parameters are adjusted based on detected stress within the system. In at least one instance, traces are employed on a printed circuit board, or printed circuit board assembly, of a surgical instrument system to infer bending stresses within the system. For instance, the printed circuit board may be positioned within a surgical instrument handle. The PID controller parameters can be adjusted to compensate for the detected bending stresses, for example.

In at least one instance, heat buildup within the system can be detected and one or more PID controller parameters can be adjusted accordingly. For instance, output motor torque may be implicated by heat build up and, upon detecting a magnitude and/or threshold rate of heat build up that would, in turn, cause a certain threshold torque loss to be experienced, one or more PID controller parameters can be adjusted to reduce heat build up and/or compensate for loss in torque, for example.

In at least one instance, PID controller parameters are adjusted based on where a firing member is within its firing stroke. For example, a motor control circuit can adjust the PID controller parameters automatically when the firing member has been deployed through two thirds of the full staple firing stroke. In at least one instance, the force increases within the last third of the staple firing stroke and, thus, the PID controller parameters can be set to compensate for the expected increase in required firing force, for example. In at least one instance, one or more PID controller parameters are adjusted based on where, longitudinally, tissue is clamped between the jaws. Tissue clamped between the jaws near the distal end may require more force to cut and staple than tissue clamped between the jaws near the proximal end, for example. The one or more PID controller parameters can be adjusted accordingly. In various instances, system load, distal node system efficiency, and/or torsional drive shaft stiffness can be utilized to adjust the PID controller parameters. In at least one instance, one or more strain gauges are utilized to detect stress within the system.

In at least one instance, one or more PID controller parameters are adjusted based on the number of firings performed by a motor system, for example. For instance, an older motor may generate more heat during firings and, thus, the PID controller parameters can be adjusted so as to account for the increased heat risk.

In various instances, new values for PID controller parameters can be estimated by neural networks so as to anticipate the optimal value for the PID controller parameters for future firings, for example. In at least one instance, schedules are used by the motor control circuit to determine when to change the PID controller parameters. For example, after a predetermined amount of firings, the PID controller parameters can be adjusted automatically based on reaching the predetermined amount of firings. In at least one instance, previous uses of similar motors are logged and analyzed to determine PID controller parameters for a local motor system.

Figure 40:
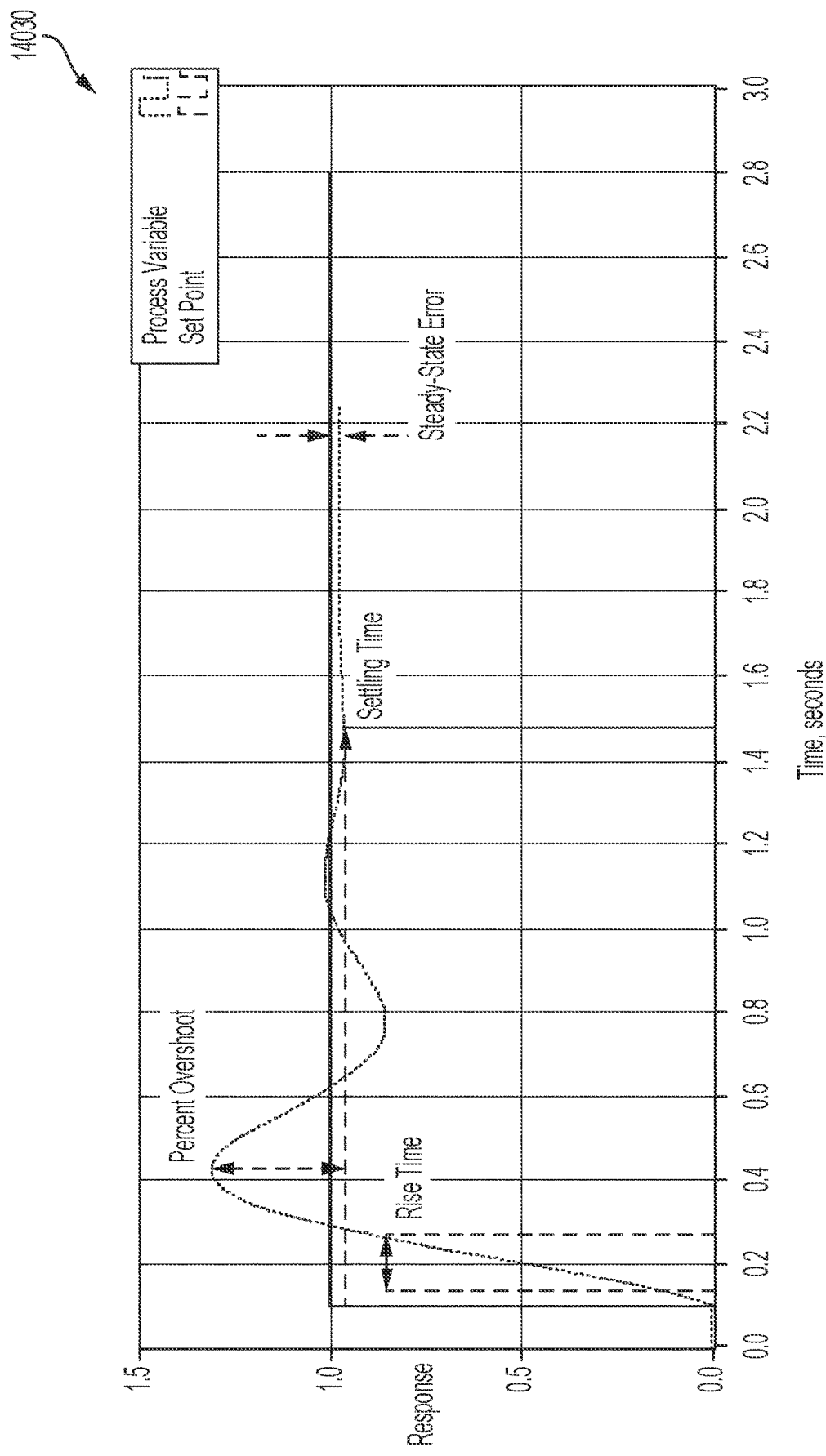
FIG. 40 is a graph depicting various types of signal variables affected by PID controller parameters adjustments.

In various instances, PID controller parameters are tuned to adapt during use of a motor system to increase motor efficiency and/or improve firing stroke outcomes, for example. Referring to FIG. 40, a graph 14030 is shown to describe various setpoint implications of a PID controller, for example. As can be seen in the graph rise time, percent overshoot, settling time, steady-state error can all be optimized, or improved, by adjusting the PID tuning parameters of a PID controller configured to control a motor of surgical instrument motor system. Adjustments can be made based on any combination of the methods and systems disclosed herein. For example, in the context of firing member displacement, automatically tuning the PID controller parameters to reduce percent overshoot (of displacement, for example) can reduce the likelihood of ramming a firing member into the end of a staple cartridge.

Figure 41:
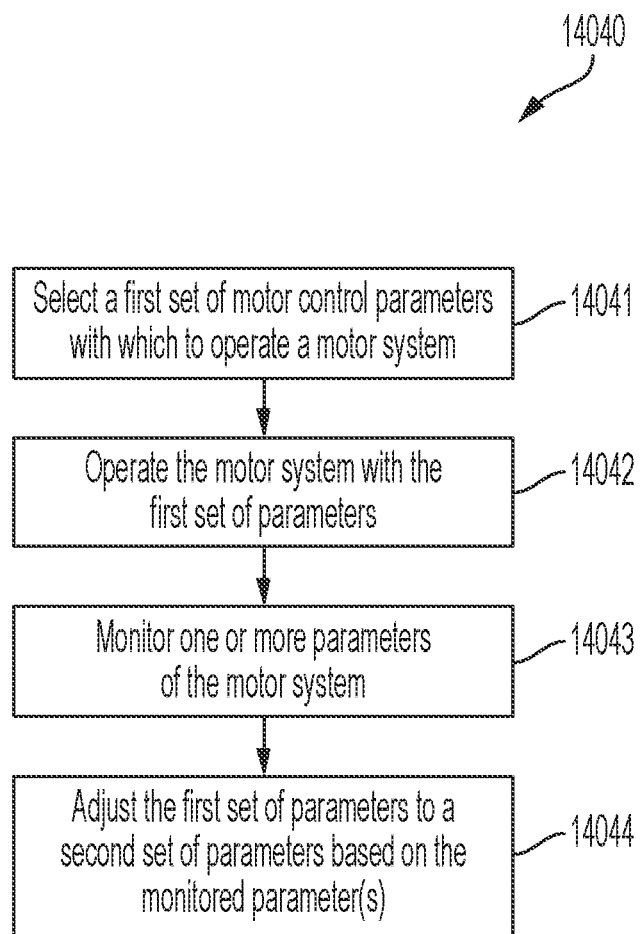
FIG. 41 is a logic flow chart depicting a process executable by a control circuit configured to adjust motor control parameters based on monitored parameters of a motor system.

FIG. 41 is a logic flow chart depicting a process 14040 executable by a control circuit, such as the control circuit 1932 illustrated in FIG. 13 and/or the control circuit illustrated in FIG. 14, for example, herein utilizing close loop control. In at least one instance, feedback is generated from one or more system sensors and an input signal is adjusted to optimize motor control. First, a first set of motor control parameters are selected 14041. In at least one instance, the motor control parameters include PID controller parameters. In at least one instance, the motor control parameters include PWM controller parameters. In at least one instance, the motor control parameters include a range of duty cycles. In at least one instance, the motor control parameters include any combination of proportional, integral, and derivative tuning parameters of the motor controller. The motor control parameters may include any suitable combination of control parameters disclosed herein. During operation 14042 of the motor system, one or more parameters of the motor system are monitored 14043. The one or more monitored parameters may include any suitable parameters such as, for example, position of the firing member, actual measured speed of the firing member, actual measured speed of the motor, and/or type of cartridge installed within the end effector. The monitored parameter may include any combination of parameters disclosed herein. The motor controller parameters are adjusted 14044 to a new set of motor controller parameters based on the monitored parameter(s). For example, a tighter or greater range of duty cycles is selected and/or PID tuning parameter values are adjusted. Any suitable adjustment can be made such as those disclosed herein.

Referring still to FIG. 41, the motor control circuit is configured to deploy a firing member through a staple firing stroke. In at least one instance, the staple firing stroke includes an active stroke portion and an inactive stroke portion, where no adjustments are made to the motor controller parameters during the inactive stroke portion and adjustments are able to be made during the active stroke portion. In at least one instance, the magnitude of the adjustment made to the motor controller parameters is based on a magnitude of the monitored parameter(s). In at least one instance, the magnitude of the adjustment made to the motor controller parameters is based on a rate at which the monitored parameter(s) changes during a portion of the staple firing stroke. In at least one instance, the new set of motor controller parameters includes a first magnitude upon detecting that the firing member, or motor, is decelerating. In such an instance, the new set of motor controller parameters includes a second magnitude which is different than the first magnitude upon detecting that the firing member, or motor, is accelerating.

In various instances, a motor control circuit is configured to activate and/or deactivate one or more motor control circuits and/or algorithms such as those disclosed herein, for example. In at least one instance, the motor control circuit is configured to deactivate motor control adjustments during any suitable portion of a drive stroke of a motor system. For instance, motor system capacity interrogation and corresponding adjustments may be prohibited from occurring during one or more portions of the stroke of a firing member and only able to occur during one or more other portions of the stroke of the firing member. In at least one instance, motor control adjustments may only occur while the firing member is deploying staples within a staple deployment zone of the stroke. In at least one instance, only certain motor control adjustments corresponding to clamping tissue can occur during the clamping of tissue while other certain motor control adjustments corresponding to firing staples and cutting tissue can occur during the staple firing stroke. In at least one instance, the position of the firing member triggers active and/or inactive stages of motor control algorithms and circuits, such as those disclosed herein. For instance, once the firing member reaches a first position, which may be detectable in any suitable manner such as for example, with a position sensor, a first set of motor control algorithms can be activated. Similarly, when the firing member reaches a second position, a second set of motor control algorithms can be activated. Finally, when the firing member reaches a third position, real time motor control adjustments can be prohibited from being made. In at least one instance, portions of a stroke can permit PWM speed control adjustments while other portions of a stroke can prohibit PWM speed control adjustments.

In at least one instance, a motor control circuit is employs PWM speed control adjustments during the clamping of tissue and the articulation of an end effector while prohibiting PWM speed control adjustments during retraction of a firing member, unclamping of tissue, and/or de-articulating an end effector to a neutral position, for example. Various motor control circuits and/or algorithms disclosed herein which are configured to modify the speed of a motor of a motor system during a drive stroke may be referred to as active speed control. In various instances, active speed control is disabled for one or more reasons. In at least one instance, active speed control can be disabled due to an unforeseen event such as, for example, a detected spike in motor current. In at least one instance, the disabling of active speed control can be overridden and re-activated. In at least one instance, active speed control can be manually disabled and/or enabled by a user, for example. In at least one instance, disabling active speed control is configured to directly link a power source to the motor thereby removing any smart control of the motor. In at least one instance, PWM speed control can be deactivated and, in such an instance, the duty cycle of the motor is set to a fixed value such as, for example, 100% and no PWM motor controller adjustments are made. In at least one instance, motor control profiles are reset from stroke to stroke, patient to patient, and/or cartridge to cartridge. In at least one instance, motor control profiles are not reset.

In at least one instance, motor control circuits and algorithms disclosed herein are configured to maintain a constant speed of the firing member rather than constantly change the speed of the firing member as the firing member traverse through tissue, for example.

In various instances, a staple cartridge and/or a staple firing stroke is defined into multiple segments where certain motor control adjustments are confined to a predetermined adjustment range, for example. Such a control circuit can also be used during a closure stroke of a drive shaft, for example. Each segment corresponds to certain motor controller adjustments. For example, during a first third of a staple firing stroke, a control circuit may only be able to make a first range of adjustments to one or more motor controller parameters such as, for example, PID tuning parameters. During a second third of the staple firing stroke, the control circuit may only be able to make a second range of adjustments to the one or more motor controller parameters. Finally, during the third third of the staple firing stroke, the control circuit may only be able to make a third range of adjustments to the one or more motor controller parameters.

In at least one instance, the range of adjustments which may be made during the first third of the staple firing stroke may include a greater range as compared to the adjustment ranges of the second third and/or the third third. This can reduce the possibility of large motor control adjustments from being made during the final stages of the staple firing stroke where a user may not want a firing member to be increasing its speed toward the end of the staple firing stroke risking crashing the firing member into the end of the staple cartridge, for example, which can cause the firing member to get stuck or jam. In at least one instance, no limits are placed on motor controller adjustments during the first third of the staple firing stroke. In at least one instance, no motor controller adjustments can be made during the final third of the staple firing stroke.

The segmented sections of the staple firing stroke, for example, can be separated into any desired fraction. For example, the staple firing stroke may be segmented into fourths, fifths, hundredths, for example. In at least one instance, the staple firing stroke is split into two regions. In various instances, the segments vary in length. In at least one instance, the segments are broken into a beginning segment, a plurality of intermediate segments, and an ending segment.

In various instances, dividing the staple firing stroke into segments where motor control adjustments are limited, confined, or controlled specifically within each segment can control overshoot error during motor operation. Load, or force to fire, for example, can be monitored during each segment and can be used to set motor controller parameters such as, for example, PID tuning values specifically for each segment.

Figure 42:
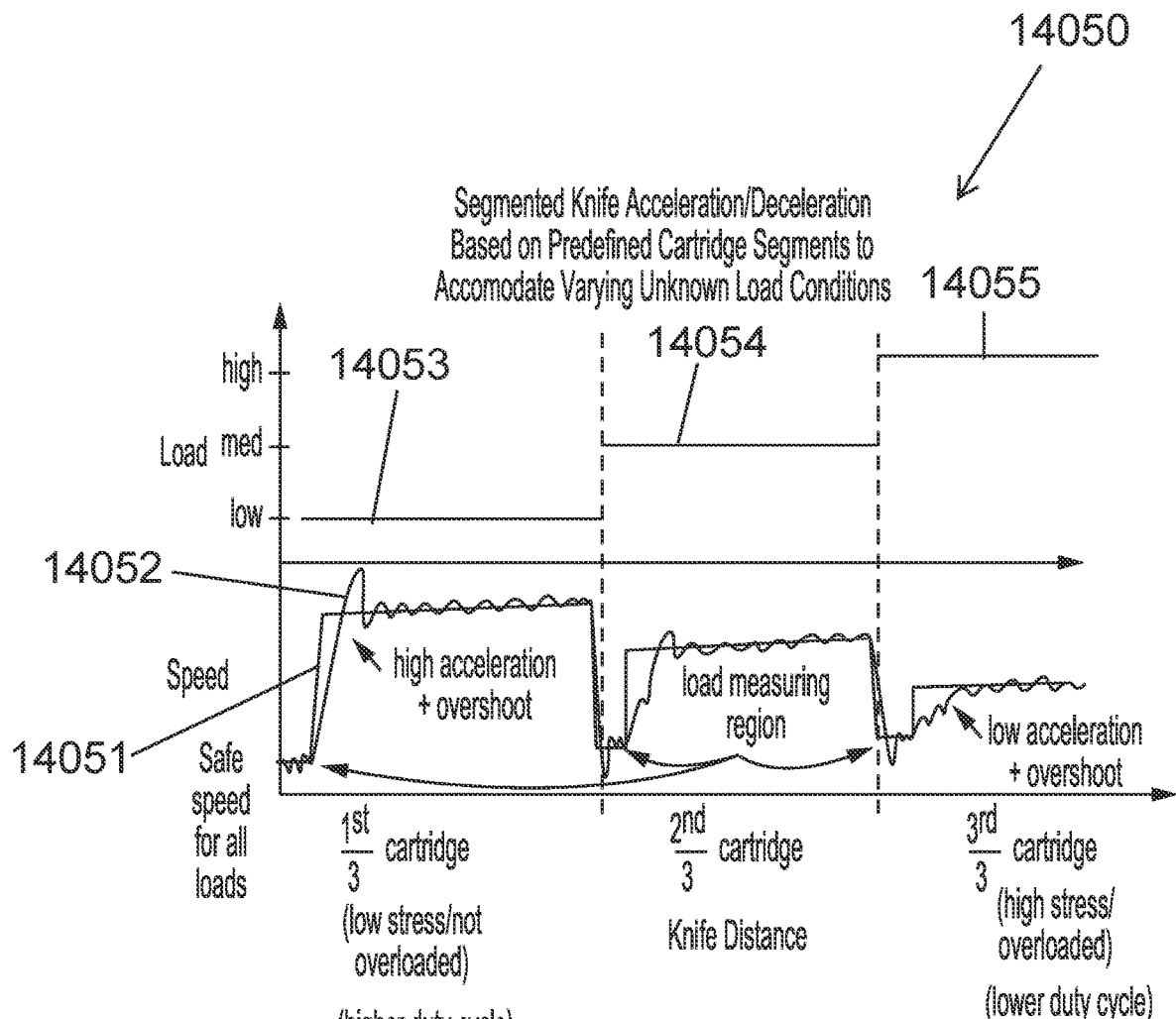
FIG. 42 Is a graph depicting a firing stroke of a motor system including a motor, a drive train, and a motor control circuit, wherein the motor control circuit segments the firing stroke into multiple portions and adjusts one or more motor control parameters of the motor according to each segment.

FIG. 42 is a graph 14050 illustrating a staple firing stroke of a motor system. A control circuit divides the staple firing stroke, or the cartridge, into segments: a first third, a second third, and a third third. The control circuit increases the target speed 14051 of the motor to a safe speed to initiate firing. The control circuit then increases the target speed 14051 of the motor by increasing the duty cycle to a relatively high duty cycle during the first third of the cartridge. As can be seen in the graph 14050, overshoot error of the actual speed 14052 is increased during rapid acceleration of the firing member. The actual speed 14052 of the firing member steadies toward the end of the first third of the cartridge. Then, the target speed 14051 is brought down to another safe target speed 14051. As can also be seen in the graph 14050, the load 14053 during the first third of the cartridge is relatively low as compared to the other segments of the cartridge. As the load increases 14054 during the second third of the staple cartridge, the control circuit sets the target speed 14051 and the actual speed 14052 of the firing member rises at a rate which lower than the rate of speed increase during the first third of the cartridge. This also results in less overshoot error. Finally, with yet another increase in load 14055 during the third third of the cartridge, the target speed 14051 is set and the firing member accelerates slowly to reduce overshoot within the third third of the cartridge. As the load increased throughout the firing stroke, the duty cycle of the motor decreased for each segment to reduce overshoot. High overshoot may cause damage to tissue or the firing system itself. Reducing overshoot during higher load conditions can reduce the possibility of damage to the tissue and/or the firing system. In at least one instance, the loads 14053, 14054, and 14055 are measured while the motor runs at safe speeds prior to increasing the target speed 14052 of the firing member for each segment of the cartridge. In such instances, the speed of the firing member is adjusted according to the magnitude of the measured load where higher loads result in lower set speeds and lower loads result in increased set speeds. In at least one instance, the speed can be increased substantially during low load conditions as there can be reduced risk to the tissue and/or firing system at high speeds with low detected loads. An increased overshoot error during higher load conditions can result in an additional unintended speed increase from a target speed where no tissue or system damage was expected at the target speed but would occur if the increased speed was achieved when overshooting the target speed.

In various instances, PID controller parameters are adjusted automatically to reduce overshoot in higher load conditions. In lower load conditions, the PID controller parameters can be automatically adjusted to optimize speed where overshoot is not an issue. In at least one instance, a threshold of the proportional limit value of a PID controller is lowered in higher load conditions to reduce overshoot. In at least one instance, a threshold of the integral value and a threshold of the derivative value of the PID controller are lowered to reduce overshoot. In various instances, the rate at which the speed of the firing member changes is monitored to determine motor control adjustments such as, for example, PID tuning value adjustments, for the rest of the segment.

In at least one instance, overshoot and/or irregular motor response may be acceptable and/or anticipated during certain portions of a firing stroke. During such portions of the firing stroke, utilizing the location of the firing member to determine when the firing member is in such portions of the firing stroke, the motor control circuit can specifically tune the PID controller values accordingly. In at least one instance, a predicted amount of overshoot is acceptable during a certain portion of the firing stroke. As a result, the PID controller values are adjusted accordingly. In at least one instance, the PID controller values are not adjusted at all during such portion of the firing stroke. In various instances, firing strokes include a predicted force to fire spike location where the force to fire increases at the spike location every time the firing member passes the spike location. Such a location may include where an i-beam contacts and traverses a metal irregularity in a cartridge channel which is the result of the manufacturing process of the cartridge channel. In such instances, a motor control circuit is configured to not adjust PID controller values as the firing member passes the spike location. The location of the firing member can be used to determine when the firing member is going to pass the spike location to prevent the motor control circuit from adjusting the motor controller parameters as the firing member passes this spike location/as a result of the spike in force to fire. In at least one instance, the motor control circuit adjusts the PID controller values at the spike location; however, the magnitude of the adjustment is lower than if the same spike in force was detected during other portions of the staple firing stroke.

Figure 43:
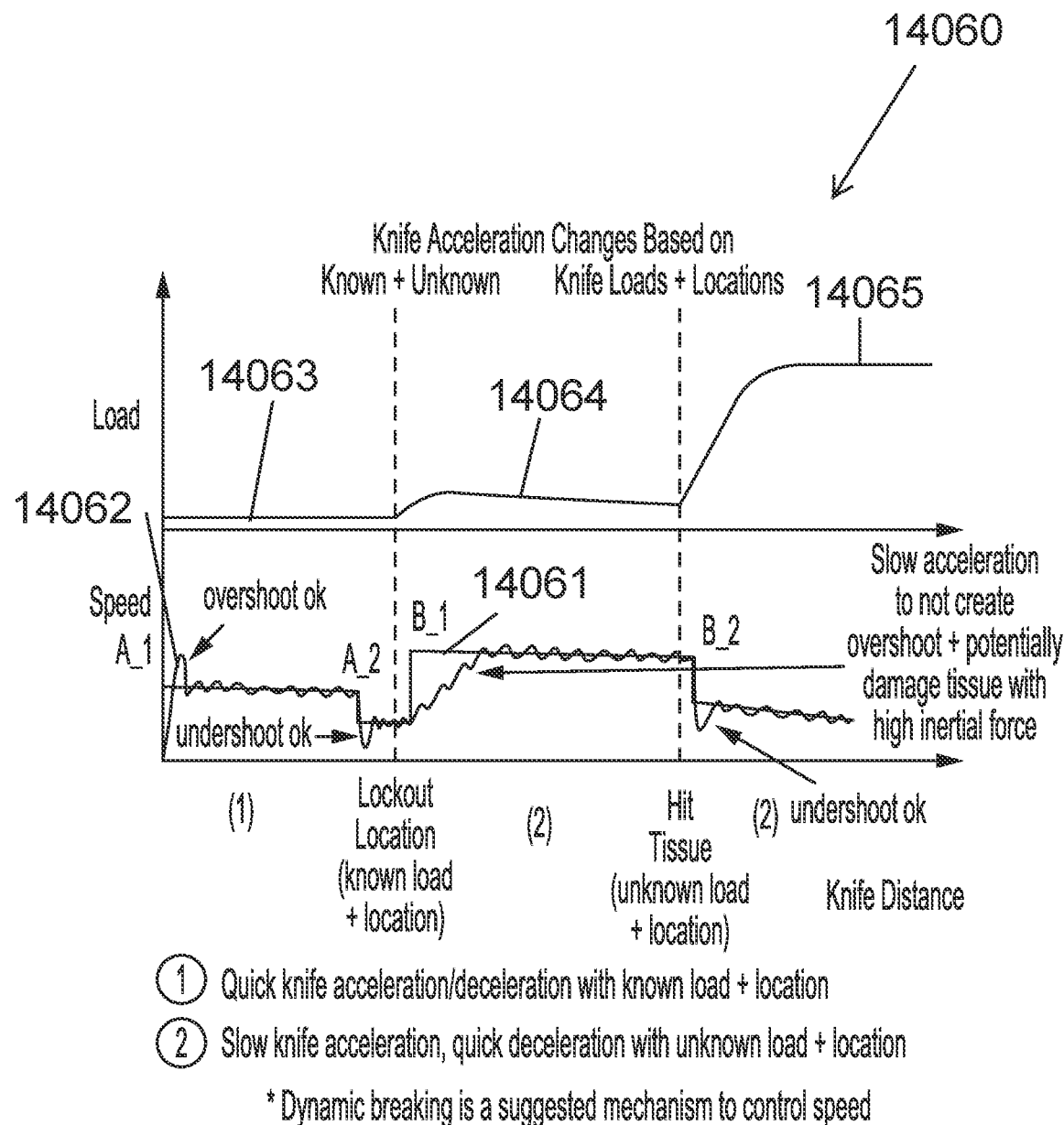
FIG. 43 is a graph depicting a firing stroke of a motor system including a motor, a drive train, and a motor control circuit, wherein the motor control circuit segments the firing stroke into multiple portions and adjusts one or more motor control parameters of the motor according to expected loads and/or monitored location of firing member within the firing stroke.

In various instances, the rate of speed increase or decrease (acceleration/deceleration) by a motor control circuit is adjusted based on a level of overshoot concern and/or undershoot concern as it relates to predictable loads at certain locations, for example. FIG. 43 is a graph 14060 illustrating a firing stroke of a motor system. Target, or set, speed 14061, actual measured speed 14062, and firing loads 14063, 14064, and 14065 are illustrated. During stage (1), the speed of the motor is increased at the beginning A_1 of the firing stroke. During stage (1), overshoot concern is low and, thus, the motor control circuit sets the motor control parameters accordingly (to permit overshoot, for example). The overshoot concern is low because, at this stage of the firing stroke, no tissue is being cut or stapled. Rather, the firing member moves from an unfired position A_1 to a lockout location where the firing member is either locked out from continuing or defeats the lockout. During this stage, the overshoot concern is low. Prior to reaching the lockout location, the speed 14061 is decreased. During this decrease, undershoot is not a concern and, thus, the motor control parameters are set/can be adjusted accordingly. The speed 14061 may be decreased just before the firing member reaches the lockout location to decrease the effective speed before the firing member either locks out or defeats the lockout. The increased speed prior to the decrease in speed at A_2 increases the operating efficiency of the motor prior to the firing member reaching the lockout location. The load 14063 during stage 1 may be known and/or predicted with acceptable accuracy such that there may be no unpredictable load increases/decreases during this stage. Because the load is predicted within this stage, the motor controller parameters can be set accordingly.

After the firing member defeats the lockout and moves past the lockout location, stage 2 begins. At B_1, the speed 14061 is increased because the load 14064 is unknown. The load 14064 is unknown because at any point during stage 2, the firing member (or cutting member) can hit tissue. Also, because the load 14064 is unknown, overshoot is of a higher concern than of stage 1. Overshoot when hitting tissue during this stage can cause tissue damage by applying a higher than predicted inertial force. This higher than predicted inertial force is because of the initial spike of input speed experienced (overshoot) beyond the set target speed. Because overshoot is of higher concern, the motor control parameters can be set accordingly to decrease the rate at which the speed of the firing member increases. As can be seen on the graph 14060, overshoot of the actual speed 14062 is low because the motor control parameters were set accordingly. At stage 3, load 14065 is unknown and speed 14062 is decreased at B_2 with the concern of undershoot being relatively low. Undershoot may be okay in several scenarios because slowing of a firing member below a target speed from a higher speed may not pose a risk for damaging tissue.

In various instances, dynamic breaking can be employed by a motor control circuit to reduce overshoot. In at least one instance, actual speed is monitored and compared to the target speed and, as the actual speed approaches the target speed, the motor can be slowed or braked dynamically to reduce and/or eliminate overshoot and/or undershoot. In at least one instance, dynamic breaking is used in combination with acceleration limiting to control overshoot. In at least one instance, inertia of a motor system is monitored during a firing stroke and is used to determine acceleration limit adjustments.

In various instances, an importance magnitude is utilized in a motor control circuit. The importance magnitude is a value assigned to predetermined sections of a firing stroke, for example. The value indicates the importance, or lack thereof, of reducing overshoot and/or undershoot, for example during the identified firing stroke section. With reference to FIG. 43, an importance magnitude at position B_1 can be assigned a "1" being the most important location to reduce overshoot, an importance magnitude at positions A_1, A_2, and B_2 can be assigned a "2" indicating a lower importance of reducing overshoot and/or undershoot, for example.

In various instances, the rate of change of speed can be monitored (by way of PWM duty cycle, PWM frequency, PWM amplitude (voltage)) relative to a target threshold to adjust motor control parameters to reduce and/or eliminate overshoot, for example. In at least one instance, a motor control circuit is configured to monitor the magnitude of PID deviation from an instantaneous target over time at a certain frequency and monitor the rate of change of PID deviation during the period of time to determine if the motor system is falling behind further with each subsequent target or if the motor system is accelerating closer to the target with each subsequent target. This determination can be used in conjunction with how far away from the target the actual value is at each target to dampen the acceleration/deceleration to prevent overshoot/undershoot. In at least one instance, the rate of change of speed is monitored at the initial part of each stage, cycle, or firing stroke section, and/or at the end part of each stage, cycle, or firing stroke section, for example.

Figure 44:
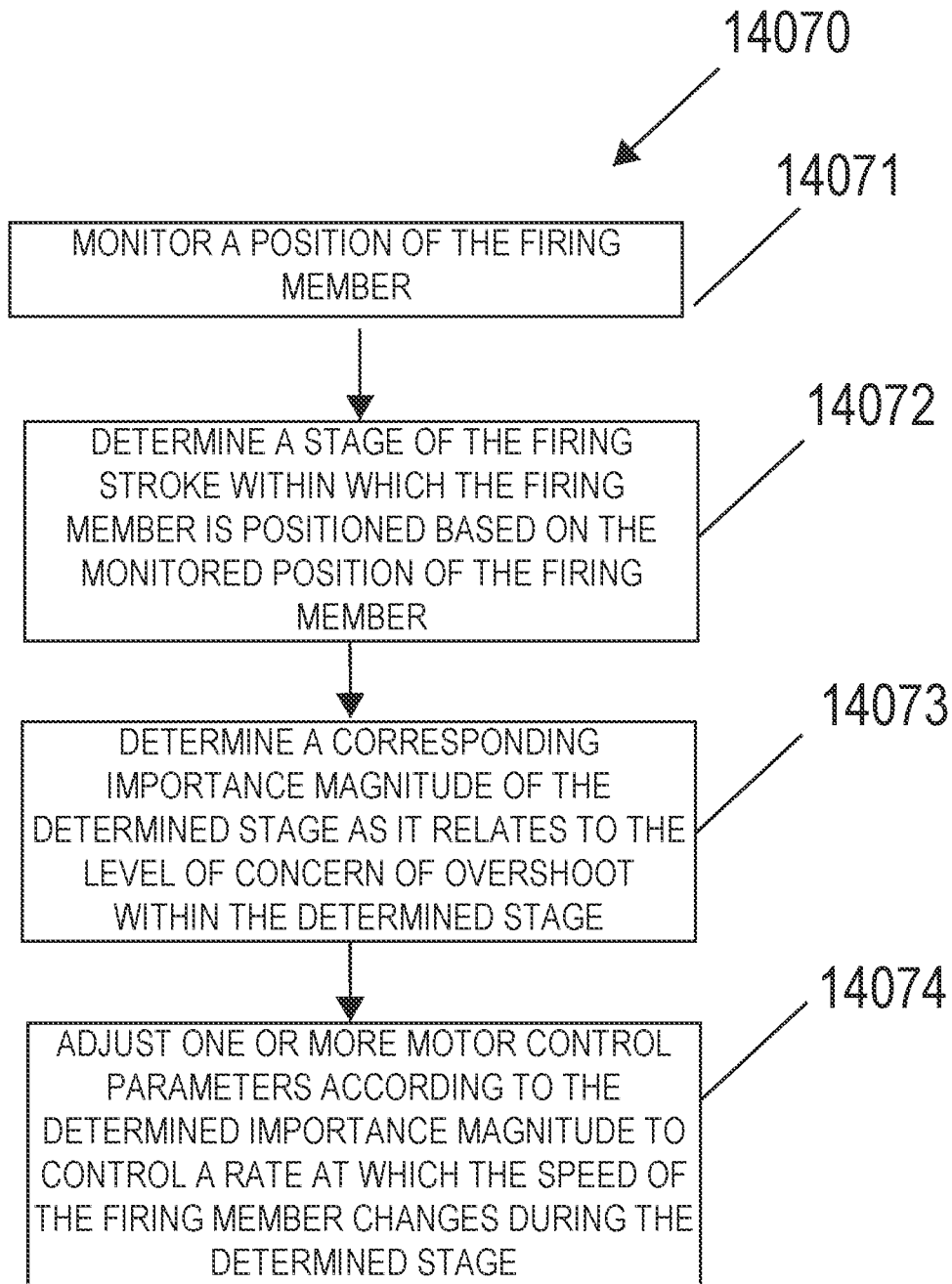
FIG. 44 is a logic flow chart depicting a process executable by a control circuit configured to control a motor of a motor system.

FIG. 44 is a logic flow chart depicting a process 14070 executable by a control circuit, such as the control circuit 1932 illustrated in FIG. 13 and/or the control circuit illustrated in FIG. 14, for example, configured to control a motor of a motor system. The motor control circuit is configured to monitor 14071 a position of the firing member. The position of the firing member may be monitored in any suitable manner such as, for example, by a position sensor, a displacement sensor, and/or an encoder configured to measure motor rotation. The motor control circuit is further configured to determine 14072 a stage of the firing stroke within which the firing member is position based on the monitored position of the firing member. For example, the motor control circuit, based on the monitored position of the firing member, can determine that the firing member is within a first third of the cartridge, or first segment of three segments of the firing stroke, for example. The motor control circuit is further configured to determine 14073 a corresponding importance magnitude of the determined stage as it relates to the level of concern of overshoot occurring within the determined stage. In at least one instance, the importance magnitude includes a scale including low importance, medium importance, and high importance. Low importance indicates that the occurrence of overshoot is of little concern. High importance indicates that the occurrence of overshoot is of high concern. High importance may be associated with a stage of the firing stroke where load on the firing member is high. In at least one instance, the importance magnitude is determined based on the position of the firing member. In at least one instance, load on the firing member is monitored and is used to determine the importance magnitude. Higher load on the firing member can be associated with a high level of concern of overshoot, for example. The motor control circuit is further configured to adjust 14074 one or more motor control parameters according to the determined importance magnitude to control a rate at which the speed of the firing member changes during the determined stage. The one or more parameters may include any suitable parameters such as motor controller parameters, PID controller tuning parameters, and/or PWM duty cycle ranges, for example.

In various instances, motor control parameters, circuits, and/or algorithms such as those disclosed herein, are adjusted in an effort to limit loads experienced within an end effector. Such loads can be caused by thick and/or tough tissue, for example. Loads can be experienced by the motor through various stages of the use of a surgical instrument. For example, loads can be experienced by the motor through a firing member as the firing member is advanced through a staple firing stroke, by the motor through a closure member during the clamping of tissue, for example. Load levels can be detected in any suitable manner such as, for example, by monitoring motor current of a motor configured to drive a firing member and/or through a force sensor, such as a strain gauge, for example, positioned on a firing member. In at least one instance, the speed of the motor of a motor system is decreased to decrease load experienced by the firing member.

In at least one instance, a motor control circuit is configured to modulate torque (force) and speed (voltage) of the motor simultaneously in an effort to reduce load experienced by a drive train. In at least one instance, the speed of the motor is reduced to decrease the load experienced within the end effector. In at least one instance, controlled pause, or wait, periods are utilized to decrease the load experienced within the end effector.

Figure 45:
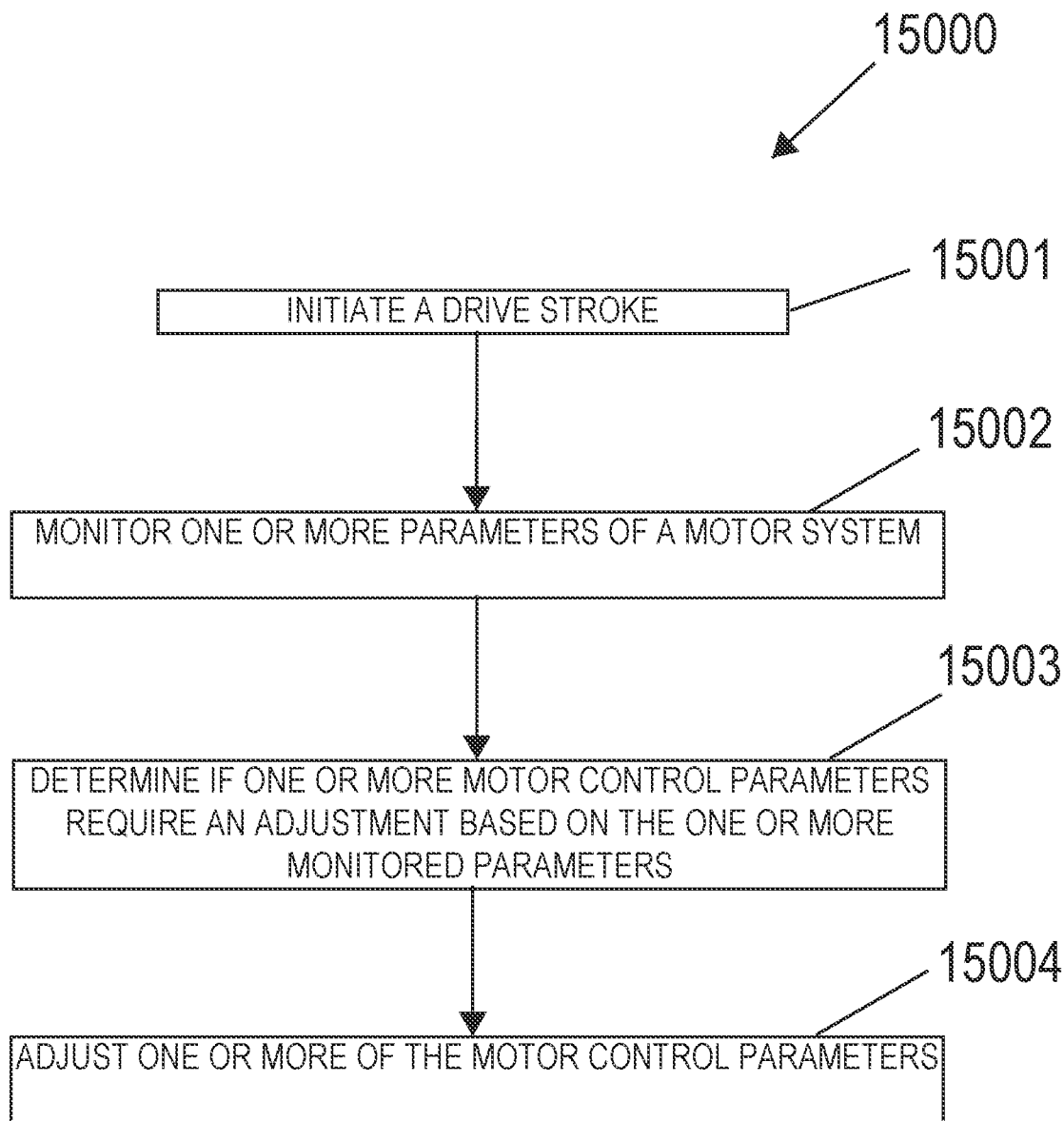
FIG. 45 is a logic flow chart depicting a process executable by a control circuit configured to control a motor system of a surgical instrument system.

FIG. 45 is a logic flow chart depicting a process 15000 executable by a control circuit, such as the control circuit 1932 illustrated in FIG. 13 and/or the control circuit illustrated in FIG. 14, for example, for use with a surgical instrument system such as those disclosed herein. The control circuit is configured to control the motor of a motor system within a surgical instrument system. The control circuit is configured to receive one or more inputs and produce an output signal to the motor corresponding to the one or more inputs. The control circuit is configured to monitor one or more electrical and/or mechanical parameters of the motor system such as, for example, rotational output speed of the motor, linear output speed of a firing member, current draw of the motor, and/or load experienced by the motor system. In at least one instance, the control circuit is configured to convert one or more analog outputs such as motor speed, current draw, firing member speed, etc., to a digital signal. In at least one instance, a digital control signal is configured to be converted to an analog input signal for the motor. In at least one instance, the one or more analog output signals are configured to be converted to digital signals which can be fed back into the control circuit and be utilized as inputs of the control circuit.

The control circuit is configured to initiate 15001 a drive stroke such as, for example, a staple firing stroke. In at least one instance, the drive stroke includes a closure stroke, a retraction stroke, and/or any portion of any stroke within a surgical instrument system. In at least one instance, the control circuit is configured to adjust one or more motor control parameters while the motor is not running, prior to a drive stroke, and/or after a drive stroke, for example. The motor control circuit is further configured to monitor 15002 one or more parameters of the motor system such as those disclosed herein. As discussed above, in at least one instance, the motor control circuit is configured to convert an analog signal of the one or more monitored parameters to a digital signal and feed the digital signal back into the control circuit. The motor control circuit is further configured to determine 15003 if one or more motor control parameters require an adjustment based on the one or more monitored parameters. Any suitable trigger and/or threshold can be employed such as those disclosed herein. In at least one instance, a load threshold is employed and, when the load threshold is exceeded, the control circuit adjusts 15004 one or more motor control parameters.

In an instance where a load threshold is triggered, for example, it can be determined that a section of stiff, or thick, tissue is being encountered by the firing member. In at least one instance, the control circuit adjusts one or more motor control parameters to power through the stiff tissue. In at least one instance, an oscillating signal is delivered to the motor causing the motor to repeatedly impact the tissue for a period of time in an effort to burst through the thick tissue. In at least one instance, a PWM signal is used to provide motor oscillation. In at least one instance, the motor oscillation involves a sequence of quick bursts of energy. In at least one instance, the control circuit is configured to move the firing member in a proximal direction prior to each burst of energy in an effort to increase the moment of inertia while impacting thick tissue. In at least one instance, a combination of pulse width modulation in addition to pulse amplitude modulation are utilized.

The width (time) of each pulse can be adjusted based on the one or more monitored parameters such as, for example, the magnitude of the load experienced by the firing member. Similarly, the amplitude (voltage) of each pulse can be adjusted based on the one or more monitored parameters such as, for example, the magnitude of the load experienced by the firing member. In various instances, the width of each pulse and/or the amplitude of each pulse are varied as the firing member is traversing thick tissue. In at least one instance, the firing member is oscillated in the manner described above for a period of time, paused, and oscillated again. In at least one instance, the duration of the oscillating motor operation can be dependent on the one or more monitored parameters. For example, when the load experienced by the firing member decreases below a predetermined load threshold, for example, normal firing member operation can resume. In at least one instance, a delay is employed by the control circuit so as to ensure the firing member is beyond the section of thick tissue, allowing the oscillating signal to power the firing member a predetermined distance beyond the moment that the load on the firing member falls below the predetermined threshold.

Figure 46:
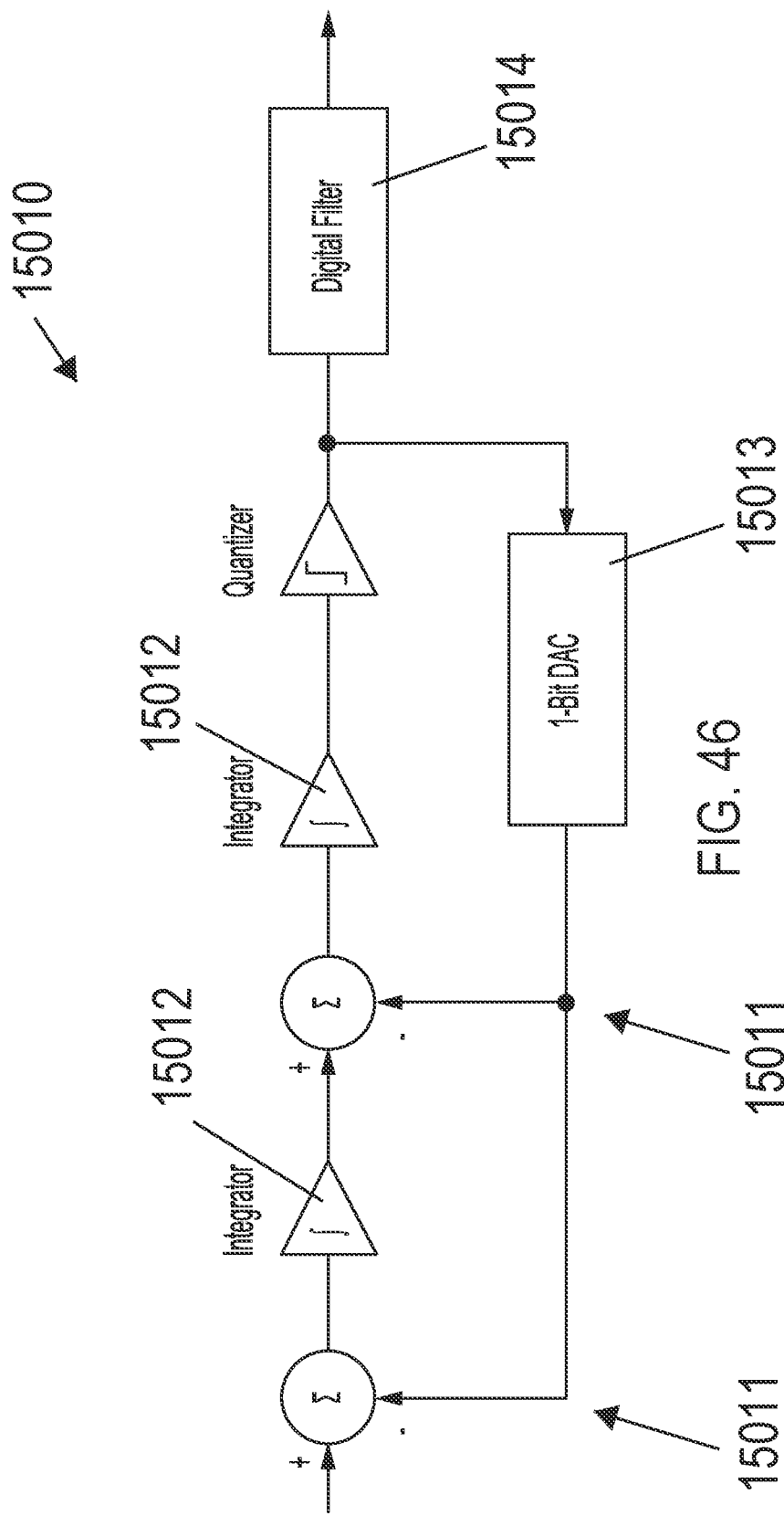
FIG. 46 is a control diagram of a delta-sigma modulator.

In at least one instance, a delta-sigma modulation based bit-stream controller is utilized in the control circuit to drive the motor. Such a controller can utilize an analog output and generate a digital control signal. One example of a delta-sigma modulator 15010 can be seen in FIG. 46. The delta-sigma modulator 15010 is a second-order delta-sigma modulator. As can be seen in FIG. 46, two feedback loops 15011 are utilized in addition to two integrators 15012. A 1-bit DAC 15013 is also used. Finally, a digital filter 15014 is employed to form a higher-resolution digital output.

Figure 47:
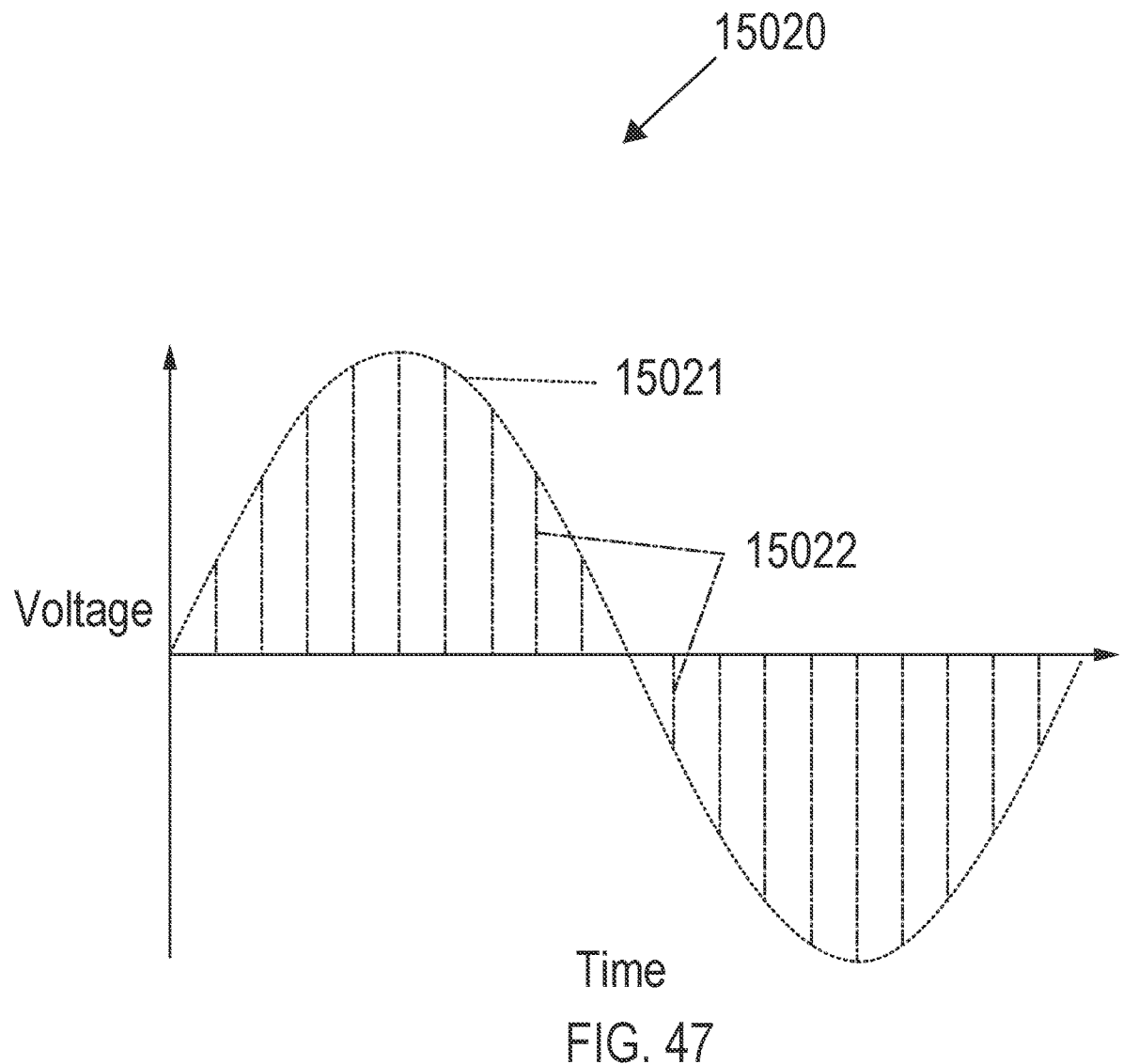
FIG. 47 is a graph of an analog signal and a resulting pulse amplitude modulation signal.

As discussed herein, pulse amplitude modulation can also be used by a control circuit to control the motor. FIG. 47 depicts a graph 15020 depicting a first signal 15021 and a pulse amplitude modulation signal 15022 representing the first signal 15021. Pulse amplitude modulation can supply varying voltage amplitudes for motor control. In at least one instance, a combination of variable output forces can be achieved by moving up and/or down on the torque-power curve of the motor. In at least one instance, duty cycle is also used in conjunction with pulse amplitude modulation to regulate voltage and/or power into the motor to control motor speed.

Figure 48:
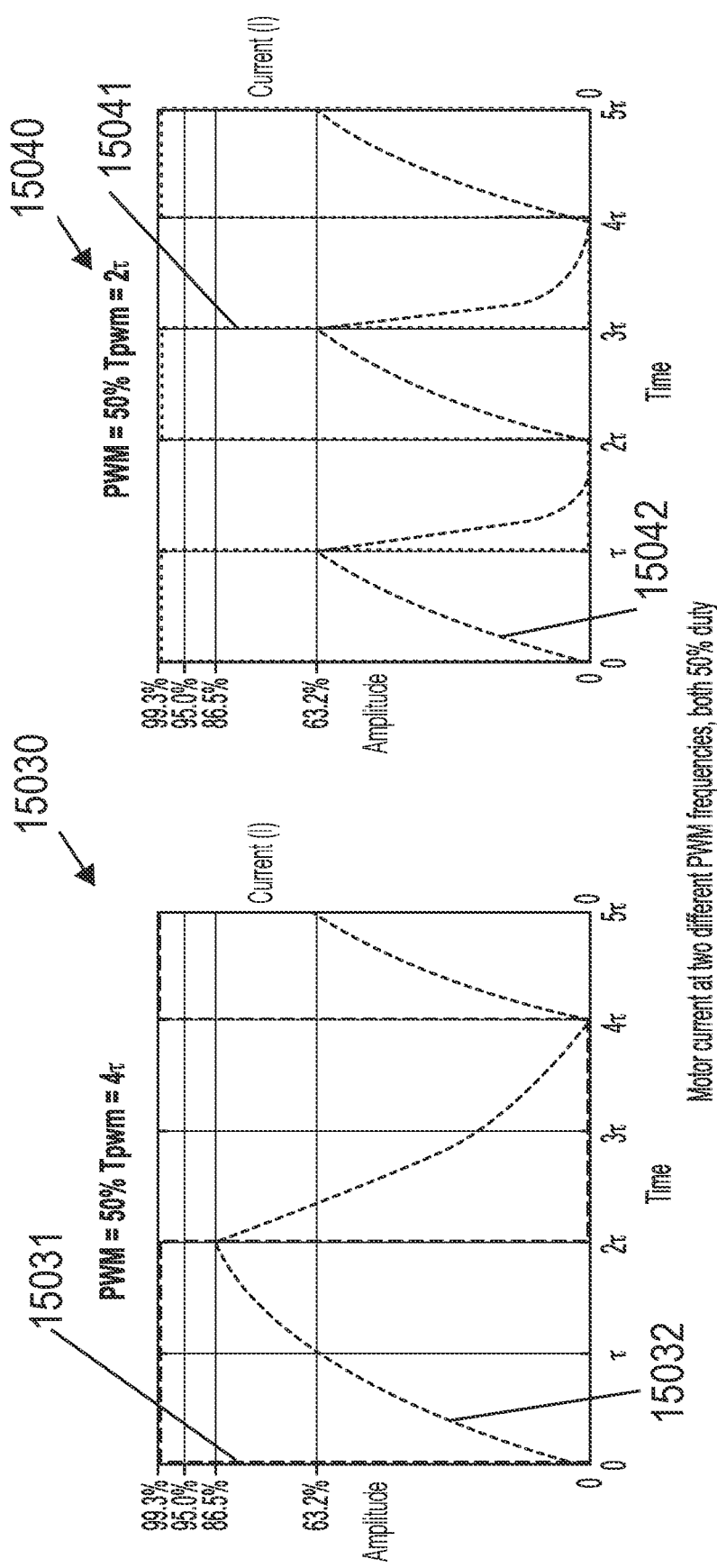
FIG. 48 is a comparison of motor current at two different pulse width modulation frequencies, wherein each signal includes the same duty cycle.

In various instances, pulse width frequency modulation is used to control the speed of a motor in a surgical instrument system. In at least one instance, a control circuit is configured to monitor the current through a motor. In addition to, or in lieu of, varying a duty cycle of a PWM signal, the control circuit can be configured to modulate the frequency of the pulse. The modulation of the frequency of the pulse can be adjusted according to one or more monitored parameters of a drive stroke, for example. In at least one instance, the control circuit is configured to adjust the frequency of the pulse to a first frequency upon detecting a first parameter threshold and a second frequency upon detecting a second parameter threshold. The first frequency is different than the second frequency and the first parameter threshold is different than the second parameter threshold. In at least one instance, a faster frequency may reduce current draw through the motor. FIG. 48 depicts two graphs 15030, 15040 of PWM signals 15031, 15041 at two different frequencies relative to current draw (I) through the motor. As can be seen in FIG. 48, the current draw 15032 is greater than the current draw 15042 for the same 50% duty cycle. In at least one instance, pulse frequency modulation can be beneficial in a brushless DC motor where multiple electromagnets are used in a frequency cascade. Speed of the brushless DC motor can be controlled with little to no impact to motor torque output.

Figure 49:
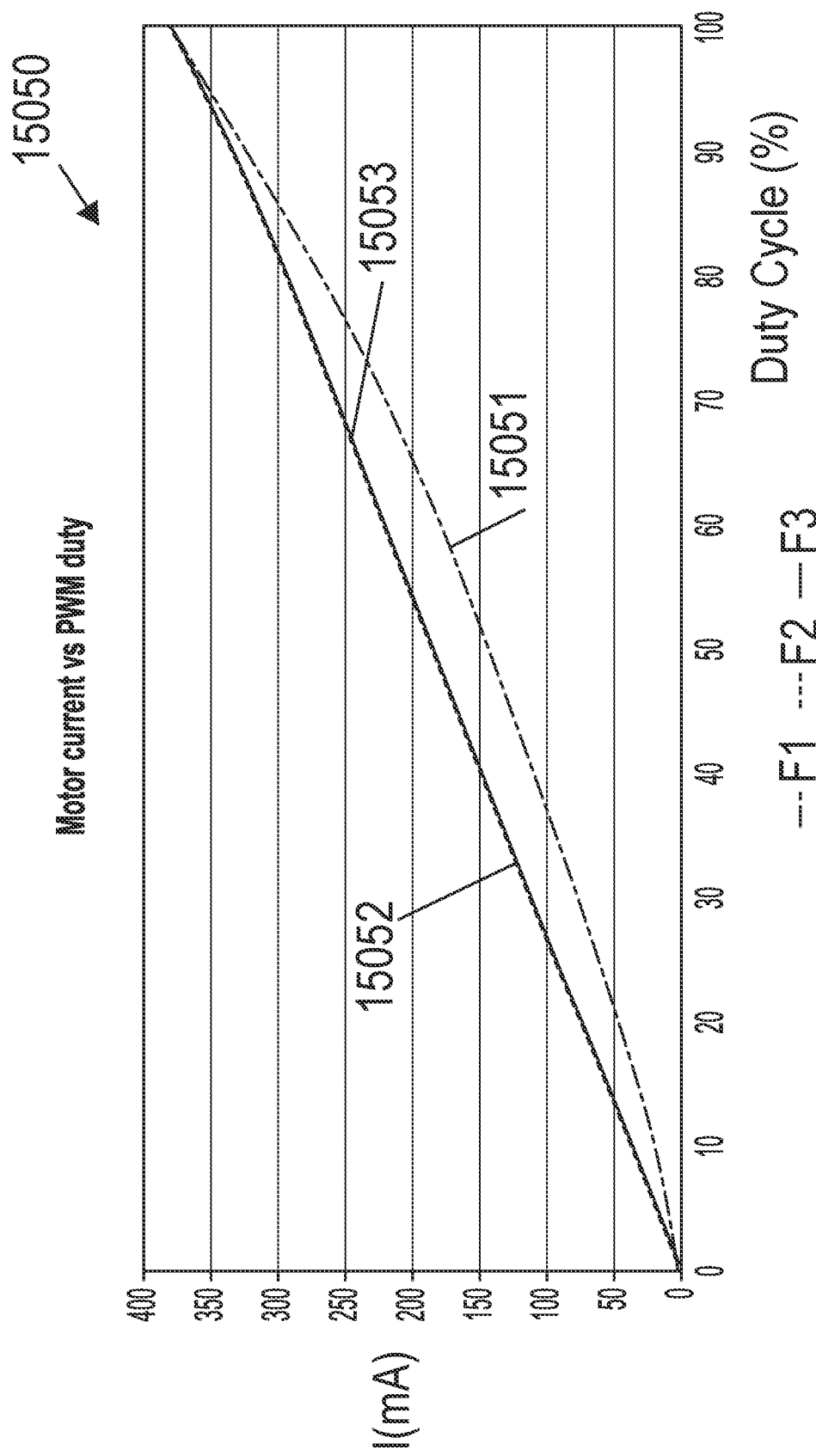
FIG. 49 is a graph illustrating motor current at different duty cycles and pulse width modulation frequencies.

FIG. 49 is a graph 15050 of various signals 15051, 15052, and 15053 depicting duty cycle of the signal relative to current draw through the motor at different frequencies F1 (the frequency of signal 15051), F2 (the frequency of signal 15052), and F3 (the frequency of signal 15053). In at least one instance, F1 is greater than F2, and F2 is greater than F3. In at least one instance, a higher frequency can reduce current draw through a motor.

In various instances, a control circuit configured to control the motor of a motor system is configured to use pulse amplitude modulation and/or pulse width frequency modulation in conjunction with wait, or pause, periods. In at least one instance, the control circuit is configured to monitor current through the motor and adjust, based on the monitored current, a pulse width frequency and/or a pulse amplitude based on the monitored current. In at least one instance, the adjustment occurs after a wait, or pause, period. In at least one instance, the wait, or pause, period is predetermined. In at least one instance, the wait period varies. In at least one instance, the wait period depends on the magnitude of the monitored current. For example, a control circuit can set a wait period to a first time period after a first current is monitored and set a wait period to a second time period which is greater than the first time period after a second current is monitored which is greater than the first current. In at least one instance, such controlled wait, or pause, times can reduce the load experienced by a firing member during a firing stroke upon surpassing a predetermined level of current through the motor. Setting the magnitude of the time period corresponding to the level of current detected through the motor can allow for situational specific wait times where a longer wait period, for example, may not be necessary at a lower current threshold.

Figure 50:
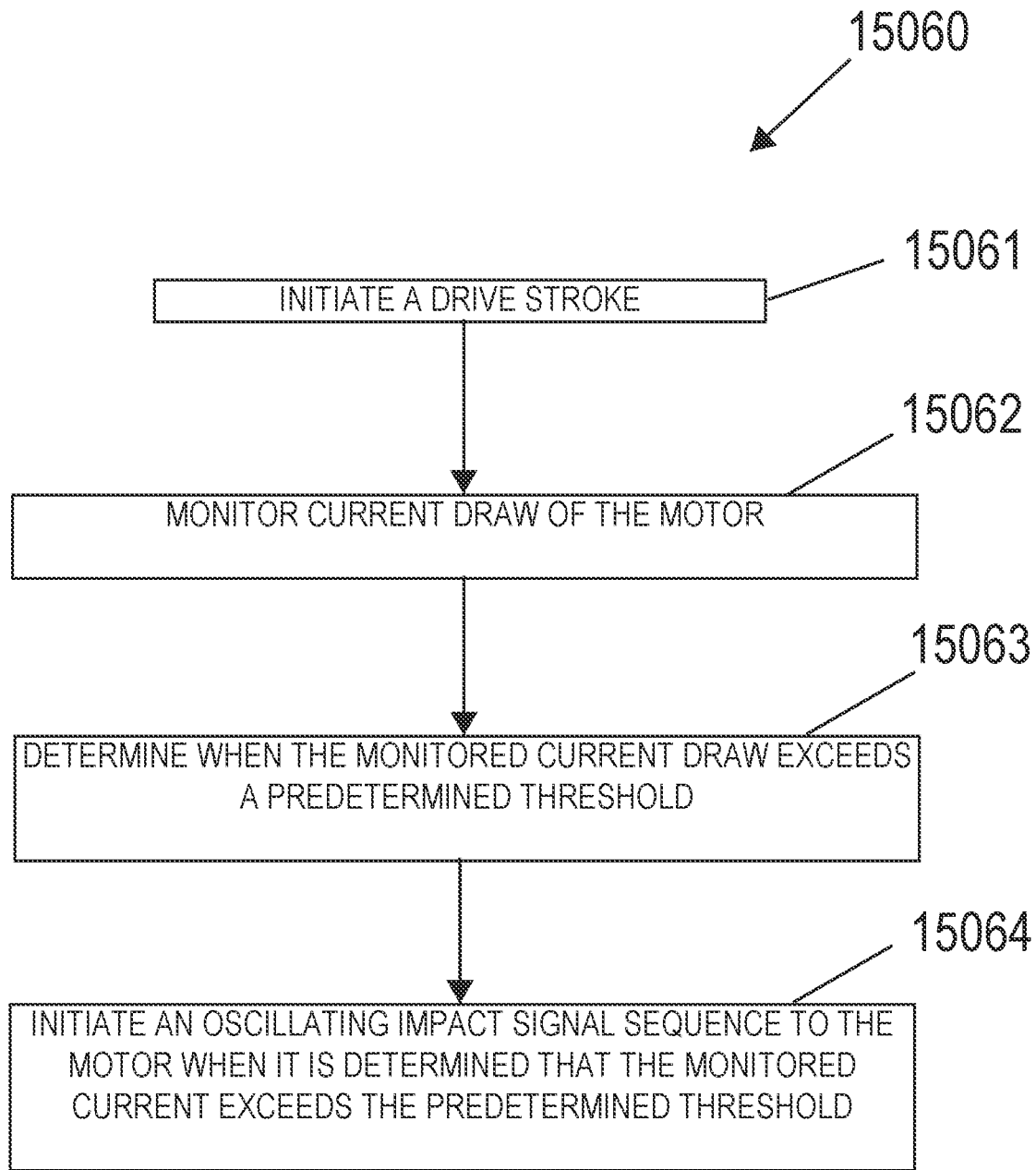
FIG. 50 is a logic flow chart depicting a process executable by a control circuit configured to control a motor system of a surgical instrument system, wherein the control circuit is configured to initiate an oscillating drive signal to a motor of the motor system upon detecting that current through the motor exceeds a predetermined threshold.

FIG. 50 is a logic flow chart depicting a process 15060 executable by a control circuit, such as the control circuit 1932 illustrated in FIG. 13 and/or the control circuit illustrated in FIG. 14, for example, configured to control a motor of a motor system of a surgical instrument system. The control circuit is configured to initiate 15061 a drive stroke of the motor system. Such a drive stroke can include a staple firing stroke of a firing member, for example. During the drive stroke, the control circuit is configured to monitor

15062 current draw of the motor. Any suitable monitoring method can be used such as, for example, utilizing a current transducer. The control circuit is configured to determine 15063 when the monitored current exceeds a predetermined threshold. The predetermined threshold can indicate an over-current situation where thick tissue, for example, has been encountered by the firing member thereby increasing the load on the firing member and, thus, the current draw by the motor. Upon determining that the predetermined threshold has been exceeded, the control circuit is configured to initiate 15064 an oscillating impact signal sequence to the motor.

In at least one instance, the oscillating impact signal sequence includes a digital motor control signal. In at least one instance, a pulse width, a pulse amplitude, and/or a pulse frequency is preselected. In at least one instance, a pulse width, a pulse amplitude, and/or a pulse frequency is selected upon determining that the predetermined current threshold has been exceeded. In at least one instance, the pulse width, the pulse amplitude, and/or the pulse frequency is selected based on one or more monitored parameters of the motor system such as, for example, the magnitude at which the current exceeded the predetermined current threshold, for example. In at least one instance, each pulse delivered to the motor can correspond to a distal impact motion of the firing member. In various instances, a reversing movement, or pulse, can be utilized for each distal pulse movement so as to allow the firing member a certain amount of distance to gain momentum in an effort to pass the thick section of tissue, for example. In at least one instance, the oscillating impact signal sequence further includes a pause period configured to allow for tissue to relax. In at least one instance, a predetermined number of distal pulse movements of the firing member occur prior to the pause period. In at least one instance, several pause periods can be used until the thick tissue is traversed by the firing member.

Various aspects of the subject matter described herein are set out in the following examples.

Example 1—A surgical instrument system comprising a motor system comprising a motor and a drive train coupleable to the motor and configured to actuate a firing member through a staple firing stroke. The surgical instrument system further comprises a control circuit coupled to the motor, wherein, during the staple firing stroke, the control circuit is configured to determine a relative capacity of the motor system during an interrogation, wherein the interrogation comprises setting the motor to run at an interrogation target speed for a period of time, wherein the interrogation target speed is greater than a current speed, measuring an actual response speed of the motor during the period of time, and determining a magnitude of a deviation between the actual response speed and the interrogation target speed during the interrogation. The control circuit is further configured to increase the speed of the motor to a new speed upon determining that the magnitude of deviation is at or below a predetermined threshold of deviation.

Example 2—The surgical instrument system of Example 1, wherein a magnitude of the difference between the current speed and the set interrogation target speed is imperceptible to a user.

Example 3—The surgical instrument system of Examples 1 or 2, wherein the set interrogation target speed is equivalent to the new speed.

Example 4—The surgical instrument system of any one of Examples 1-3, wherein the predetermined threshold of deviation comprises a predetermined percentage of the set interrogation target speed.

Example 5—The surgical instrument system of any one of Examples 1-4, wherein the control circuit is configured to continuously determine the relative capacity of the motor system by initiating additional interrogations.

Example 6—The surgical instrument system of any one of Examples 1-5, wherein a magnitude of speed increase for each subsequent interrogation is the same.

Example 7—The surgical instrument system of any one of Examples 1-6, wherein a magnitude of speed increase for each subsequent interrogation increases logarithmically.

Example 8—The surgical instrument system of any one of Examples 1-7, wherein a magnitude of speed increase for each subsequent interrogation increases non-linearly.

Example 9—The surgical instrument system of any one of Examples 1-8, wherein the period of time for each subsequent interrogation is the same.

Example 10—The surgical instrument system of any one of Examples 1-9, wherein the period of time for each subsequent interrogation is different.

Example 11—The surgical instrument system of any one of Examples 1-10, wherein the motor is controlled by a pulse width modulation circuit, and wherein the control circuit is configured to increase a duty cycle of the pulse width modulation circuit to increase the speed of the motor.

Example 12—A surgical instrument system comprising a drive train comprising a motor and a shaft actuatable by the motor to actuate a function of an end effector. The surgical instrument system further comprises a control circuit coupled to the motor, wherein the control circuit is configured to determine a relative excess capacity of the drive train, compare the relative excess capacity to a predetermined shifting threshold, and increase the speed of the motor based on the relative excess capacity exceeding the predetermined shifting threshold.

Example 13—The surgical instrument system of any one of Example 12 wherein the control circuit is configured to determine the relative excess capacity of the drive train by increasing a target speed of the motor, monitoring an actual speed of the motor, and comparing the increased target speed to the monitored actual speed.

Example 14—The surgical instrument system of Example 13, wherein the increased target speed comprises a magnitude which is below a user-perceptible threshold.

Example 15—The surgical instrument system of Examples 12 or 13, wherein the control circuit is configured to determine the relative excess capacity of the drive train repeatedly during a drive stroke of the shaft.

Example 16—The surgical instrument system of any one of Examples 12-15, wherein the motor is controlled by a pulse width modulation circuit, and wherein the control circuit is configured to increase a duty cycle of the pulse width modulation circuit to increase the speed of the motor.

Example 17—The surgical instrument system of any one of Examples 12-16, wherein determining the relative capacity of the drive train occurs before a staple firing stroke begins but after tissue is clamped.

Example 18—The surgical instrument system of any one of Examples 12-17, wherein the control circuit is configured to determine the relative excess capacity during a staple firing stroke of the shaft.

Example 19—The surgical instrument system of any one of Examples 12-18, wherein the control circuit is configured to determine the relative excess capacity during a closure stroke of the shaft.

Example 20—The surgical instrument system of any one of Examples 12-19, wherein the control circuit is configured to determine the relative excess capacity during an articulation stroke of the shaft.

Example 21—A surgical instrument system comprising a motor system comprising a motor; and a drive train coupleable to the motor and configured to actuate a firing member through a staple firing stroke. The surgical instrument system comprises a control circuit coupled to the motor, wherein, during the staple firing stroke, the control circuit is configured to increase the speed of the motor to a first target speed for a period of time, measure an actual speed of the motor during the period of time, determine if the actual speed achieves a predetermined percentage of the first target speed, and adjust the speed of the motor to a second target speed, wherein a magnitude of the second target speed is based on the determination of whether or not the actual speed achieves the predetermined percentage of the first target speed.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail, and is incorporated herein by reference in its entirety.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in one or more aspects of the present disclosure, a microcontroller may generally comprise a memory and a microprocessor ("processor") operationally coupled to the memory. The processor may control a motor driver circuit generally utilized to control the position and velocity of a motor, for example. In certain instances, the processor can signal the motor driver to stop and/or disable the motor, for example. In certain instances, the microcontroller may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available for the product datasheet.

It should be understood that the term processor as used herein includes any suitable microprocessor, or other basic computing device that incorporates the functions of a computer's central processing unit (CPU) on an integrated circuit or at most a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In at least one instance, the processor may be any single core or multicore processor such as those known under the trade name ARM Cortex by Texas Instruments. Nevertheless, other suitable substitutes for microcontrollers and safety processor may be employed, without limitation.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

Various instruments, tools, hubs, devices and/or systems, in accordance with the present disclosure, may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

One or more motor assemblies, as described herein, employ one or more electric motors. In various forms, the electric motors may be a DC brushed driving motor, for example. In other arrangements, the motor may include a brushless motor, a cordless motor, a synchronous motor, a stepper motor, or any other suitable electric motor. The electric motors may be powered by a power source that in one form may comprise a removable power pack. Batteries may each comprise, for example, a Lithium Ion ("LI") or other suitable battery. The electric motors can include rotatable shafts that operably interface with gear reducer assemblies, for example. In certain instances, a voltage polarity provided by the power source can operate an electric motor in a clockwise direction wherein the voltage polarity applied to the electric motor by the battery can be reversed in order to operate the electric motor in a counter-clockwise direction. In various aspects, a microcontroller controls the electric motor through a motor driver via a pulse width modulated control signal. The motor driver can be configured to adjust the speed of the electric motor either in clockwise or counter-clockwise direction. The motor driver is also configured to switch between a plurality of operational modes which include an electronic motor braking mode, a constant speed mode, an electronic clutching mode, and a controlled current activation mode. In electronic braking mode, two terminal of the drive motor are shorted and the generated back EMF counteracts the rotation of the electric motor allowing for faster stopping and greater positional precision.

As used in any aspect herein, a wireless transmission such as, for example, a wireless communication or a wireless transfer of a data signal can be achieved, by a device including one or more transceivers. The transceivers may include, but are not limited to cellular modems, wireless mesh network transceivers, Wi-Fi® transceivers, low power wide area (LPWA) transceivers, and/or near field communications transceivers (NFC). The device may include or may be configured to communicate with a mobile telephone, a sensor system (e.g., environmental, position, motion, etc.) and/or a sensor network (wired and/or wireless), a computing system (e.g., a server, a workstation computer, a desktop computer, a laptop computer, a tablet computer (e.g., iPad®, GalaxyTab® and the like), an ultraportable computer, an ultramobile computer, a netbook computer and/or a subnotebook computer; etc. In at least one aspect of the present disclosure, one of the devices may be a coordinator node.

The transceivers may be configured to receive serial transmit data via respective universal asynchronous receiver-transmitters (UARTs) from a processor to modulate the serial transmit data onto an RF carrier to produce a transmit RF signal and to transmit the transmit RF signal via respective antennas. The transceiver(s) can be further configured to receive a receive RF signal via respective antennas that includes an RF carrier modulated with serial receive data, to demodulate the receive RF signal to extract the serial receive data and to provide the serial receive data to respective UARTs for provision to the processor. Each RF signal has an associated carrier frequency and an associated channel bandwidth. The channel bandwidth is associated with the carrier frequency, the transmit data and/or the receive data. Each RF carrier frequency and channel bandwidth is related to the operating frequency range(s) of the transceiver(s). Each channel bandwidth is further related to the wireless communication standard and/or protocol with which the transceiver(s) may comply. In other words, each transceiver may correspond to an implementation of a selected wireless communication standard and/or protocol, e.g., IEEE 802.11 a/b/g/n for Wi-Fi® and/or IEEE 802.15.4 for wireless mesh networks using Zigbee routing.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

In this specification, unless otherwise indicated, terms "about" or "approximately" as used in the present disclosure, unless otherwise specified, means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

In this specification, unless otherwise indicated, all numerical parameters are to be understood as being prefaced and modified in all instances by the term "about," in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques. Any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Also, all ranges recited herein are inclusive of the end points of the recited ranges. For example, a range of "1 to 10" includes the end points 1 and 10. Any maximum numerical limitation recited in this specification is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited. All such ranges are inherently described in this specification.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical instrument system, comprising:
   a motor system, comprising:
      a motor; and
      a drive train coupleable to the motor and configured to actuate a firing member through a staple firing stroke; and
   a control circuit coupled to the motor, wherein, during the staple firing stroke, the control circuit is configured to:
      determine a relative capacity of the motor system during an interrogation, wherein the interrogation comprises:
         setting the motor system to run the motor at an interrogation target speed for a period of time, wherein the interrogation target speed is greater than a current speed;
         measuring an actual response speed of the motor during the period of time; and
         determining a magnitude of a deviation between the actual response speed and the interrogation target speed during the interrogation; and
      increase the speed of the motor to a new speed upon determining that the magnitude of deviation is at or below a predetermined threshold of deviation.

2. The surgical instrument system of claim 1, wherein a magnitude of the difference between the current speed and the set interrogation target speed is such that transition from the current speed to setting the motor system to run the motor at the interrogation target speed is imperceptible to a user.

3. The surgical instrument system of claim 1, wherein the set interrogation target speed is equivalent to the new speed.

4. The surgical instrument system of claim 1,
   wherein the relatively capacity indicates an available capacity to increase the speed of the motor, and
   wherein the predetermined threshold of deviation comprises a predetermined percentage of the set interrogation target speed.

5. The surgical instrument system of claim 1, wherein the control circuit is configured to continuously determine the relative capacity of the motor system by initiating additional interrogations.

6. The surgical instrument system of claim 5, wherein a magnitude of speed increase for each subsequent interrogation is the same.

7. The surgical instrument system of claim 5, wherein a magnitude of speed increase for each subsequent interrogation increases logarithmically.

8. The surgical instrument system of claim 5, wherein a magnitude of speed increase for each subsequent interrogation increases non-linearly.

9. The surgical instrument system of claim 5, wherein the period of time for each subsequent interrogation is the same.

10. The surgical instrument system of claim 5, wherein the period of time for each subsequent interrogation is different.

11. The surgical instrument system of claim 1, wherein the motor is controlled by a pulse width modulation circuit, and wherein the control circuit is configured to increase a duty cycle of the pulse width modulation circuit to increase the speed of the motor.

* * * * *